United States Patent
Hannah et al.

(10) Patent No.: US 8,536,407 B2
(45) Date of Patent: Sep. 17, 2013

(54) HEAT RESISTANT PLANTS AND PLANT TISSUES COMPRISING A VARIANT ADENOSINE DIPHOSPHATE GLUCOSE PYROPHOSPHORYLASE SMALL SUBUNIT PROTEIN AND METHODS OF USE THEREOF

(75) Inventors: L. Curtis Hannah, Gainsville, FL (US); Nikolaos Georgelis, Lesvos (GR)

(73) Assignee: University of Florida Research Foundation, Inc., Gainesville, FL (US)

( * ) Notice: Subject to any disclaimer, the term of this patent is extended or adjusted under 35 U.S.C. 154(b) by 340 days.

(21) Appl. No.: 12/922,094

(22) PCT Filed: Mar. 26, 2009

(86) PCT No.: PCT/US2009/001903
§ 371 (c)(1),
(2), (4) Date: Dec. 1, 2010

(87) PCT Pub. No.: WO2009/126208
PCT Pub. Date: Oct. 15, 2009

(65) Prior Publication Data
US 2011/0078821 A1 Mar. 31, 2011

Related U.S. Application Data

(63) Continuation of application No. 12/082,339, filed on Apr. 9, 2008.

(51) Int. Cl.
*C12N 15/82* (2006.01)
*C12N 9/12* (2006.01)
*A01H 4/00* (2006.01)
*A01H 5/00* (2006.01)

(52) U.S. Cl.
USPC ..... 800/289; 800/298; 800/320.1; 800/320.2; 800/320.3; 800/321; 800/316; 800/294; 800/284; 536/23.4; 536/232.2; 536/23.6; 435/468; 435/183; 435/410; 435/419

(58) Field of Classification Search
None
See application file for complete search history.

(56) References Cited

U.S. PATENT DOCUMENTS

| | | | |
|---|---|---|---|
| 5,034,322 A | 7/1991 | Rogers et al. | |
| 5,106,739 A | 4/1992 | Comai et al. | |
| 5,589,610 A | 12/1996 | DeBeuckeleer et al. | |
| 5,589,618 A | 12/1996 | Hannah et al. | |
| 5,625,136 A | 4/1997 | Koziel et al. | |
| 5,639,948 A | 6/1997 | Michiels et al. | |
| 5,650,557 A | 7/1997 | Hannah et al. | |
| 5,661,017 A | 8/1997 | Dunahay et al. | |
| 5,872,216 A | 2/1999 | Hannah et al. | |
| 6,069,300 A | 5/2000 | Hannah et al. | |
| 6,184,438 B1 | 2/2001 | Hannah | |
| 6,403,863 B1 | 6/2002 | Hannah et al. | |
| 6,455,760 B1 | 9/2002 | Zhao et al. | |
| 6,462,185 B1 | 10/2002 | Takakura et al. | |
| 6,696,623 B1 | 2/2004 | Doerner et al. | |
| 6,809,235 B2 | 10/2004 | Hannah et al. | |
| 6,969,783 B2 | 11/2005 | Hannah et al. | |
| 7,173,165 B2 | 2/2007 | Hannah et al. | |
| 7,312,378 B2 | 12/2007 | Hannah et al. | |
| 2003/0084486 A1 | 5/2003 | Bruce et al. | |
| 2003/0177536 A1 | 9/2003 | Grundler et al. | |
| 2004/0019934 A1 | 1/2004 | Ekramoddoullah et al. | |
| 2004/0067506 A1 | 4/2004 | Scheres et al. | |
| 2004/0078841 A1 | 4/2004 | Atkinson et al. | |
| 2004/0123349 A1 | 6/2004 | Xie et al. | |
| 2009/0260101 A1* | 10/2009 | Hannah et al. | 800/278 |
| 2011/0167519 A1* | 7/2011 | Hannah et al. | 800/289 |

FOREIGN PATENT DOCUMENTS

| | | |
|---|---|---|
| EP | 1 528 104 | 4/2005 |
| WO | WO 2005/019425 | 3/2005 |

OTHER PUBLICATIONS

Friedberg. Automated protein function prediction—the genomic challenge. Briefings in Bioinformatics. 2006. 7(3): 225-242.*
Whitt, S.R. et al. "Genetic diversity and selection in the maize starch pathway" *PNAS*, 2002, 99(20):12959-12962.
Whitt, S.R. and Buckler, E.S., GenBank Accession No. AAN39328, "Brittle 2 [*Zea mays* subsp. mays]" Apr. 28, 2004.
Ballicora, M.A., et al. "Adenosine 5'-diphosphate-glucose pyrophosphorylase from potato tuber. Significance of the N-terminus of the small subunit for catalytic properties and heat stability" *Plant Physio.*, 1995, pp. 245-251, vol. 109.
Bhullar, S.S., et al., "Differential responses to high temperatures of starch and nitrogen accumulation in the grain of four cultivars of wheat" *Aust. J. Plant Physiol.*, 1985, pp. 363-375, vol. 12, No. 4.
Boehlein, S.K., et al., "Purification and characterization of adenosine diphosphnate glucose pyrophosphorylase from maize/potato mosaics" *Plant Physiol.*, 2005, pp. 1552-1562, vol. 138.

(Continued)

*Primary Examiner* — Cathy Kingdon Worley
*Assistant Examiner* — Ashley K Buran
(74) *Attorney, Agent, or Firm* — Saliwanchik, Lloyd & Eisenschenk

(57) ABSTRACT

The subject invention concerns materials and methods for providing plants or plant tissue with increased resistance to heat conditions and/or increased starch biosynthesis. Increased resistance of a plant or plant tissue to heat conditions provides for decreased yield losses as compared to the yield losses generally observed at elevated temperatures. One aspect of the invention concerns polynucleotides that encode a mutant plant small subunit of AGPase. The subject invention also comprises a mutant plant small subunit of AGPase encoded by a polynucleotide of the invention. The subject invention also concerns plants comprising a polynucleotide of the invention and method for making the plants.

19 Claims, 10 Drawing Sheets
(3 of 10 Drawing Sheet(s) Filed in Color)

(56) References Cited

OTHER PUBLICATIONS

Boehlein et al., "Heat stability and allosteric properties of maise endosperm ADP-glucose pyrophosphorylase are intimately intertwined", *Plant Physiology*, 2007, vol. 146, No. 1, pp. 289-299.

Chang, J., "Corn yield in relation to photoperiod, night temperature, and solar radiation" *Agricul. Metero.*, 1981, pp. 253-262, vol. 24.

Clancy, M., et al., "Splicing of the maize Sh1 first intron is essential for enhancement of gene expression, and a T-rich motif increases expression without affecting splicing" *Plant Physiol.*, 2002, pp. 918-929, vol. 130, No. 2.

Cross et al., "Both subunits of ADP-glucose pyrophosphorylase are regulatory", *Plant Physiology*, 2004, vol. 135, No. 1, pp. 137-144.

Deng, Z., et al., "Expression, characterization, and crystallization of the pyrophosphate-dependent phosphofructo-1-kinase of *Borrelia burgdorferi*" *Arch. Biochem. Biophys.*, 1999, pp. 326-331, vol. 371, Issue 2.

Duke, E., et al., "Effects of heat stress on enzyme activities and transcript levels in developing maize kernels grown in culture" *Environ. Exp. Botany*, 1996, pp. 199-208, vol. 35, No. 2.

Duncan, W.G., et al., "Net photosynthetic rates, relative leaf growth rates, and leaf Nos. of 22 races of maize grown at eight temperatures" *Crop Science*, 1968, pp. 670-674, vol. 8.

Furtado, A. et al. "Tools for Use in the Genetic Engineering of Barley" *Proceedings of the 10th Australian Barley technical Symposium, Canberra, ACT*, Australia, 2002.

Georgelis., N., et al., "The two AGPase subunits evolve at different rates in angiosperm, yet they are equally sensitive to activity altering amino acid changes when expressed in bacteria" *Plant Cell*, 2007, pp. 1458-1472, vol. 19.

Giroux, M.J., et al., "A single mutation that increases maize seed weight" *Proc. Natl. Acad. Sci. USA*, 1996, pp. 5824-5829, vol. 93.

Good, X. et al. "Reduced ethylene synthesis by transgenic tomatoes expressing S-adenosylmethionine hydrolase" *Plant Molec. Biol.*, 1994, pp. 781-790, vol. 26, No. 3.

Govons, S., et al., "Isolation of mutants of *Escherichia coli* B altered in their ability to synthesize glycogen" *J. Bacteriol.*, 1969, pp. 970-972, vol. 97, No. 2.

Greene, T.W., et al., "Enhanced stability of maize endosperm ADP-glucose pyrophosphorylase is gained through mutants that alter subunit interactions" *Proc. Natl. Acad. Sci. USA*, 1998a, pp. 13342-13347, vol. 95.

Greene, T.W., et al., "Assembly of maize endosperm ADP-glucose pyrophosphorylase requires motifs located throughout the large and small subunit units" *Plant Cell*, 1998b, pp. 1295-1306, vol. 10, No. 8.

Greene, T.W., et al., "Generation of up-regulated allosteric variants of potato ADP-glucose pyrophosphorylase by reversion genetics" *Proc. Natl. Acad. Sci. USA*, 1998, pp. 10322-10327, vol. 95, No. 17.

Hannah, L.C. and Nelson. Jr., O.E. "Characterization of ADP-glucose pyrophosphorylase from *Shrunken-2* and *Brittle-2* mutants of maize" *Biochemical Genetics*, 1976, 14(7-8):547-560.

Hannah, L.C., et al., "Maize Genes Encoding the Small Subunits of ADP-Glucose Pyrophosphorylase" *Plant Physiol.*, 2001, pp. 173-183, vol. 127.

Hannah, L.C., et al., "Multiple forms of maize endosperm ADP-glucose pyrophosphorylase and their control by Shrunken-2 and Brittle-2" *Genetics*, 1980, pp. 961-970, vol. 94, No. 4.

Hofstra, G. and Hesketh, J.D. "Effects of temperature on the gas exchange of leaves in the light and dark" *Plant (Berl.)*, 1969, 85:228-237.

Hunter et al., "Effects of photoperiod and temperature on vegetative and reproductive growth of a maize (*Zea mays*) hybrid", *Canadian Journal of Plant Science*, 1977, vol. 57, No. 4, pp. 1127-1133.

Hwang, Y-S. et al. "Analysis of the Rice Endosperm-Specific Globulin Promoter in Transformed Rice Cells" *Plant Cell Rep.*, 2002, pp. 842-847, vol. 20. No. 9.

Iglesias, A., et al., "Expression of the potato tuber ADP-glucose pyrophosphorylase in *Escherichia coli*" *J. Biol. Chem.*, 1993, pp. 1081-1086, vol. 268, No. 2.

Jin. X., et al., "Crystal structure of potato tuber ADP-glucose pyrophosphorylase" *EMBO J.*, 2005, pp. 694-704, vol. 24.

Jones, R., et al., Thermal environment during endosperm cell division and grain filling in maize: effects on kernel growth and development in vitro *Crop Science*, 1984, pp. 133-137, vol. 24.

Linebarger et al., "Heat stability of maize endosperm ADP-glucose pyrophosphorylase is enhanced by insertion of a cysteine in the N terminus of the small subunit", *Plant Physiology*, 2005, vol. 139, No. 4, pp. 1625-1634.

Nakamura, Y., et al., "Codon usage tabulated from international DNA sequence databases: status for the year 2000" *Nucleic Acids Res.*, 2000, p. 292, vol. 28, No. 1.

Obana, Y., et al., "Enhanced turnover of transitory starch by expression of up-regulated ADP-glucose pyrophosphorylase in *Arabidopsis thaliana*" *Plant Sci.*, 2006, pp. 1-11, vol. 170.

Peitsch, M.C. "Protein modeling by E-mail" *Nature Biotechnology*, 1995, pp. 658-660, vol. 13.

Peters, D.B., et al., "Effect of night air temperature on grain yield of corn, wheat and soybeans" *Agron. J.*, 1971, p. 809, vol. 63, No. 5.

Sakulsingharoja, C., et al., "Engineering starch biosynthesis for increasing rice seed weight: the role of the cytoplasmic ADP-glucose pyrophosphorylade" *Plant Sci.*, 2004, pp. 1323-1333, vol. 167.

Schwede, T., et al., "Swiss-Model: an automated protein homology-modeling server" *Nucleic Acids Res.*, 2003, pp. 3381-3385, vol. 31, No. 13.

Singletary, G., et al., "Decreased starch sythesis in heat stressed maize kernels results from reduced ADPG-pyrophosphorylase and starch synthase activities" *Plant Physiol. Suppl.*, 1993, p. 4, vol. 102.

Singletary, G., et al., "Heat stress during grain filling in maize: effects of carbohydrate storage and metabolism" *Aust J. Plant Physiol.*, 1994 pp. 829-841, vol. 21, No. 6.

Smidansky, E.D., et al., "Enhanced ADP-glucose pyrophosphorylase activity in wheat endosperm increases seed yield" *Proc. Natl. Acad. Sci.*, 2002, pp. 1724-1729, vol. 99, No. 3.

Smidansky, E.D., et al., "Seed yield and plant biomass increases in rice are conferred by deregulation of endosperm ADP-glucose pyrophosphorylase" *Planta*, 2003, pp. 656-664. vol. 216, No. 4.

Stark, D.M., et al., "Regulation of the amount of st arch in plant tissues by ADP-Glucose pyrophosphorylase" *Science*, 1992, pp. 287-292, vol. 258, No. 5080.

Thompson, L. "Weather variability, climatic change and grain production" *Science*, 1975, pp. 535-541, vol. 188, No. 4187.

Tollenaar et al., "Effects of temperature on rate and duration of kernel dry matter accumulation of maize", *Canadian Journal of Plant Science*, 1988, vol. 68, No. 4, pp. 934-940.

Tsai, C.Y., et al., "Starch deficient maize mutants lacking adenosine diphosphate glucose pyrophosphorylase activity" *Science*, 1966, pp. 341-343, vol. 151, No. 3708.

Wallwork, M.A.B., et al., "Effect of high temperature during grain filling on starch synthesis in the developing barley grain" *Aust. J. Plant Physiol.*, 1998, pp. 173-181, vol. 25, No. 2.

Wang, Z., et al., "Increasing maize seed weight by enhancing the cytoplasmic ADP-glucose pyrophosphorylase activity in transgenic plants" *Plant Cell Tiss. Organ Cult.*, 2007, pp. 83-92, vol. 88, No. 1.

Wilhelm, E., et al., "Heat stress during grain filling in maize: Effects on kernel growth and metabolism" *Crop Science*, 1999, pp. 1733-1741, vol. 39.

Wu, C-L. et al. (1998) "Promoters of Rice Seed Storage Protein Genes Direct Endosperm-Specific Gene Expression in Transgenic Rice" *Plant and Cell Physiology*, 1998, pp. 885-889, vol. 39, No. 8.

Xu, D., et al., "Systemic induction of a potato pin2 promoter by wounding, methyl jasmonate, and abscisic acid in transgenic rice plants" *Plant Molecular Biology*, 1993 pp. 573-588, vol. 22.

* cited by examiner

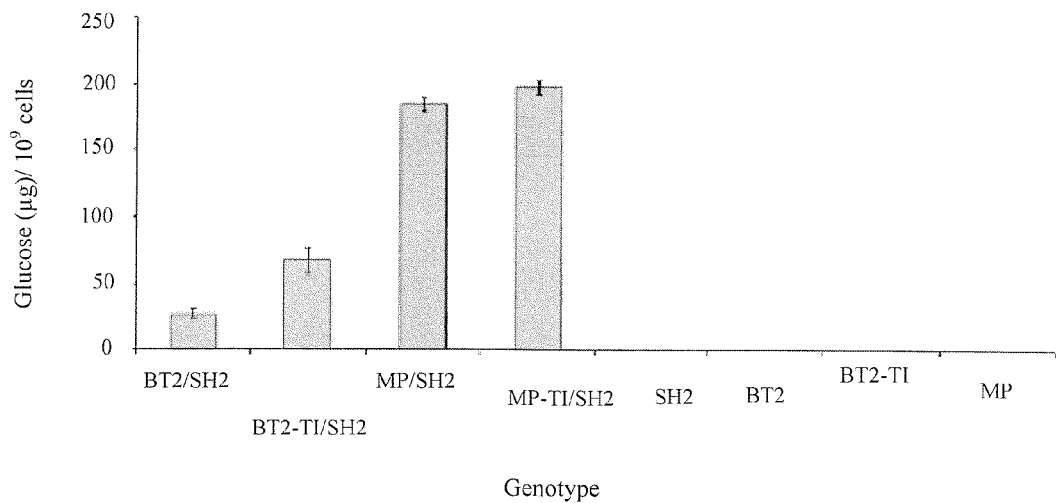
FIG. 1
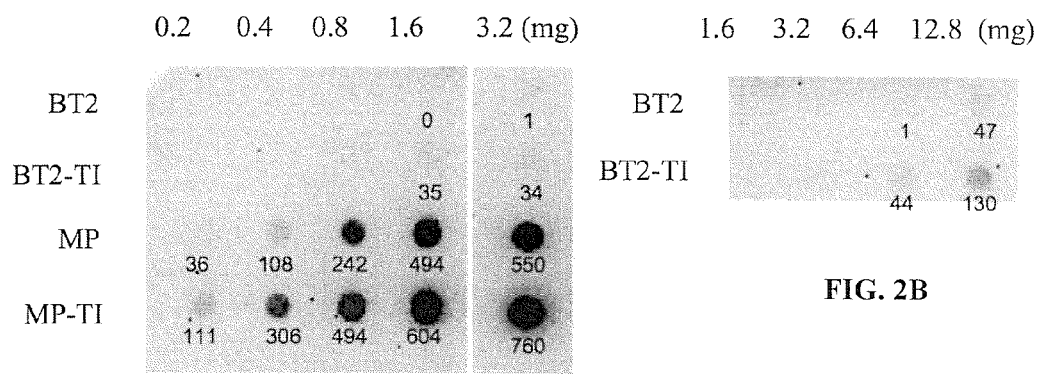
FIG. 2A
FIG. 2B 1-3: 3.90 Å
1-4: 3.92 Å
1-5: 3.81 Å
2-3: 5.23 Å
2-4: 4.16 Å
2-5: 4.31 Å

1-5: 5.25 Å
1-6: 5.02 Å
1-7: 4.33 Å
1-8: 3.39 Å
2-5: 3.90 Å
2-6: 3.76 Å
2-7: 4.53 Å
2-8: 4.00 Å
3-5: 4.30 Å
3-6: 4.44 Å
3-7: 5.60 Å
3-8: 5.25 Å
4-5: 3.27 Å
4-6: 3.61 Å
4-7: 6.02 Å
4-8: 5.96 Å

HEAT RESISTANT PLANTS AND PLANT TISSUES COMPRISING A VARIANT ADENOSINE DIPHOSPHATE GLUCOSE PYROPHOSPHORYLASE SMALL SUBUNIT PROTEIN AND METHODS OF USE THEREOF

CROSS-REFERENCE TO RELATED APPLICATIONS

This application is the National Stage of International Application Number PCT/US2009/001903, filed Mar. 26, 2009, which is a continuation of U.S. application Ser. No. 12/082,339, filed Apr. 9, 2008, each of which is hereby incorporated by reference herein in its entirety, including any figures, tables, nucleic acid sequences, amino acid sequences, or drawings.

GOVERNMENT SUPPORT

The subject matter of this application has been supported by a research grant from the National Science Foundation under grant number IOS-0444031. Accordingly, the government has certain rights in this invention.

BACKGROUND OF THE INVENTION

Heat stress leads to decreased maize yield (Peters et al., 1971; Thompson, 1975; Chang, 1981; Christy and Williamson, 1985). This can be attributed to reduced photosynthate availability and transportation from source to sink tissues, poor pollination, reduced cell and granule size and number, early seed abortion and/or reduced grain filling period. Growth of endosperm starts with a lag phase in which cells actively divide and continues with a linear phase in which cells increase in size and starch synthesis occurs. Elevated temperature during lag phase resulted in reduced yield (Jones et al., 1984). These investigators suggested that reduced yield was due to reduced cell and granule number and size as well as seed abortion. Additionally, elevated temperatures during the linear phase resulted in shorter grain filling period and subsequently smaller kernels (Jones et al., 1984). Similar results were found by Hunter et al. (1977) and Tollenaar and Bruulsema (1988).

Records from five states that traditionally produce more than 50% of the US corn showed that average daily temperature was 23.6° C., around 2° C. higher than optimum during grain filling (Singletary et al., 1994). Photosynthate availability during grain filling is not reduced at high temperatures, at least in barley and wheat. Indeed, sucrose content in barley and wheat seeds was either unchanged or elevated at high temperatures (Bhullar and Jenner, 1986; Wallwork et al., 1998). Also photosynthesis in maize increases up to 32° C. (Duncan and Hesketh, 1968; Hofstra and Hesketh, 1969; Christy et al., 1985). Moreover, Cheikhn and Jones (1995) studied the ability of maize kernels to fix $^{14}C$ sucrose and hexoses at different temperatures. They found that these sugars increased in the seed at elevated-temperatures. The evidence above suggests that limited sugar availability and transport into the kernel during grain filling are not the cause of temperature-induced yield decreases.

There have been extensive efforts to identify biochemical pathways that impact grain filling during elevated temperatures. Singletary et al. (1993; 1994) assayed starch biosynthetic enzymes in maize kernels grown in vitro at elevated temperatures (22° C. to 36° C.). They found that ADP-glucose pyrophosphorylase (AGPase) and soluble starch synthase (SSS) were more heat labile compared to other enzymes participating in starch synthesis. They suggested that heat lability of AGPase and SSS contributes to grain filling cessation. Duke and Doehlert (1996) found that transcripts of several genes encoding enzymes of the starch synthesis pathway, including those encoding AGPase, were decreased at 35° C. compared to 25° C. However, enzyme assays showed that only AGPase activity was strikingly lower. They suggested that this could be due to a higher turnover rate of AGPase compared to other enzymes. Finally, Wilhelm et al. (1999), through $Q_{10}$ analysis, showed that AGPase had the most pronounced reduction in activity compared to several other enzymes. Maize AGPase indeed lost 96% of its activity when heated at 57° C. for 5 min (Hannah et al., 1980).

AGPase catalyzes the first committed step in starch (plants) and glycogen (bacteria) synthesis. It involves the conversion of glucose-1-P (G-1-P) and ATP to ADP-glucose and pyrophosphate (PPi). AGPase is a heterotetramer in plants consisting of two identical small and two identical large subunits. The large and the small subunits are encoded by shrunken-2 (Sh2) and brittle-2 (Bt2) respectively in maize endosperm. AGPase is allosterically regulated by small effector molecules that are indicative of the energy status of the cell. AGPase is activated by 3-PGA, the first carbon assimilatory product, and inhibited/deactivated by inorganic phosphate (Pi) in cyanobacteria, green algae and angiosperms.

The importance of maize endosperm AGPase in starch synthesis has been shown by the kernel phenotype of mutants in either subunit of the enzyme. Indeed, such mutants result in shrunken kernels and a large reduction in endosperm starch content (Tsai and Nelson, 1966; Hannah and Nelson, 1976). There is also evidence that AGPase catalyses a rate-limiting step in starch synthesis (Stark et al. 1992; Giroux et al. 1996; Greene et al. 1998; Sakulsingharoja et al. 2004; Obana et al. 2006; Wang et al. 2007).

Greene and Hannah (1998a) isolated a mutant form of maize AGPase with a single amino acid change in the large subunit termed HS33. They showed that the altered enzyme was more heat-stable and that stability was due to stronger subunit-subunit interactions. When wheat and rice were transformed with a Sh2 variant that contains the HS33 change along with a change that affects the allosteric properties of AGPase (Rev6) (Giroux et al., 1996), yield was increased by 38% and 23% respectively (Smidansky et al., 2002; 2003). Remarkably, the increase was due to an increase in seed number rather than individual seed weight.

Transformation of maize with the Sh2 variant containing the Rev6 and HS33 changes also gives rise to enhanced seed number. Seed yield/ear can be increased up to 68% in maize. A detailed characterization of the maize transgenic events is under way (Greene and Hannah, in preparation). Enhanced seed number cannot be explained by Rev6 since, when expressed alone in maize, it increases only seed weight (Hannah, unpublished). The above studies show the importance of AGPase heat stability in cereal yield.

Cross et al. (2004) generated a mosaic small subunit (MP) consisting of the first 200 amino acids of BT2 and the last 275 amino acids of the potato tuber small subunit. MP in a complex with SH2 had several features that could lead to agronomic gain (Cross et al., 2004; Boehlein et al., 2005). Some of those features were increased activity in the absence of the activator 3-PGA, increased affinity for 3-PGA and elevated heat stability compared to wildtype maize endosperm AGPase (BT2/SH2). Preliminary data show that maize plants with transgenic MP containing AGPase variant expressed in maize endosperm provides for a starch yield increase (Hannah, unpublished data).

BRIEF SUMMARY OF THE INVENTION

The subject invention concerns materials and methods for providing plants or plant tissue with increased resistance to heat conditions and/or increased starch biosynthesis. Increased resistance of a plant or plant tissue to heat conditions provides for decreased yield losses as compared to the yield losses generally observed at elevated temperatures. One aspect of the invention concerns polynucleotides that encode a mutant plant small subunit of AGPase. In one embodiment, a polynucleotide of the invention encodes a plant AGPase small subunit having an amino acid mutation wherein the threonine amino acid corresponding to amino acid position 462 of wild type maize AGPase small subunit is substituted with an amino acid that confers increased heat stability. In another embodiment, a polynucleotide encodes a chimeric plant AGPase small subunit composed of sequences from two different plants (as described in U.S. Pat. No. 7,173,165) and comprising an amino acid mutation of the invention wherein the threonine amino acid corresponding to amino acid position 462 of wild type maize AGPase small subunit is substituted with an amino acid that confers increased heat stability. The mutation in the chimeric AGPase synergistically enhances heat stability. The subject invention also comprises a mutant plant small subunit of AGPase encoded by a polynucleotide of the invention. Characterization of heat stability as well as kinetic and allosteric properties indicates increased starch yield is provided when the polynucleotides of the invention are expressed in plants such as monocot endosperms.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1 shows glycogen produced by *E. coli* cells expressing BT2, BT2-TI, MP, MP-TI along with SH2. Glycogen from cells expressing only SH2, BT2, BT2-TI, and MP alone. Glycogen is measured in glucose units. The error bars indicate standard deviation (N=3).

FIGS. 2A and 2B show dot blots of crude extracts from *E. coli* cells expressing BT2, BT2-TI, MP, MP-TI with the complementary subunit SH2. AGPase was visualized by using a monoclonal antibody against BT2. The density of the spots was estimated by using ImageJ.

In FIG. 5A, the assay was conducted in the forward direction. In FIG. 5B, the assay was conducted in the reverse direction.

In FIG. 6A, the assay was conducted in the forward direction. In FIG. 6B, the assay was conducted in the reverse direction.

FIG. 7A is the predicted 3D structure of BT2 monomer. The TI change is marked by a red circle. The areas of BT2 that are directly involved in subunit-subunit interactions are highlighted by yellow boxes. FIG. 7B shows the distances of carbon atoms of Thr462 (1,2) from those of Pro60 (4,5) and Leu61 (3). FIG. 7C shows the distances of carbon atoms of Ile462 (1,2,3,4) from those of Pro60 (5,6) and Leu61 (7,8). The Thr462 and Ile462 contacting residues were determined by using First-Glance Jmol. Dark gray spheres indicate carbon atoms of Thr462 and Ile462. Light gray spheres indicate carbon atoms of contacting residues. Oxygen and nitrogen atoms are indicated by red and blue color respectively.

BRIEF DESCRIPTION OF THE SEQUENCES

Figure 3:
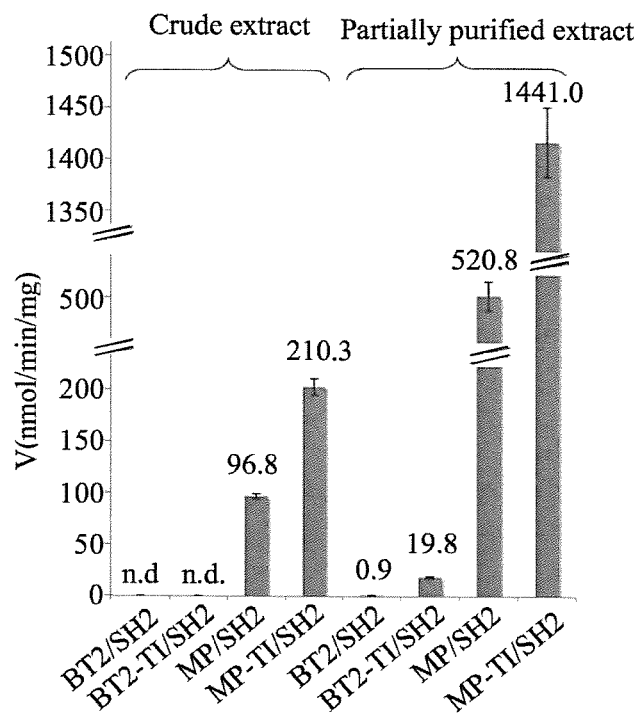
FIG. 3 shows specific activity of AGPase variants in crude and partially purified protein extracts from non-induced *E. coli* cells. Activity was measured in the reverse direction. n.d.=not detectable. The error bars indicate standard deviation (N=3).

SEQ ID NO:1 is a polynucleotide sequence comprising a nucleotide sequence encoding a mutant polypeptide (TI) of the invention.

SEQ ID NO:2 is an amino acid sequence of a mutant polypeptide (TI) of the invention.

SEQ ID NO:3 is a polynucleotide sequence comprising a nucleotide sequence encoding a mutant polypeptide (MP-TI) of the invention.

SEQ ID NO:4 is an amino acid sequence of a mutant polypeptide (MP-TI) of the invention.

SEQ ID NO:5 is an amino acid sequence of a mutant polypeptide (TI+YC) of the invention.

SEQ ID NO:6 is an amino acid sequence of a mutant polypeptide (TI+QTCL) of the invention.

SEQ ID NO:7 is an amino acid sequence of a mutant polypeptide (TI+ETCL) of the invention.

SEQ ID NO:8 is an amino acid sequence of a mutant polypeptide (MP-TI+YC) of the invention.

SEQ ID NO:9 is an amino acid sequence of a mutant polypeptide (MP-TI+QTCL) of the invention.

SEQ ID NO:10 is an amino acid sequence of a mutant polypeptide (MP-TI+ETCL) of the invention.

SEQ ID NO:11 is a polynucleotide sequence comprising a nucleotide sequence encoding a mutant polypeptide (SEQ ID NO:5) of the invention.

SEQ ID NO:12 is a polynucleotide sequence comprising a nucleotide sequence encoding a mutant polypeptide (SEQ ID NO:6) of the invention.

SEQ ID NO:13 is a polynucleotide sequence comprising a nucleotide sequence encoding a mutant polypeptide (SEQ ID NO:7) of the invention.

SEQ ID NO:14 is a polynucleotide sequence comprising a nucleotide sequence encoding a mutant polypeptide (SEQ ID NO:8) of the invention.

SEQ ID NO:15 is a polynucleotide sequence comprising a nucleotide sequence encoding a mutant polypeptide (SEQ ID NO:9) of the invention.

SEQ ID NO:16 is a polynucleotide sequence comprising a nucleotide sequence encoding a mutant polypeptide (SEQ ID NO:10) of the invention.

SEQ ID NO:17 is an oligonucleotide that can be used according to the present invention.

SEQ ID NO:18 is an oligonucleotide that can be used according to the present invention.

SEQ ID NO:19 is an oligonucleotide that can be used according to the present invention.

SEQ ID NO:20 is an oligonucleotide that can be used according to the present invention.

SEQ ID NO:21 is an amino acid sequence of a mutant polypeptide (TI) of the invention.

SEQ ID NO:22 is an amino acid sequence of a mutant polypeptide (TI) of the invention.

SEQ ID NO:23 is an amino acid sequence of a mutant polypeptide (TI) of the invention.

SEQ ID NO:24 is an amino acid sequence of a mutant polypeptide (TI) of the invention.

SEQ ID NO:25 is an amino acid sequence of a mutant polypeptide (TI) of the invention.

SEQ ID NO:26 is an amino acid sequence of potato tuber AGPase small subunit protein.

DETAILED DESCRIPTION OF THE INVENTION

The subject invention concerns materials and methods for providing plants with increased resistance to heat conditions and/or increased starch biosynthesis. Increased resistance of a plant to heat conditions provides for decreased yield losses as compared to yield losses generally observed at elevated temperatures.

One aspect of the invention concerns polynucleotides that encode a mutant plant small subunit of AGPase. In one embodiment, a polynucleotide of the invention encodes a plant AGPase small subunit having an amino acid mutation wherein the threonine amino acid corresponding to amino acid position 462 of wild type maize endosperm AGPase small subunit is substituted with an amino acid that confers increased heat stability. In a specific embodiment, the amino acid substituted is an isoleucine. In one embodiment, the mutant plant AGPase small subunit is maize endosperm AGPase small subunit. In an exemplified embodiment, the mutant plant AGPase small subunit comprises the amino acid sequence shown in SEQ ID NO:2, or a fragment or variant thereof. In a specific embodiment, the polynucleotide comprises the nucleotide sequence shown in SEQ ID NO:1, or a fragment or variant thereof. In another embodiment, the mutant plant AGPase small subunit is barley, wheat, sorghum, potato, or rice. In a specific embodiment, the mutant barley, wheat, sorghum, rice, or potato AGPase small subunit comprises the amino acid sequence shown in SEQ ID NO:21, SEQ ID NO:22, SEQ ID NO:23, SEQ ID NO:24, or SEQ ID NO:25, respectively. In another embodiment, the polynucleotide encodes a mutant plant AGPase small subunit that can additionally comprise an amino acid mutation as described in published International patent application WO 2005/019425 (Hannah and Linebarger). In one embodiment, the mutant AGPase small subunit encoded by the polynucleotide comprises an amino acid mutation wherein the tyrosine corresponding to amino acid position 36 of wild type maize endosperm AGPase is substituted with a cysteine. The mutant AGPase small subunit can also optionally comprise an amino acid inserted between the serine and threonine amino acids corresponding to amino acid positions 34 and 35 of wild type maize endosperm AGPase, respectively. In specific embodiments, the amino acid inserted between amino acids at position 34 and 35 of the AGPase small subunit is a glutamic acid or glutamine. In exemplified embodiments, the mutant plant AGPase small subunit comprises the amino acid sequence shown in SEQ ID NO:5, SEQ ID NO:6, or SEQ ID NO:7, or a fragment or variant thereof. In specific embodiments, the polynucleotide comprises the nucleotide sequences shown in SEQ ID NO:11, SEQ ID NO:12, or SEQ ID NO:13, or a fragment or variant thereof.

In another embodiment, a polynucleotide encodes a chimeric plant AGPase small subunit composed of sequences from two different plants (as described in U.S. Pat. No. 7,173, 165) and also comprising an amino acid mutation of the invention wherein the threonine amino acid corresponding to amino acid position 462 of wild type maize endosperm AGPase small subunit is substituted with an amino acid that confers increased heat stability. In a specific embodiment, the amino acid substituted is an isoleucine. In one embodiment, the chimeric AGPase small subunit comprises a C-terminal portion from one plant and an N-terminal portion from another plant. In one embodiment, a chimeric protein of the present invention comprises an N-terminus sequence having approximately the first 150 to 250 amino acids of the N-terminus of a first plant AGPase small subunit and a C-terminus sequence comprising approximately the terminal 300 residues or less of the C-terminus of a second plant AGPase small subunit. Thus, the C-terminus of the chimeric subunit can comprise the terminal 300, or 299, or 298, or 297, or 296, or 295, and so forth, residues of the C-terminus of the second plant. The subunit sequences can be from an AGPase of a monocot or dicot plant, or both a monocot and a dicot. Monocotyledonous plants, such as, for example, rice, wheat, barley, oats, sorghum, maize, lilies, and millet are included within the scope of the invention. Dicot plants can include, for example, tobacco, soybean, potato, sweet potato, radish, cabbage, rape, apple tree, and lettuce. In one embodiment, the first 200 or so amino acids of the N-terminus of the chimeric protein are from the N-terminus of maize endosperm AGPase small subunit and the C-terminus amino acids are from the C-terminus of potato tuber AGPase small subunit and include the mutation corresponding to amino acid position 462 of the present invention. In a specific embodiment, the C-terminus region of a chimeric protein of the present invention comprises the terminal 276 amino acids of the AGPase small subunit of potato tuber. In an exemplified embodiment, the chimeric protein comprises a portion of the small subunit of maize endosperm AGPase and a portion of the small subunit of potato tuber AGPase. In a specific embodiment, the chimeric protein contains a) the first 199 amino acids (i.e., amino acids 1 through 199) from the small subunit of maize endosperm AGPase and the carboxyl terminal end of the small subunit of potato tuber AGPase, starting at amino acid 246 (i.e., amino acids 246 through 521) using the amino acid sequence shown for the protein deposited as Genbank accession number X61186 (or, alternatively, starting at amino acid 175 using the numbering system for the potato AGPase subunit as in Hannah et al., 2001) and b) the mutation corresponding to amino acid position 462 of the present invention. In an exemplified embodiment, the plant chimeric AGPase small subunit comprises the amino acid sequence shown in SEQ ID NO:4, or a fragment or variant thereof. In a specific embodiment, the polynucleotide comprises the nucleotide sequence shown in SEQ ID NO:3, or a fragment or variant thereof. In another embodiment, the polynucleotide encodes a mutant plant AGPase small subunit that can additionally comprise an amino acid mutation described in published International patent application WO 2005/019425 (Hannah and Linebarger). In a further embodiment, the mutant AGPase small subunit encoded by the polynucleotide also comprises an amino acid mutation wherein a tyrosine at position 36 is substituted with a cysteine. The mutant AGPase small subunit can also optionally comprise an amino acid inserted between the serine and threonine amino acids at positions 34 and 35, respectively. In specific embodiments, the amino acid inserted between position 34 and 35 of the mutant AGPase small subunit is a glutamic acid or glutamine. In exemplified embodiments, the mutant plant AGPase small subunit comprises the amino acid sequence shown in SEQ ID NO:8, SEQ ID NO:9, or SEQ ID NO:10, or a fragment or variant thereof. In specific embodiments, the polynucleotide comprises the nucleotide sequences shown in SEQ ID NO:14, SEQ ID NO:15, or SEQ ID NO:16, or a fragment or variant thereof.

The subject invention also concerns methods for increasing heat stability and/or increasing starch biosynthesis, and increasing crop yield of a plant or plant tissue. In one embodiment, a method of the invention comprises introducing one or more polynucleotides of the present invention into a plant. In certain embodiments, the polynucleotides introduced into the plant encode one or more polypeptides comprising the amino acid sequence shown in any of SEQ ID NO:2, SEQ ID NO:4, SEQ ID NO:5, SEQ ID NO:6, SEQ ID NO:7, SEQ ID NO:8, SEQ ID NO:9, SEQ ID NO:10, SEQ ID NO:21, SEQ ID NO:22, SEQ ID NO:23, SEQ ID NO:24, or SEQ ID NO:25, or a fragment or variant thereof. In a specific embodiment, the polynucleotide comprises the nucleotide sequence shown in SEQ ID NO:1, or SEQ ID NO:3, or a fragment or variant thereof. In further specific embodiments, the polynucleotide comprises the nucleotide sequences shown in SEQ ID NO:11, SEQ ID NO:12, SEQ ID NO:13, SEQ ID NO:14, SEQ ID NO:15, or SEQ ID NO:16, or a fragment or variant thereof. In one embodiment, the polynucleotide is stably incorporated into the genome of the plant or plant tissue. The polynucleotide can comprise regulatory elements, such as a promoter and/or enhancer sequences, that provide for increased expression of the polynucleotide and/or the polypeptide encoded thereby. In a specific embodiment, the promoter sequence is one that provides for constitutive or tissue-specific (e.g., endosperm) expression. Plants or plant tissues containing the polynucleotide, or progeny of the plants, optionally can be screened for increased expression of a polynucleotide or polypeptide of the invention. In one embodiment, multiple copies of one or more polynucleotides of the invention are introduced into a plant or plant tissue and stably incorporated into the genome of the plant. In one embodiment, a polynucleotide of the invention is provided in an expression construct as described herein.

The subject invention also concerns mutant AGPase small subunit polypeptides encoded by the polynucleotides of the invention. In one embodiment, the polypeptide comprises the amino acid sequence shown in SEQ ID NO:2, or a fragment or variant thereof. In other embodiments, the polypeptide comprises the amino acid sequence shown in SEQ ID NO:21, SEQ ID NO:22, SEQ ID NO:23, SEQ ID NO:24, or SEQ ID NO:25, or a fragment or variant thereof. In another embodiment, the polypeptide comprises the amino acid sequence shown in SEQ ID NO:4, or a fragment or variant thereof. In still a further embodiment, the polypeptide comprises the amino acid sequence shown in any of SEQ ID NO:5, SEQ ID NO:6, SEQ ID NO:7, SEQ ID NO:8, SEQ ID NO:9, or SEQ ID NO:10, or a fragment or variant thereof.

The subject invention also concerns mutant plant AGPase enzymes comprising one or more mutant AGPase small subunit polypeptides of the invention. The mutant plant AGPase can also comprise one or more wild type AGPase large subunit polypeptides. In specific embodiments, a mutant plant AGPase enzyme comprises one or more mutant AGPase small subunit polypeptides any of which can comprise the amino acid sequence of SEQ ID NO:2, SEQ ID NO:4, SEQ ID NO:5, SEQ ID NO:6, SEQ ID NO:7, SEQ ID NO:8, SEQ ID NO:9, SEQ ID NO:10, SEQ ID NO:21, SEQ ID NO:22, SEQ ID NO:23, SEQ ID NO:24, or SEQ ID NO:25, or a fragment or variant of any such sequence, wherein the mutant AGPase enzyme exhibits increased heat stability relative to a wild type AGPase enzyme. In one embodiment, the mutant plant enzyme comprises two mutant AGPase small subunits of the invention, wherein the mutant polypeptides can have the same mutation(s) or can have different mutation(s). The subject invention also concerns mutant plant AGPase enzymes comprising one or more mutant AGPase small subunit polypeptides of the invention and one or more mutant AGPase large subunit polypeptides. In one embodiment, the mutant AGPase large subunit polypeptide can be any of those as described in any of U.S. Pat. Nos. 5,589,618; 5,650,557; 5,872,216; 6,069,300; 6,184,438; 6,403,863; 6,809,235; 7,173,165; 7,312,378; and 6,969,783. In one embodiment, a mutant AGPase large subunit polypeptide comprises a Rev6 mutation. In another embodiment, a mutant AGPase large subunit polypeptide comprises one or more heat stable (HS) mutations, as described in U.S. Pat. Nos. 6,069,300; 6,403,863; 6,809,235; 7,312,378; and 6,969,783, and published International patent application nos. WO 99/58698; WO 2003/0070901; WO 98/22601; and WO 02/072784, such as, for example, the HS33 mutation. In one embodiment, the mutant plant AGPase enzyme comprises two mutant AGPase small subunit polypeptides of the invention, wherein the mutant AGPase small subunit polypeptides can have the same mutation(s) or can have different mutation(s), as described herein. In another embodiment, the mutant plant AGPase enzyme comprises two mutant AGPase large subunit polypeptides wherein the mutant AGPase large subunit polypeptides can have the same mutation(s) or can have different mutation(s). In a further embodiment, the mutant plant AGPase enzyme comprises two mutant AGPase small subunit polypeptides of the invention and two mutant SH2 polypeptides, wherein the mutant AGPase small subunit polypeptides and the mutant AGPase large subunit polypeptides can have the same mutation(s) or can have different mutation(s), as described herein.

The subject invention also concerns methods for providing for a mutant plant AGPase enzyme having increased heat stability relative to wild type plant AGPase. In one embodiment, the method comprises incorporating or providing one or more mutant AGPase small subunit polypeptides of the present invention with wild type or mutant AGPase large subunits in an AGPase enzyme. In one embodiment, the AGPase enzyme comprises a tetramer of polypeptide subunits, wherein one, two, or more of the subunits is a mutant polypeptide of the present invention. In one embodiment, the AGPase enzyme also comprises a mutant AGPase large subunit polypeptide subunit, such as a mutant large subunit comprising a Rev6 and/or a heat stability mutation, such as HS33.

The subject invention also concerns plants, plant tissue, and plant cells of the invention that comprise a polynucleotide or the protein encoded by the polynucleotide of the invention, or that express a mutant polypeptide of the invention, or a fragment or variant thereof, or that comprise or express a mutant plant AGP enzyme of the present invention. Plant tissue includes, but is not limited to, seed, scion, and rootstock. Plants within the scope of the present invention include monocotyledonous plants, such as, for example, rice, wheat, barley, oats, rye, sorghum, maize, sugarcane, pineapple, onion, bananas, coconut, lilies, turfgrasses, and millet. Plants within the scope of the present invention also include dicotyledonous plants, such as, for example, tomato, cucumber, squash, peas, alfalfa, melon, chickpea, chicory, clover, kale, lentil, soybean, beans, tobacco, potato, sweet potato, yams, cassava, radish, broccoli, spinach, cabbage, rape, apple trees, citrus (including oranges, mandarins, grapefruit, lemons, limes and the like), grape, cotton, sunflower, strawberry, lettuce, and hop. Herb plants containing a polynucleotide of the invention are also contemplated within the scope of the invention. Herb plants include parsley, sage, rosemary, thyme, and the like. In one embodiment, the plant, plant tissue, or plant cell is *Zea mays*. In one embodiment, a plant, plant tissue, or plant cell is a transgenic plant, plant tissue, or plant cell. In another embodiment, a plant, plant tissue, or plant cell is one that has been obtained through a breeding program.

Polynucleotides useful in the present invention can be provided in an expression construct. Expression constructs of the invention generally include regulatory elements that are functional in the intended host cell in which the expression construct is to be expressed. Thus, a person of ordinary skill in the art can select regulatory elements for use in bacterial host cells, yeast host cells, plant host cells, insect host cells, mammalian host cells, and human host cells. Regulatory elements include promoters, transcription termination sequences, translation termination sequences, enhancers, and polyadenylation elements. As used herein, the term "expression construct" refers to a combination of nucleic acid sequences that provides for transcription of an operably linked nucleic acid sequence. As used herein, the term "operably linked" refers to a juxtaposition of the components described wherein the components are in a relationship that permits them to function in their intended manner. In general, operably linked components are in contiguous relation.

An expression construct of the invention can comprise a promoter sequence operably linked to a polynucleotide sequence encoding a mutant polypeptide of the invention. Promoters can be incorporated into a polynucleotide using standard techniques known in the art. Multiple copies of promoters or multiple promoters can be used in an expression construct of the invention. In a preferred embodiment, a promoter can be positioned about the same distance from the transcription start site in the expression construct as it is from the transcription start site in its natural genetic environment. Some variation in this distance is permitted without substantial decrease in promoter activity. A transcription start site is typically included in the expression construct.

If the expression construct is to be provided in or introduced into a plant cell, then plant viral promoters, such as, for example, a cauliflower mosaic virus (CaMV) 35S (including the enhanced CaMV 35S promoter (see, for example U.S. Pat. No. 5,106,739)) or a CaMV 19S promoter or a cassava vein mosaic can be used. Other promoters that can be used for expression constructs in plants include, for example, prolifera promoter, Ap3 promoter, heat shock promoters, T-DNA 1'- or 2'-promoter of *A. tumefaciens*, polygalacturonase promoter, chalcone synthase A (CHS-A) promoter from petunia, tobacco PR-1a promoter, ubiquitin promoter, actin promoter, alcA gene promoter, pin2 promoter (Xu et al., 1993), maize WipI promoter, maize trpA gene promoter (U.S. Pat. No. 5,625,136), maize CDPK gene promoter, and RUBISCO SSU promoter (U.S. Pat. No. 5,034,322) can also be used. Tissue-specific promoters, for example fruit-specific promoters, such as the E8 promoter of tomato (accession number: AF515784; Good et al. (1994)) can be used. Fruit-specific promoters such as flower organ-specific promoters can be used with an expression construct of the present invention for expressing a polynucleotide of the invention in the flower organ of a plant. Examples of flower organ-specific promoters include any of the promoter sequences described in U.S. Pat. Nos. 6,462,185; 5,639,948; and 5,589,610. Seed-specific promoters such as the promoter from a β-phaseolin gene (for example, of kidney bean) or a glycinin gene (for example, of soybean), and others, can also be used. Endosperm-specific promoters include, but are not limited to, MEG1 (EPO application No. EP1528104) and those described by Wu et al. (1998), Furtado et al. (2001), and Hwang et al. (2002). Root-specific promoters, such as any of the promoter sequences described in U.S. Pat. No. 6,455,760 or U.S. Pat. No. 6,696,623, or in published U.S. patent application Nos. 20040078841; 20040067506; 20040019934; 20030177536; 20030084486; or 20040123349, can be used with an expression construct of the invention. Constitutive promoters (such as the CaMV, ubiquitin, actin, or NOS promoter), developmentally-regulated promoters, and inducible promoters (such as those promoters than can be induced by heat, light, hormones, or chemicals) are also contemplated for use with polynucleotide expression constructs of the invention.

Expression constructs of the invention may optionally contain a transcription termination sequence, a translation termination sequence, a sequence encoding a signal peptide, and/or enhancer elements. Transcription termination regions can typically be obtained from the 3' untranslated region of a eukaryotic or viral gene sequence. Transcription termination sequences can be positioned downstream of a coding sequence to provide for efficient termination. A signal peptide sequence is a short amino acid sequence typically present at the amino terminus of a protein that is responsible for the relocation of an operably linked mature polypeptide to a wide range of post-translational cellular destinations, ranging from a specific organelle compartment to sites of protein action and the extracellular environment. Targeting gene products to an intended cellular and/or extracellular destination through the use of an operably linked signal peptide sequence is contemplated for use with the polypeptides of the invention. Classical enhancers are cis-acting elements that increase gene transcription and can also be included in the expression construct. Classical enhancer elements are known in the art, and include, but are not limited to, the CaMV 35S enhancer element, cytomegalovirus (CMV) early promoter enhancer element, and the SV40 enhancer element. Intron-mediated enhancer elements that enhance gene expression are also known in the art. These elements must be present within the transcribed region and are orientation dependent. Examples include the maize shrunken-1 enhancer element (Clancy and Hannah, 2002).

DNA sequences which direct polyadenylation of mRNA transcribed from the expression construct can also be included in the expression construct, and include, but are not limited to, an octopine synthase or nopaline synthase signal. The expression constructs of the invention can also include a polynucleotide sequence that directs transposition of other genes, i.e., a transposon.

Polynucleotides of the present invention can be composed of either RNA or DNA. Preferably, the polynucleotides are composed of DNA. The subject invention also encompasses those polynucleotides that are complementary in sequence to the polynucleotides disclosed herein. Polynucleotides and polypeptides of the invention can be provided in purified or isolated form.

Because of the degeneracy of the genetic code, a variety of different polynucleotide sequences can encode mutant polypeptides of the present invention. A table showing all possible triplet codons (and where U also stands for T) and the amino acid encoded by each codon is described in Lewin (1985). In addition, it is well within the skill of a person trained in the art to create alternative polynucleotide sequences encoding the same, or essentially the same, mutant polypeptides of the subject invention. These variant or alternative polynucleotide sequences are within the scope of the subject invention. As used herein, references to "essentially the same" sequence refers to sequences which encode amino acid substitutions, deletions, additions, or insertions which do not materially alter the functional activity of the polypeptide encoded by the polynucleotides of the present invention. Allelic variants of the nucleotide sequences encoding a wild type or mutant polypeptide of the invention are also encompassed within the scope of the invention.

Substitution of amino acids other than those specifically exemplified or naturally present in a wild type or mutant polypeptide and/or AGPase enzyme of the invention are also contemplated within the scope of the present invention. For example, non-natural amino acids can be substituted for the amino acids of a mutant AGPase small subunit polypeptide, so long as the mutant polypeptide having the substituted amino acids retains substantially the same functional activity as the mutant polypeptide in which amino acids have not been substituted. Examples of non-natural amino acids include, but are not limited to, ornithine, citrulline, hydroxyproline, homoserine, phenylglycine, taurine, iodotyrosine, 2,4-diaminobutyric acid, a-amino isobutyric acid, 4-aminobutyric acid, 2-amino butyric acid, γ-amino butyric acid, e-amino hexanoic acid, 6-amino hexanoic acid, 2-amino isobutyric acid, 3-amino propionic acid, norleucine, norvaline, sarcosine, homocitrulline, cysteic acid, t-butylglycine, t-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) form or L (levorotary) form. Allelic variants of a protein sequence of a wild type or mutant AGPase small or large subunit polypeptide of the present invention are also encompassed within the scope of the invention.

Amino acids can be generally categorized in the following classes: non-polar, uncharged polar, basic, and acidic. Conservative substitutions whereby a mutant AGPase small subunit polypeptide of the present invention and/or a wild type or mutant AGPase large subunit polypeptide having an amino acid of one class is replaced with another amino acid of the same class fall within the scope of the subject invention so long as the polypeptide having the substitution still retains substantially the same functional activity (e.g., enzymatic and/or increased heat stability of an AGPase enzyme) as the polypeptide that does not have the substitution. Polynucleotides encoding a mutant AGPase small subunit polypeptide and/or a wild type or mutant AGPase large subunit polypeptide having one or more amino acid substitutions in the sequence are contemplated within the scope of the present invention. Table 1 below provides a listing of examples of amino acids belonging to each class.

TABLE 1

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

The subject invention also concerns variants of the polynucleotides of the present invention that encode functional wild type or mutant AGPase small or large subunit polypeptides of the invention. Variant sequences include those sequences wherein one or more nucleotides of the sequence have been substituted, deleted, and/or inserted. The nucleotides that can be substituted for natural nucleotides of DNA have a base moiety that can include, but is not limited to, inosine, 5-fluorouracil, 5-bromouracil, hypoxanthine, 1-methylguanine, 5-methylcytosine, and tritylated bases. The sugar moiety of the nucleotide in a sequence can also be modified and includes, but is not limited to, arabinose, xylulose, and hexose. In addition, the adenine, cytosine, guanine, thymine, and uracil bases of the nucleotides can be modified with acetyl, methyl, and/or thio groups. Sequences containing nucleotide substitutions, deletions, and/or insertions can be prepared and tested using standard techniques known in the art.

Fragments and variants of a mutant polypeptide of the present invention can be generated as described herein and tested for the presence of enzymatic and heat stable function using standard techniques known in the art. Thus, an ordinarily skilled artisan can readily prepare and test fragments and variants of a mutant polypeptide of the invention and determine whether the fragment or variant retains functional activity relative to full-length or a non-variant mutant polypeptide.

Polynucleotides and polypeptides contemplated within the scope of the subject invention can also be defined in terms of more particular identity and/or similarity ranges with those sequences of the invention specifically exemplified herein. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein. Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used. See NCBI/NIH website.

The subject invention also contemplates those polynucleotide molecules having sequences which are sufficiently homologous with the polynucleotide sequences exemplified herein so as to permit hybridization with that sequence under standard stringent conditions and standard methods (Maniatis et al., 1982). As used herein, "stringent" conditions for hybridization refers to conditions wherein hybridization is typically carried out overnight at 20-25 C below the melting temperature (Tm) of the DNA hybrid in 6×SSPE, 5×Denhardt's solution, 0.1% SDS, 0.1 mg/ml denatured DNA. The melting temperature, Tm, is described by the following formula (Beltz et al., 1983):

$$Tm=81.5C+16.6 \, \text{Log}[Na+]+0.41(\% \, G+C)-0.61(\% \, \text{formamide})-600/\text{length of duplex in base pairs}.$$

Washes are typically carried out as follows:

(1) Twice at room temperature for 15 minutes in 1×SSPE, 0.1% SDS (low stringency wash).

(2) Once at Tm-20 C for 15 minutes in 0.2×SSPE, 0.1% SDS (moderate stringency wash).

As used herein, the terms "nucleic acid" and "polynucleotide" refer to a deoxyribonucleotide, ribonucleotide, or a mixed deoxyribonucleotide and ribonucleotide polymer in either single- or double-stranded form, and unless otherwise limited, would encompass known analogs of natural nucleotides that can function in a similar manner as naturally-occurring nucleotides. The polynucleotide sequences include the DNA strand sequence that is transcribed into RNA and the strand sequence that is complementary to the DNA strand that is transcribed. The polynucleotide sequences also include both full-length sequences as well as shorter sequences derived from the full-length sequences. Allelic variations of the exemplified sequences also fall within the scope of the subject invention. The polynucleotide sequence includes both the sense and antisense strands either as individual strands or in the duplex.

Techniques for transforming plant cells with a gene are known in the art and include, for example, *Agrobacterium* infection, biolistic methods, electroporation, calcium chloride treatment, PEG-mediated transformation, etc. U.S. Pat. No. 5,661,017 teaches methods and materials for transforming an algal cell with a heterologous polynucleotide. Transformed cells can be selected, redifferentiated, and grown into plants that contain and express a polynucleotide of the invention using standard methods known in the art. The seeds and other plant tissue and progeny of any transformed or transgenic plant cells or plants of the invention are also included within the scope of the present invention.

The subject invention also concerns methods for producing a plant that exhibits increased heat stability relative to a wild type plant, wherein a polynucleotide encoding a mutant AGPase small subunit polypeptide of the present invention is introduced into a plant cell and the polypeptide(s) encoded by the polynucleotide(s) is expressed. In one embodiment, the plant cell comprises non-mutant genes encoding wild type AGPase large subunit polypeptide. In another embodiment, the plant cell comprises at least one polynucleotide encoding a mutant AGPase large subunit polypeptide. In a further embodiment, a polynucleotide encoding a mutant AGPase large subunit polypeptide is also introduced into a plant cell along with the polynucleotide encoding the mutant AGPase small subunit polypeptide. In one embodiment, the polynucleotide or polynucleotides is incorporated into the genome of the plant cell and a plant is grown from the plant cell. In a preferred embodiment, the plant grown from the plant cell stably expresses the incorporated polynucleotide or polynucleotides.

The subject invention also concerns oligonucleotide probes and primers, such as polymerase chain reaction (PCR) primers, that can hybridize to a coding or non-coding sequence of a polynucleotide of the present invention. Oligonucleotide probes of the invention can be used in methods for detecting and quantitating nucleic acid sequences encoding a mutant AGPase small subunit polypeptide of the invention. Oligonucleotide primers of the invention can be used in PCR methods and other methods involving nucleic acid amplification. In a preferred embodiment, a probe or primer of the invention can hybridize to a polynucleotide of the invention under stringent conditions. Probes and primers of the invention can optionally comprise a detectable label or reporter molecule, such as fluorescent molecules, enzymes, radioactive moiety (e.g., $^3$H, $^{35}$S, $^{125}$I, etc.), and the like. Probes and primers of the invention can be of any suitable length for the method or assay in which they are being employed. Typically, probes and primers of the invention will be 10 to 500 or more nucleotides in length. Probes and primers that are 10 to 20, 21 to 30, 31 to 40, 41 to 50, 51 to 60, 61 to 70, 71 to 80, 81 to 90, 91 to 100 or more nucleotides in length are contemplated within the scope of the invention. Probes and primers of the invention can have complete (100%) nucleotide sequence identity with the polynucleotide sequence, or the sequence identity can be less than 100%. For example, sequence identity between a probe or primer and a sequence can be 99%, 98%, 97%, 96%, 95%, 90%, 85%, 80%, 75%, 70% or any other percentage sequence identity so long as the probe or primer can hybridize under stringent conditions to a nucleotide sequence of a polynucleotide of the invention. In one embodiment, a probe or primer of the invention has 70% or greater, 75% or greater, 80% or greater, 85% or greater, 90% or greater, or 95% to 100% sequence identity with a nucleotide sequence of SEQ ID NO:1, SEQ ID NO:3, SEQ ID NO:11, SEQ ID NO:12, SEQ ID NO:13, SEQ ID NO:14, SEQ ID NO:15, or SEQ ID NO:16, or the complement thereof.

The subject invention also concerns isolated mutant AGPase small subunit polypeptides. In one embodiment, the mutant AGPase small subunit polypeptide is an AGPase small subunit polypeptide of *Zea mays*. In a specific embodiment, an AGPase small subunit polypeptide of the invention has an amino acid sequence as shown in SEQ ID NO:2, SEQ ID NO:4, SEQ ID NO:5, SEQ ID NO:6, SEQ ID NO:7, SEQ ID NO:8, SEQ ID NO:9, SEQ ID NO:10, SEQ ID NO:21, SEQ ID NO:22, SEQ ID NO:23, SEQ ID NO:24, or SEQ ID NO:25, or functional fragment or variant thereof. An AGPase small subunit polypeptide or enzyme of the invention can be purified using standard techniques known in the art. In one embodiment, a polynucleotide of the invention encoding an AGPase small subunit polypeptide is incorporated into a microorganism, such as *E. coli*, and the AGPase small subunit polypeptide expressed in the microorganism and then isolated therefrom.

In certain embodiments, polypeptides of the invention, and functional peptide fragments thereof, can be used to generate antibodies that bind specifically to a polypeptide of the invention, and such antibodies are contemplated within the scope of the invention. The antibodies of the invention can be polyclonal or monoclonal and can be produced and isolated using standard methods known in the art.

Polypeptide fragments according to the subject invention typically comprise a contiguous span of about or at least 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, or 475 amino acids of SEQ ID NO:2, SEQ ID NO:4, SEQ ID NO:5, SEQ ID NO:6, SEQ ID NO:7, SEQ ID NO:8, SEQ ID NO:9, SEQ ID NO:10.

In certain embodiments, polypeptide fragments of the subject invention can be any integer in length from at least about 25 consecutive amino acids to 1 amino acid less than the full-length sequence, such as those shown in SEQ ID NO:2, SEQ ID NO:4, SEQ ID NO:5, SEQ ID NO:6, SEQ ID NO:7, SEQ ID NO:8, SEQ ID NO:9, or SEQ ID NO:10. Thus, for SEQ ID NO:2, SEQ ID NO:4, SEQ ID NO:5, SEQ ID NO:6, SEQ ID NO:7, SEQ ID NO:8, SEQ ID NO:9, or SEQ ID NO:10, a polypeptide fragment can be any integer of consecutive amino acids from about 25 to 475 amino acids. The term "integer" is used herein in its mathematical sense and thus representative integers include: 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, and/or 475.

Each polypeptide fragment of the subject invention can also be described in terms of its N-terminal and C-terminal positions. For example, combinations of N-terminal to C-terminal fragments of about 25 contiguous amino acids to 1 amino acid less than the full length polypeptide, such as those of SEQ ID NO:2, SEQ ID NO:4, SEQ ID NO:5, SEQ ID NO:6, SEQ ID NO:7, SEQ ID NO:8, SEQ ID NO:9, or SEQ ID NO:10 are included in the present invention. Thus, using SEQ ID NO:2, SEQ ID NO:4, SEQ ID NO:5, SEQ ID NO:6, SEQ ID NO:7, SEQ ID NO:8, SEQ ID NO:9, or SEQ ID NO:10 as an example, a 25 consecutive amino acid fragment could correspond to amino acids of SEQ ID NO:2, SEQ ID NO:4, SEQ ID NO:5, SEQ ID NO:6, SEQ ID NO:7, SEQ ID NO:8, SEQ ID NO:9, or SEQ ID NO:10 selected from the group consisting of 1-25, 2-26, 3-27, 4-28, 5-29, 6-30, 7-31, 8-32, 9-33, 10-34, 11-35, 12-36, 13-37, 14-38, 15-39, 16-40, 17-41, 18-42, 19-43, 20-44, 21-45, 22-46, 23-47, 24-48, 25-49, 26-50, 27-51, 28-52, 29-53, 30-54, 31-55, 32-56, 33-57, 34-58, 35-59, 36-60, 37-61, 38-62, 39-63, 40-64, 41-65, 42-66, 43-67, 44-68, 45-69, 46-70, 47-71, 48-72, 49-73, 50-74, 51-75, 52-76, 53-77, 54-78, 55-79, 56-80, 57-81, 58-82, 59-83, 60-84, 61-85, 62-86, 63-87, 64-88, 65-89, 66-90, 67-91, 68-92, 69-93, 70-94, 71-95, 72-96, 73-97, 74-98, 75-99, 76-100, 77-101, 78-102, 79-103, 80-104, 81-105, 82-106, 83-107, 84-108, 85-109, 86-110, 87-111, 88, 112, 89-113, 90-114, 91-115, 92-116, 93-117, 94-118, 95-119, 96-120, 97-121, 98-122, 99-123, 100-124, 101-125, 102-126, 103-127, 104-128, 105-129, 106-130, 107-131, 108-132, 109-133, 110-134, 111-135, 112-136, 113-137, 114-138, 115-139, 116-140, 117-141, 118-142, 119-143, 120-144, 121-145, 122-146, 123-147, 124-148, 125-149, 126-150, 127-151, 128-152, 129-153, 130-154, 131-155, 132-156, 133-157, 134-158, 135-159, 136-160, 137-161, 138-162, 139-163, 140-164, 141-165, 142-166, 143-167, 144-168, 145-169, 146-170, 147-171, 148-172, 149-173, 150-174, 151-175, 152-176, 153-177, 154-178, 155-179, 156-180, 157-181, 158-182, 159-183, 160-184, 161-185, 162-186, 163-187, 164-188, 165-189, 166-190, 167-191, 168-192, 169-193, 170-194, 171-195, 172-196, 173-197, 174-198, 175-199, 176-200, 177-201, 178-202, 179-203, 180-204, 181-205, 182-206, 183-207, 184-208, 185-209, 186-210, 187-211, 188-212, 189-213, 190-214, 191-215, 192-216, 193-217, 194-218, 195-219, 196-220, 197-221, 198-222, 199-223, 200-224, 201-225, 202-226, 203-227, 204-228, 205-229, 206-230, 207-231, 208-232, 209-233, 210-234, 211-235, 212-236, 213-237, 214-238, 215-239, 216-240, 217-241, 218-242, 219-243, 220-244, 221-245, 222-246, 223-247, 224-248, 225-249, 226-250, 227-251, 228-252, 229-253, 230-254, 231-255, 232-256, 233-257, 234-258, 235-259, 236-260, 237-261, 238-262, 239-263, 240-264, 241-265, 242-266, 243-267, 244-268, 245-269, 246-270, 247-271, 248-272, 249-273, 250-274, 251-275, 252-276, 253-277, 254-278, 255-279, 256-280, 257-281, 258-282, 259-283, 260-284, 261-285, 262-286, 263-287, 264-288, 265-289, 266-290, 267-291, 268-292, 269-293, 270-294, 271-295, 272-296, 273-297, 274-298, 275-299, 276-300, 277-301, 278-302, 279-303, 280-304, 281-305, 282-306, 283-307, 284-308, 285-309, 286-310, 287-311, 288-312, 289-313, 290-314, 291-315, 292-316, 293-317, 294-318, 295-319, 296-320, 297-321, 298-322, 299-323, 300-324, 301-325, 302-326, 303-327, 304-328, 305-329, 306-330, 307-331, 308-332, 309-333, 310-334, 311-335, 312-336, 313-337, 314-338, 315-339, 316-340, 317-341, 318-342, 319-343, 320-344, 321-345, 322-346, 323-347, 324-348, 325-349, 326-350, 327-351, 328-352, 329-353, 330-354, 331-355, 332-356, 333-357, 334-358, 335-359, 336-360, 337-361, 338-362, 339-363, 340-364, 341-365, 342-366, 343-367, 344-368, 345-369, 346-370, 347-371, 348-372, 349-373, 350-374, 351-375, 352-376, 353-377, 354-378, 355-379, 356-380, 357-381, 358-382, 359-383, 360-384, 361-385, 362-386, 363-387, 364-388, 365-389, 366-390, 367-391, 368-392, 369-393, 370-394, 371-395, 372-396, 373-397, 374-398, 375-399, 376-400, 377-401, 378-402, 379-403, 380-404, 381-405, 382-406, 383-407, 384-408, 385-409, 386-410, 387-411, 388-412, 389-413, 390-414, 391-415, 392-416, 393-417, 394-418, 395-419, 396-420, 397-421, 398-422, 399-423, 400-424, 401-425, 402-426, 403-427, 404-428, 405-429, 406-430, 407-431, 408-432, 409-433, 410-434, 411-435, 412-436, 413-437, 414-438, 415-439, 416-440, 417-441, 418-442, 419-443, 420-444, 421-445, 422-446, 423-447, 424-448, 425-449, 426-450, 427-451, 428-452, 429-453, 430-454, 431-455, 432-456, 433-457, 434-458, 435-459, 436-460, 437-461, 438-462, 439-463, 440-464, 441-465, 442-466, 443-467, 444-468, 445-469, 446-470, 447-471, 448-472, 449-473, 450-474, and/or 451-475. Similarly, the amino acids corresponding to all other fragments of sizes between 26 consecutive amino acids and 474 (or 475) consecutive amino acids of SEQ ID NO:2, SEQ ID NO:4, SEQ ID NO:5, SEQ ID NO:6, SEQ ID NO:7, SEQ ID NO:8, SEQ ID NO:9, or SEQ ID NO:10 are included in the present invention and can also be immediately envisaged based on these examples. Therefore, additional examples, illustrating various fragments of the polypeptides of SEQ ID NO:2, SEQ ID NO:4, SEQ ID NO:5, SEQ ID NO:6, SEQ ID NO:7, SEQ ID NO:8, SEQ ID NO:9, or SEQ ID NO:10 are not individually listed herein in order to avoid unnecessarily lengthening the specification.

Polypeptide fragments comprising: 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, and 474 (or 475) consecutive amino acids of SEQ ID NO:2, SEQ ID NO:4, SEQ ID NO:5, SEQ ID NO:6, SEQ ID NO:7, SEQ ID NO:8, SEQ ID NO:9, or SEQ ID NO:10 may alternatively be described by the formula "n to c" (inclusive), where "n" equals the N-terminal amino acid position and "c" equals the C-terminal amino acid position of the polypeptide. In this embodiment of the invention, "n" is an integer having a lower limit of 1 and an upper limit of the total number of amino acids of the full length polypeptide minus 24 (e.g., 475-24=451 for SEQ ID NO:2, SEQ ID NO:4, SEQ ID NO:5, or SEQ ID NO:8; 476-24=452 for SEQ ID NO:6, SEQ ID NO:7, SEQ ID NO:9, or SEQ ID NO:10). "c" is an integer between 25 and the number of amino acids of the full length polypeptide sequence (475 for SEQ ID NO:2, SEQ ID NO:4, SEQ ID NO:5, or SEQ ID NO:8; 476 for SEQ ID NO:6, SEQ ID NO:7, SEQ ID NO:9, or SEQ ID NO:10) and "n" is an integer smaller than "c" by at least 24. Therefore, for SEQ ID NO:2, SEQ ID NO:4, SEQ ID NO:5, SEQ ID NO:6, SEQ ID NO:7, SEQ ID NO:8, SEQ ID NO:9, or SEQ ID NO:10, "n" is any integer selected from the list consisting of: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, and 451 (or 452); and "c" is any integer selected from the group consisting of: 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, and 475 (or 476) provided that "n" is a value less than "c" by at least 24. Every combination of "n" and "c" positions are included as specific embodiments of polypeptide fragments of the invention. All ranges used to describe any polypeptide fragment embodiment of the present invention are inclusive unless specifically set forth otherwise.

Fragments of a mutant AGPase small subunit polypeptide of the invention or an AGPase large subunit polypeptide, as described herein, can be obtained by cleaving the polypeptides of the invention with a proteolytic enzyme (such as trypsin, chymotrypsin, or collagenase) or with a chemical reagent, such as cyanogen bromide (CNBr). Alternatively, polypeptide fragments can be generated in a highly acidic environment, for example at pH 2.5. Polypeptide fragments can also be prepared by chemical synthesis or using host cells transformed with an expression vector comprising a polynucleotide encoding a fragment of an AGPase large subunit polypeptide or a fragment of a mutant AGPase small subunit polypeptide of the invention, for example, a mutant polypeptide that is a fragment of the amino acid sequence shown in SEQ ID NO:2, SEQ ID NO:4, SEQ ID NO:5, SEQ ID NO:6, SEQ ID NO:7, SEQ ID NO:8, SEQ ID NO:9, SEQ ID NO:10, SEQ ID NO:21, SEQ ID NO:22, SEQ ID NO:23, SEQ ID NO:24, or SEQ ID NO:25. Fragments of a mutant large or small subunit AGPase polypeptide of the invention also contemplated herein include fragments of the polypeptide wherein all or a part of a transit or signal sequence of the polypeptide is removed.

The subject invention also concerns cells transformed with a polynucleotide of the present invention encoding a mutant AGPase small subunit polypeptide of the invention. In one embodiment, the cell is transformed with a polynucleotide sequence comprising a sequence encoding the amino acid sequence shown in SEQ ID NO:2, SEQ ID NO:4, SEQ ID NO:5, SEQ ID NO:6, SEQ ID NO:7, SEQ ID NO:8, SEQ ID NO:9, SEQ ID NO:10, SEQ ID NO:21, SEQ ID NO:22, SEQ ID NO:23, SEQ'ID NO:24, or SEQ ID NO:25, or a functional fragment or variant thereof. In a specific embodiment, the cell is transformed with a polynucleotide sequence shown in SEQ ID NO:1, SEQ ID NO:3, SEQ ID NO:11, SEQ ID NO:12, SEQ ID NO:13, SEQ ID NO:14, SEQ ID NO:15, or SEQ ID NO:16, or a sequence encoding a functional fragment or variant of SEQ ID NO:2, SEQ ID NO:4, SEQ ID NO:5, SEQ ID NO:6, SEQ ID NO:7, SEQ ID NO:8, SEQ ID NO:9, SEQ ID NO:10, SEQ ID NO:21, SEQ ID NO:22, SEQ ID NO:23, SEQ ID NO:24, or SEQ ID NO:25. In one embodiment, a cell is also transformed with a polynucleotide encoding a mutant AGPase large subunit polypeptide as described herein. In one embodiment, the polynucleotide sequence is provided in an expression construct of the invention. The transformed cell can be a prokaryotic cell, for example, a bacterial cell such as *E. coli* or *B. subtilis*, or the transformed cell can be a eukaryotic cell, for example, a plant cell, including protoplasts, or an animal cell. Plant cells include, but are not limited to, dicotyledonous, monocotyledonous, and conifer cells. In one embodiment, the plant cell is a cell from a *Zea mays* plant. Animal cells include human cells, mammalian cells, avian cells, and insect cells. Mammalian cells include, but are not limited to, COS, 3T3, and CHO cells.

The subject invention also concerns methods for increasing starch synthesis in a plant or plant tissue (such as a plant seed or endosperm tissue). In one embodiment, a method of the invention comprises introducing one or more polynucleotides of the present invention into a plant. In certain embodiments, the polynucleotides introduced into the plant encode one or more polypeptides comprising the amino acid sequence shown in any of SEQ ID NO:2, SEQ ID NO:4, SEQ ID NO:5, SEQ ID NO:6, SEQ ID NO:7, SEQ ID NO:8, SEQ ID NO:9, SEQ ID NO:10, SEQ ID NO:21, SEQ ID NO:22, SEQ ID NO:23, SEQ ID NO:24, or SEQ ID NO:25, or a fragment or variant thereof. In a specific embodiment, the polynucleotide comprises the nucleotide sequence shown in SEQ ID NO:1, or SEQ ID NO:3, or a fragment or variant thereof. In further specific embodiments, the polynucleotide comprises the nucleotide sequences shown in SEQ ID NO:11, SEQ ID NO:12, SEQ ID NO:13, SEQ ID NO:14, SEQ ID NO:15, or SEQ ID NO:16, or a fragment or variant thereof. In one embodiment, the polynucleotide is stably incorporated into the genome of the plant or plant tissue. The polynucleotide can comprise regulatory elements, such as a promoter and/or enhancer sequences, that provide for increased expression of the polynucleotide and/or the polypeptide encoded thereby. In a specific embodiment, the promoter sequence is one that provides for constitutive or tissue-specific (e.g., endosperm) expression. Plants or plant tissues containing the polynucleotide, or progeny of the plants, optionally can be screened for increased expression of a polynucleotide or polypeptide of the invention. In one embodiment, multiple copies of one or more polynucleotides of the invention are introduced into a plant or plant tissue and stably incorporated into the genome of the plant. In one embodiment, a polynucleotide of the invention is provided in an expression construct as described herein.

Single letter amino acid abbreviations are defined in Table 2.

TABLE 2

| Letter Symbol | Amino Acid |
| --- | --- |
| A | Alanine |
| B | Asparagine or aspartic acid |
| C | Cysteine |
| D | Aspartic Acid |
| E | Glutamic Acid |
| F | Phenylalanine |
| G | Glycine |
| H | Histidine |
| I | Isoleucine |

TABLE 2-continued

| Letter Symbol | Amino Acid |
| --- | --- |
| K | Lysine |
| L | Leucine |
| M | Methionine |
| N | Asparagine |
| P | Proline |
| Q | Glutamine |
| R | Arginine |
| S | Serine |
| T | Threonine |
| V | Valine |
| W | Tryptophan |
| Y | Tyrosine |
| Z | Glutamine or glutamic acid |

MATERIALS AND METHODS

Random Mutagenesis

Mutations were introduced into Sh2 and Bt2 by PCR random mutagenesis (GeneMorph II EZClone Domain Mutagenesis Kit, Stratagene). A mixture of non-biased, error-prone DNA polymerases was used to introduce point mutations. Wildtype Sh2 and Bt2 coding sequences in pMONcSh2 and pMONcBt2 (Giroux et al., 1996) respectively were used as templates for PCR. Two pairs of primers (Sh2: 5'-GAAG-GAGATATATCCATGG-3' (SEQ ID NO:17), 5'-GGATC-CCCGGGTACCGAGCTC-3' (SEQ ID NO:18) Bt2: 5'-GAAGGAGATATATCCATGG-3' (SEQ ID NO:19), 5'-GTTGATATCTGAATTCGAGCTC-3' (SEQ ID NO:20)) flanking Sh2 and Bt2 were used for error-prone PCR. Mutant Sh2 clones produced by PCR were subcloned into vector pMONcSh2 according to Stratagene protocols. pMONcSh2 was then used to transform *E. coli* strain AC70R1-504 that contained wildtype Bt2 in the compatible vector pMONcBt2. Mutant Bt2 clones produced by PCR were subcloned into vector pMONcBt2. pMONcBt2 was then used to transform *E. coli* strain AC70R1-504 that contained wildtype Sh2 in the compatible vector pMONcSh2.

Bacterial Expression System

A bacterial expression system (Iglesias et al., 1993) allowed us to randomly mutagenize maize endosperm AGPase genes and score AGPase activity in a fast and efficient way by exposing plates to iodine vapors as described below. The *E. coli* system is ideal for studying plant AGPases for a number of reasons discussed in Georgelis et al. (2007).

Glycogen Detection

Glycogen synthesis was detected by production of brown staining colonies following exposure to iodine vapors. *E. coli* cells were grown on Kornberg media in the presence of 75 µg/mL spectinomycin, 50 µg/mL kanamycin and 1% w/v glucose for 16 h at 37° C. (Govons et al., 1969). The colonies were exposed to iodine vapors for 1 min. Colonies with inactive AGPase produced no color following exposure to iodine vapors while active AGPase produced glycogen and, in turn, brown staining with iodine. AGPase variants staining darker than wildtype were selected for further study.

Glycogen Quantitation

Glycogen quantitation was performed by phenol reaction (Hanson and Phillips, 1981). In brief, glycogen was extracted from 1.6 ml of *E. coli* cells ($OD_{600}$=2.0) grown in LB containing 2% w/v glucose by boiling for 3 hours in 50% w/v KOH. Glycogen was then precipitated by adding ethanol to 70% v/v and centrifuging at 10000×g for 10 min. After pellet drying, 200 µl de-ionized water, 200 µl of 5% w/v phenol and 1 mL of concentrated sulfuric acid were added. Glycogen was estimated by the absorbance at 488 nm.

DNA Sequencing

Sh2 and Bt2 mutants that produced enhanced glycogen were double-pass sequenced by the Genome Sequencing Services Laboratory (GSSL) of the Interdisciplinary Center for Biotechnology Research at the University of Florida. Data analysis was performed by Bioedit software (Hall, 1999).

Purification of Maize Endosperm AGPase from AC70R1-504 *E. coli* Cells

AC70R1-504 *E. coli* cells expressing maize endosperm AGPase were grown in 2 L of Luria-Broth (LB) medium in the presence of 75 µg/mL spectinomycin, 50 µg/mL kanamycin and 2% w/v glucose for 16 h at 37° C. with shaking. At OD600=0.6, 0.2 mM isopropyl-beta-D-thiogalactoside (IPTG) and 0.02 mg/mL nalidixic acid were added to induce protein expression. The cultures were immediately moved to room temperature and grown for 4 h with shaking. The following steps were conducted at 4° C. Cells were harvested by centrifuging at 3000×g and the pellet was resuspended in 16 mL of buffer A (50 mM $KH_2PO_4$ pH 7.0, 5 mM $MgCl_2$, 0.5 mM EDTA) and protease inhibitors (1 µg/mL pepstatin, 0.1 mM PMSF, 10 µg/mL chymostatin, and 1 mM benzamidine). The cells were lysed with a French press and centrifuged at 26000×g. The protein concentration of the supernatant was adjusted to 30 mg/mL by adding buffer A. Three tenths of volume of 1% protamine sulfate were added and the mixture stirred on ice for 20 min and then centrifuged at 26000×g for 20 min. The supernatant was brought to 45% saturation with ammonium sulfate, stirred on ice for 20 min and centrifuged at 26000×g for 20 min. The pellet was re-suspended in 2-2.5 mL of buffer A. The mixture was passed through a strong anion exchange column (macro-prep High Q support, Biorad), and an Econo-pac hydroxyapatite cartridge (Biorad) as described by Boehlein et al. (2005). AGPase was desalted by using Zeba Micro Desalt Spin Columns (Pierce) before assaying. AGPase was exchanged into 50 mM HEPES, 5 mM $MgCl_2$, 0.5 mM EDTA and 0.5 mg/mL BSA (for stability).

Kinetic Characterization of AGPase

The forward direction of the reaction was used (G-1-P+ATP→ADP-glucose+PPi) for estimating $k_{cat}$, $K_m$ for ATP and G-1-P, and affinities for 3-PGA and Pi. More specifically, 0.04-0.06 µg of purified AGPase was assayed for specific activity in a total volume of 200 µl of 50 mM HEPES pH 7.4, 15 mM $MgCl_2$, 1.0 mM ATP, and 2.0 mM G-1-P at 37° C. for 10 min. For determining $K_m$s for ATP and G-1-P and $K_a$ for 3-PGA, varying amounts of ATP, G-1-P and 3-PGA respectively. $K_i$ for Pi was estimated by adding various amounts of Pi, 1 mM ATP, 2 mM G-1-P, and 2.5 mM 3-PGA were used. The reaction was stopped by boiling for 2 min. PPi was estimated by coupling the reaction to a reduction in NADH concentration using 300 µl of coupling reagent. The coupling reagent contained 25 mM imidazole pH 7.4, 4 mM $MgCl_2$, 1 mM EDTA, 0.2 mM NADH, 0.725U aldolase, 0.4U triose phosphate isomerase, 0.6U glycerophosphate dehydrogenase, 1 mM fructose 6-phosphate and 0.8 µg of pyrophosphate dependent phosphofructokinase (PPi-PFK). All the enzymes were purchased from Sigma except for PPi-PFK which was produced and purified according to Deng et al. 1999 with some modifications (Boehlein and Hannah, unpublished data). NADH concentration was estimated by absorbance at 340 nm. PPi concentration was calculated by a standard curve developed by using various amounts of PPi instead of AGPase. The amount of PPi produced by AGPase was linear with time and enzyme concentration. The kinetic constants of AGPase were calculated by Prism 4.0 (Graph Pad, San Diego Calif.).

Measuring AGPase Specific Activity from Crude or Partially Purified Protein Extracts AC70R1-504 E. coli cells expressing maize endosperm AGPase were grown in 2 L of Luria-Broth (LB) medium in the presence of 75 µg/mL spectinomycin, 50 µg/mL kanamycin and 2% w/v glucose at 37° C. with shaking until OD600=2.0. Gene expression was not induced. The following steps were conducted at 4° C. Cells were harvested by centrifuging at 3000×g and the pellet was resuspended in 16 mL of buffer A (50 mM $KH_2PO_4$ pH 7.0, 5 mM $MgCl_2$, 0.5 mM EDTA) and protease inhibitors (1 µg/mL pepstatin, 0.1 mM PMSF, 10 µg/mL chymostatin, and 1 mM benzamidine). The cells were lysed with a French press and centrifuged at 26000×g. AGPase activity of the crude extract was measured from the supernatant stored at −80° C. The rest of the supernatant was partially purified through protamine sulfate and ammonium sulfate as described above. Protein extracts were desalted as described by Boehlein et al. (2005) before assay and were exchanged into 50 mM HEPES, 5 mM $MgCl_2$, and 0.5 mM EDTA. AGPase specific activity was monitored in the reverse direction (ADP-glucose+PPi→G-1-P+ATP) using saturating amounts of substrates and activator as described by Boehlein et al. (2005).

Determining Heat Stability of AGPase

AGPase was purified as described above. AGPase was further diluted 1/100 (v/v) in 50 mM HEPES, 5 mM $MgCl_2$, 0.5 mM EDTA and 0.5 mg/mL BSA and heat treated at 42 or 53° C. for various times, and then cooled on ice. The activity remaining after heat treatment was monitored in the forward and reverse direction by using saturating amounts of ATP, G-1-P and 3-PGA. The data were plotted as log of percentage of remaining activity versus time of heat treatment. The inactivation constant $t_{1/2}$ was calculated from the formula $t_{1/2}=0.693/(-2.3*slope)$.

Qualitative Determination of the AGPase Purity

The purity of AGPase was monitored in the following way. Six µg of AGPase were diluted 1:1 in denaturing solution (100 mM Tris-Cl pH 6.8, 4% SDS, and 8 mM DTT), heated at 95° C. for 5 min, electrophoresed on a 5% SDS polyacrylamide gel at 150V for 1 h and visualized by staining with Coomassie Brilliant Blue (Laemmli, 1970).

Protein Blot Analysis of Crude Extracts

Samples were vacuum blotted onto a PVDF membrane (Biorad) by using Hybri-Dot blot apparatus (Life Technologies). The PVDF membrane had been pre-soaked in methanol for 5 min and then in transfer buffer [20% (v/v) methanol, 0.303% (w/v) Tris and 1.44% (w/v) glycine] for 10 min. The membrane was incubated with blocking buffer [0.8% (w/v) NaCl, 0.02% (w/v) KCl, 0.144% (w/v) $Na_2HPO_4$, 0.024% (w/v) $KH_2PO_4$, 5% (w/v) bovine serum albumin (BSA), and 0.05% (v/v) Tween-20] for 1 h with constant shaking. The blot was incubated with blocking buffer containing 1:10000 (v/v) of monoclonal antibody against BT2 (kindly provided by Sue Boehlein) for 1 h with shaking. Then, the blot was washed 3×10 min with washing buffer (blocking buffer— BSA) with constant shaking. The blot was then incubated with a 1:60000 dilution of goat anti-mouse secondary antibody conjugated with horseradish peroxidase (Pierce) for 45 min. Finally the blot was washed 3×10 min. Proteins were visualized using an enhanced chemiluminescent substrate kit (Pierce).

3D Modeling

BT2 monomer structure was modeled after the potato small unit in the recently-published three dimensional structure of the potato tuber homotetrameric AGPase (RCSB Protein Data Bank #:1YP2). Homology modeling was done by using SWISS MODEL (Peitsch, 1995; Guex and Peitsch, 1997; Schwede et al. 2003; Kopp and Schwede, 2004; Arnold et al, 2006). Amino acid 462 (Thr or Ile) contacting residues were determined by using Jmol, an open-source Java viewer for chemical structures in 3D.

Yeast Two Hybrid

Yeast transformations and a β-galactosidase assay were conducted as described by Greene and Hannah (1998b). The only modification was the use of pGBKT7 and pGADT7 as vectors for the bait and the prey respectively. pGBKT7-53 and pGADT7-T plasmids were used as a positive control.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

EXAMPLE 1

A mutant Bt2 library was created by error-prone PCR. The mutational load was ~2 non-synonymous mutations per clone (Georgelis et al. 2007). The mutants were expressed in E. coli along with a wildtype Sh2 gene. Approximately 50,000 colonies were screened for glycogen production. Ten dark staining colonies were picked. The two darkest staining Bt2 mutants were sequenced. Both had the same non-synonymous mutation resulting in a change of amino acid 462 from threonine to isoleucine (TI). The threonine in that position is absolutely conserved among the higher plant small subunits (data not shown). BT2-TI/SH2 (BT2 comprising the TI mutation and complexed with SH2) produced more glycogen than did BT2/SH2 (FIG. 1). Cells expressing BT2-TI and BT2, as homotetramers, did not produce detectable amounts of glycogen (FIG. 1). This indicates that the amount of E. coli-synthesized glycogen depends exclusively on the complex of BT2-TI or BT2 with SH2.

A dot-blot of the crude extracts from cells expressing BT2/SH2 and BT2-TI/SH2 indicated that BT2-TI is found in higher amounts in E. coli (FIGS. 2A-2B). While AGPase activity levels of crude extracts from non-induced cells expressing BT2/SH2 and BT2-TI/SH2 were too low to detect, the partially purified extract from BT2-TI/SH2 had 20 times more activity than did the partially purified extract from BT2/SH2 (FIG. 3). The possibility that BT2-TI/SH2 produced more protein and activity because of more efficient transcription/translation is unlikely since the codons ACA (T) to ATA (I) are used with the same frequency in E. coli (6.1 and 5.0% respectively) (Nakamura et al., 2000). This suggests that the higher amount of protein and activity in BT2-TI/SH2 cells is due to increased stability of the AGPase.

Figure 4:
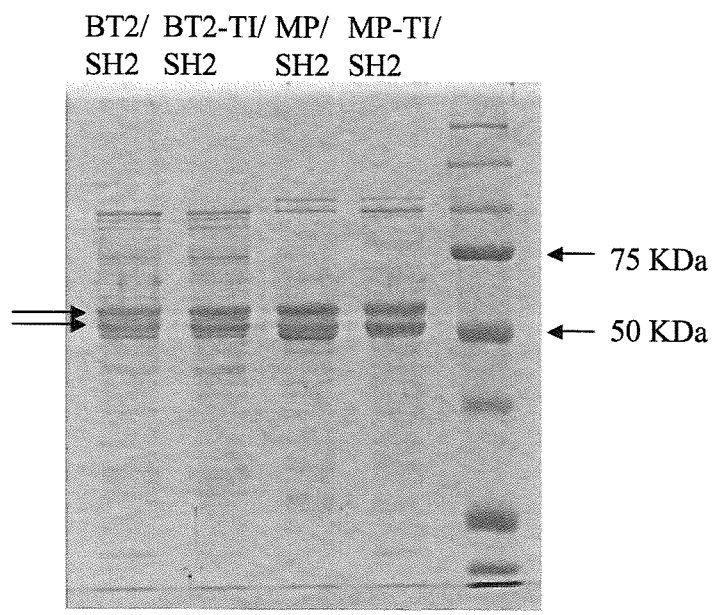
FIG. 4 shows purification of AGPase. SDS-PAGE of purified recombinant BT2/SH2, TI/SH2, MP/SH2, and MP-TI/SH2. Precision Plus Protein All Blue Standard from Biorad was used as a marker. The upper arrow on the left points to the large subunit. The lower arrow on the left points to the small subunit.
Figure 5A:
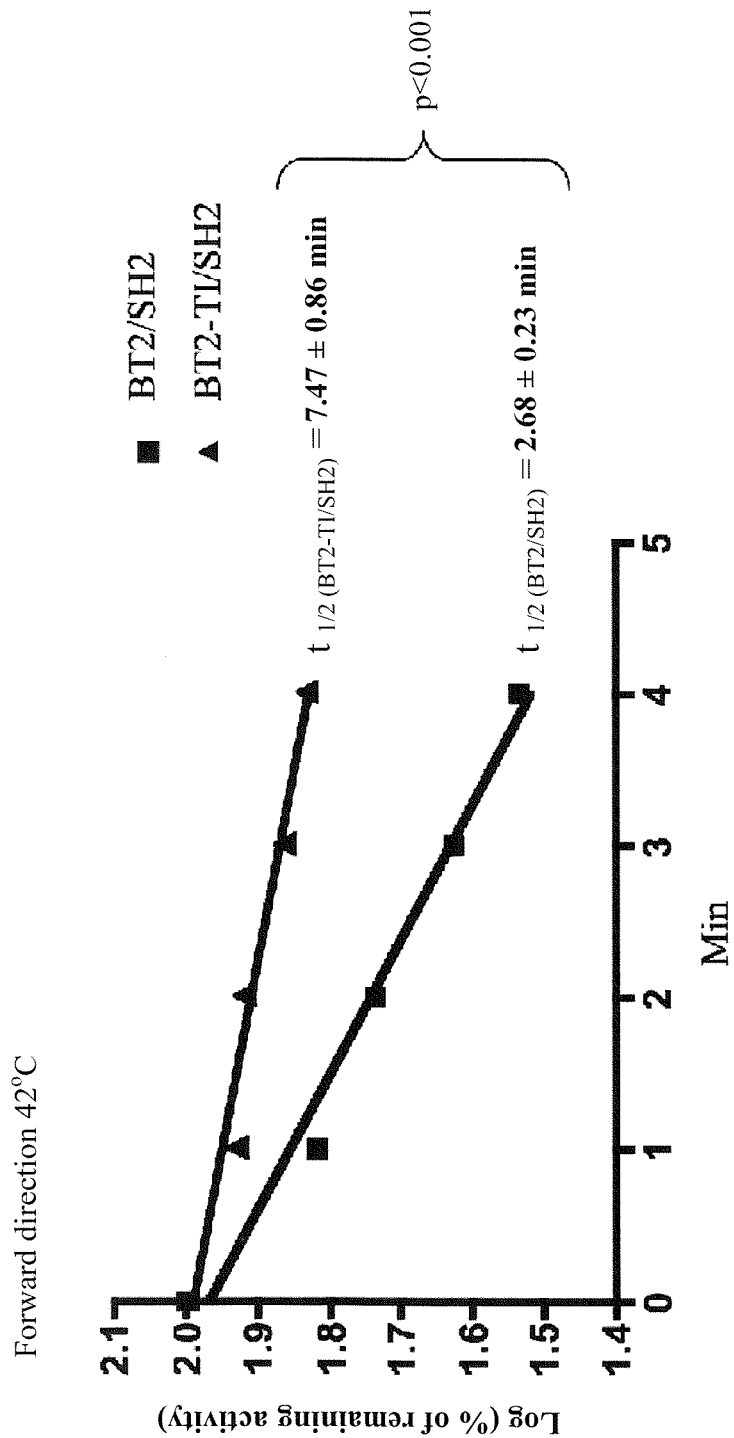
FIGS. 5A and 5B show heat stability of purified BT2/SH2, BT2-TI/SH2, and MP/SH2. The half-life ($T_{1/2}$) of each AGPase is expressed as mean±standard error. The p-values are estimated by an F-test implemented by Prizm (Graph pad, San Diego Calif.).
Figure 5B:
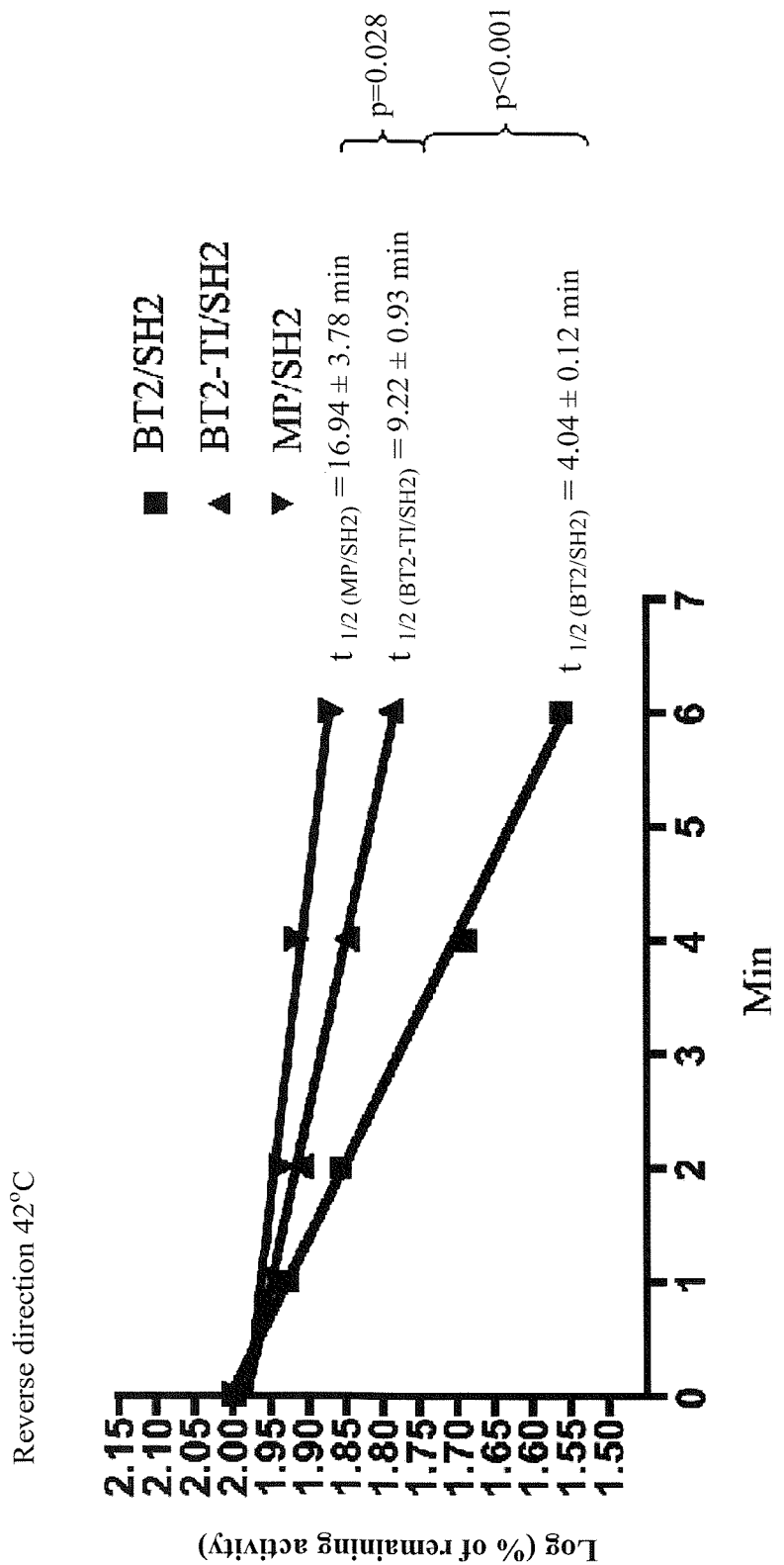

To determine the kinetic properties and heat stability of BT2-TI/SH2 and decipher the cause of enhanced glycogen synthesis in E. coli, recombinant BT2-TI/SH2 and BT2/SH2 AGPases were purified (FIG. 4). The kinetic properties of BT2-TI/SH2, as summarized in Table 3, show that the $K_m$ for G-1-P and ATP, $K_a$ for 3-PGA and $K_i$ for Pi were indistinguishable from BT2/SH2. Surprisingly, the $k_{cat}$ of BT2-TI is 30% lower than the $k_{cat}$ of BT2/SH2. These kinetic properties then cannot account for the darker staining of BT2-TI/SH2 in E. coli. However, BT2-TI/SH2 is clearly more heat-stable than BT2/SH2 (FIGS. 5A-5B). These results strongly suggest that the high heat stability of BT2-TI/SH2 accounts for the enhanced amount of glycogen in E. coli.

MP is a small subunit variant that can lead to agronomic gain. Some of its features include increased activity in the absence of the activator 3-PGA, increased affinity for 3-PGA, decreased affinity for Pi (Table 3) and elevated heat stability compared to BT2/SH2 (FIG. 3) (Cross et al., 2004; Boehlein et al., 2005). Since BT2-TI/SH2 was not as heat-stable as MP/SH2 (FIG. 3), the amino acid change of TI was introduced into MP in an effort to further increase the heat stability of MP (MP-TI).

Figure 6A:
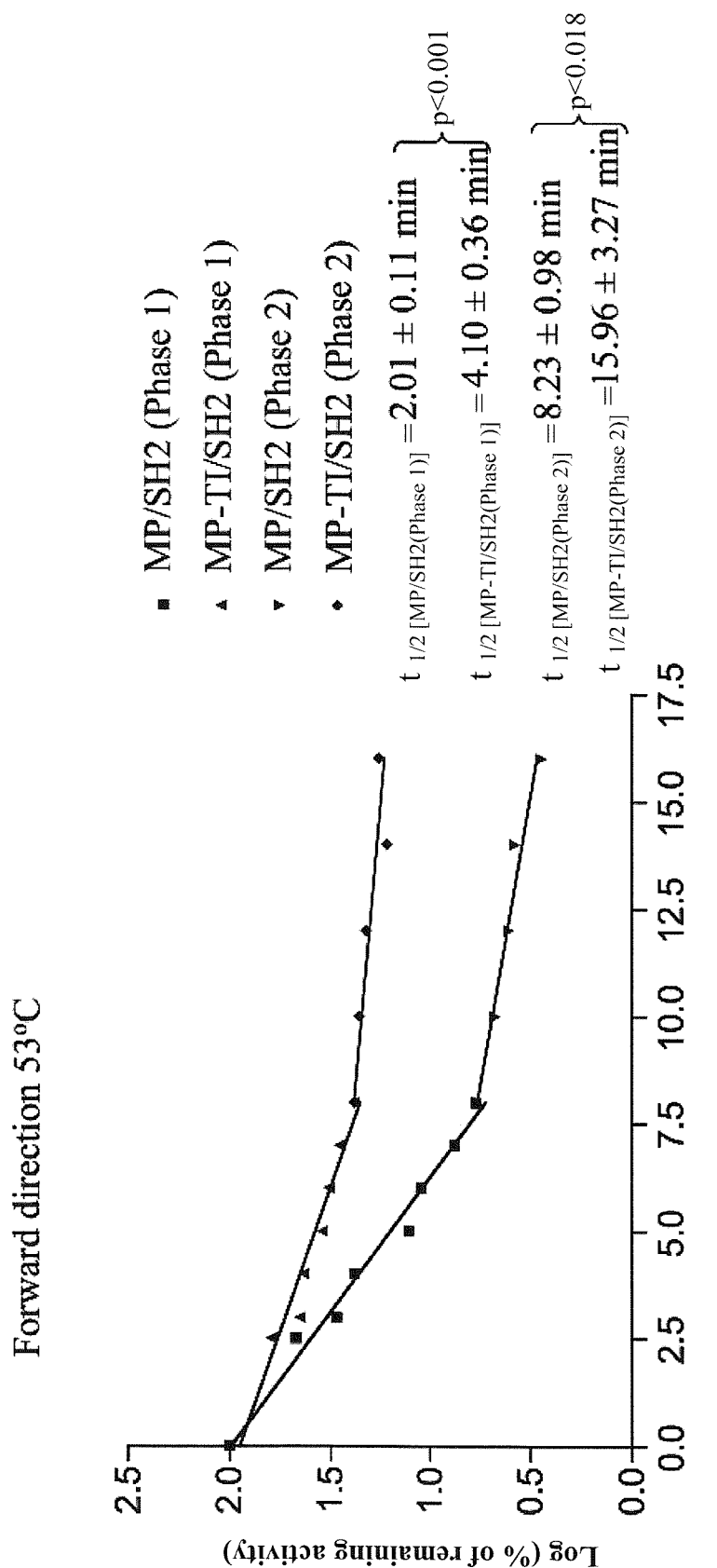
FIGS. 6A and 6B show heat stability of purified MP/SH2 and MP-TI/SH2. The half-life ($T_{1/2}$) of each AGPase is expressed as mean±standard error. The p-values are estimated by an F-test implemented by Prizm (Graph pad, San Diego Calif.).
Figure 6B:
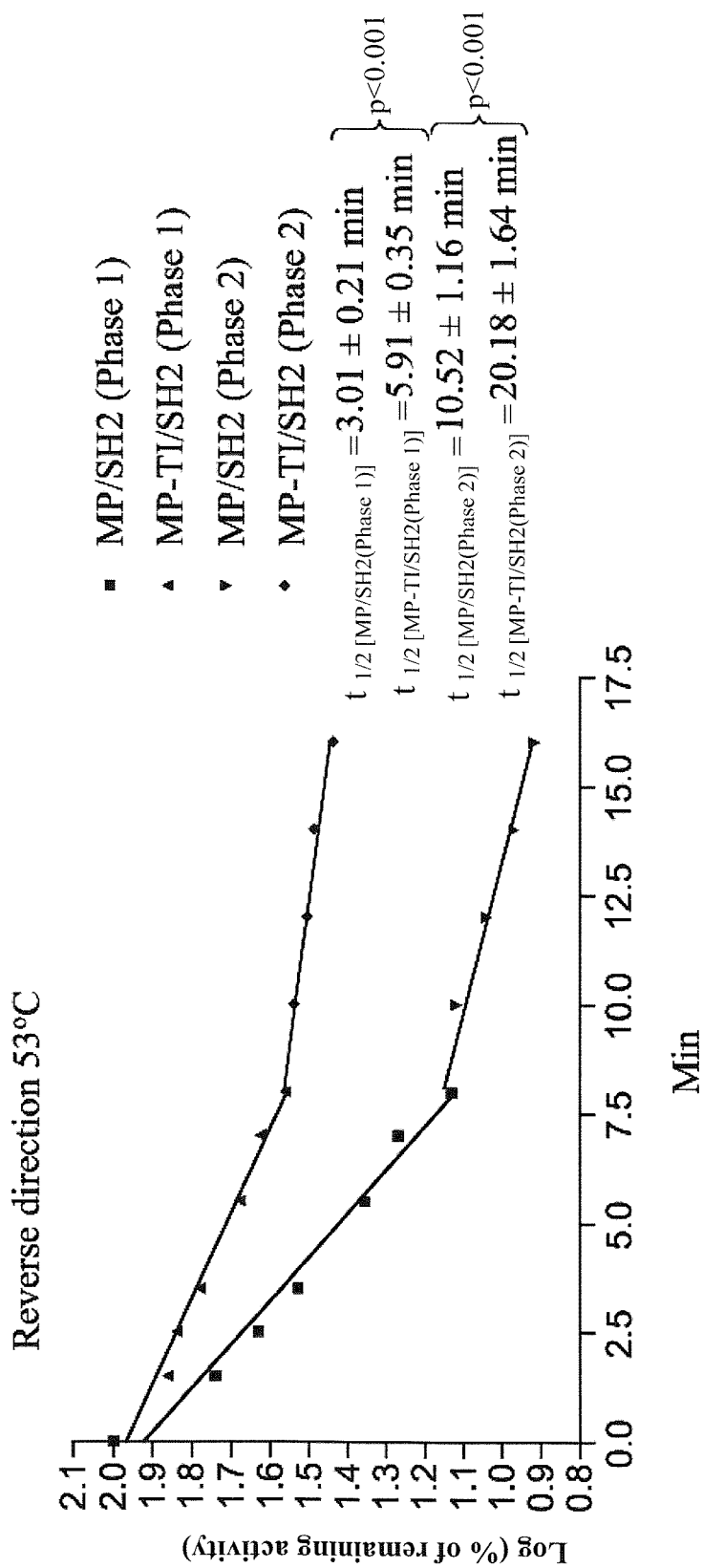

Cells expressing MP-TI/SH2 (MP having the TI mutation and complexed with SH2) produced the same amount of glycogen as cells expressing MP/SH2 (FIG. 1). However, greater amounts of the MP-TI protein relative to BT2 were found in crude extracts of E. coli expressing the two proteins with SH2 (FIGS. 2A-2B). The activity of the crude extracts and the partially purified extracts from MP-TI/SH2 was 2-3 fold higher than from MP/SH2 (FIG. 3). MP-TI/SH2, in its pure form (FIG. 4), maintained the favorable kinetic properties of MP/SH2 (Table 3) except that its $k_{cat}$ was reduced ~30% compared to MP/SH2. Additionally, MP-TI/SH2 exhibits greater heat stability than does MP/SH2 (FIGS. 6A-6B).

Figure 7A:
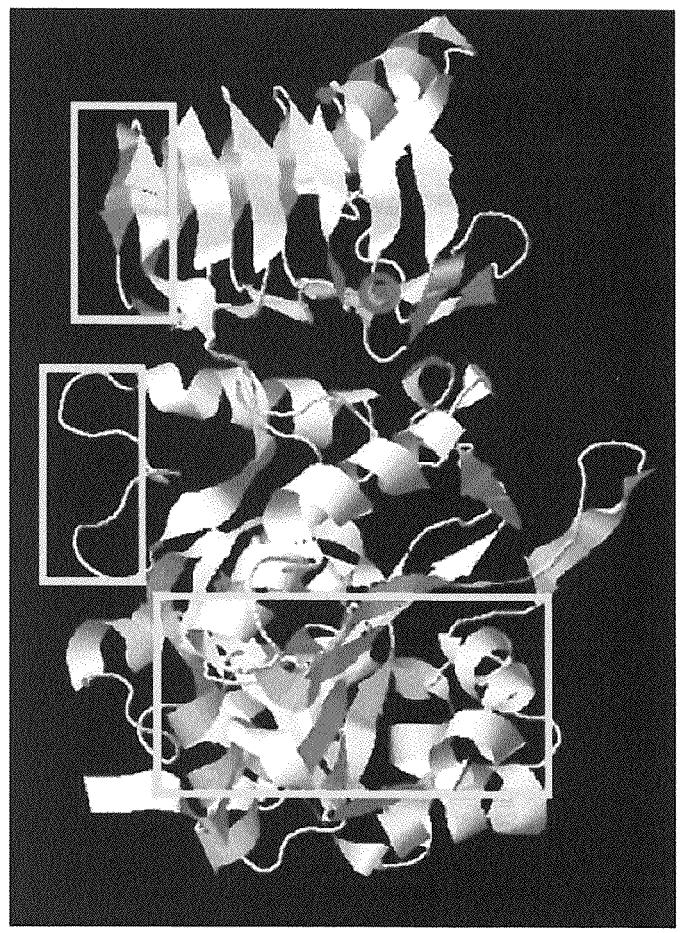
FIGS. 7A-7C show 3D modeling of BT2 and TI.
Figure 7B:
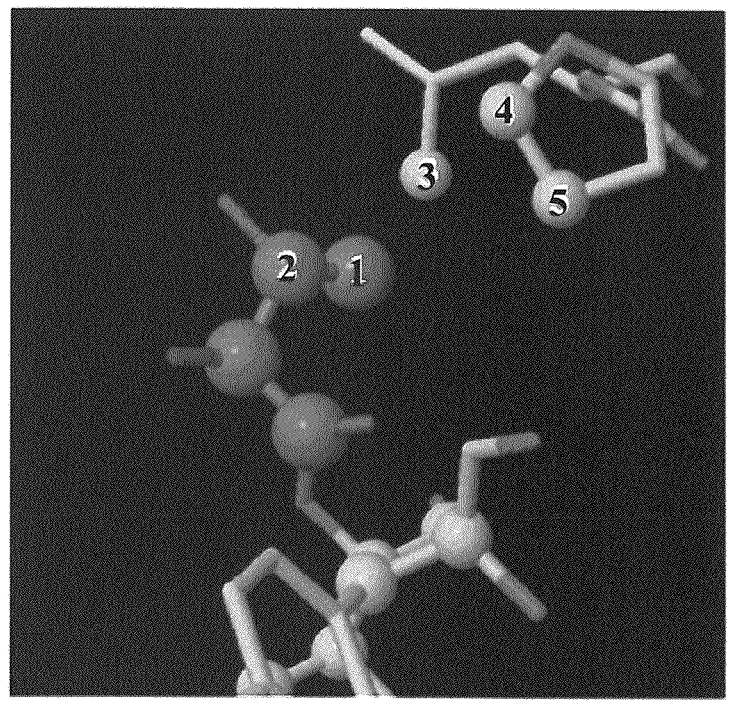
Figure 7C:
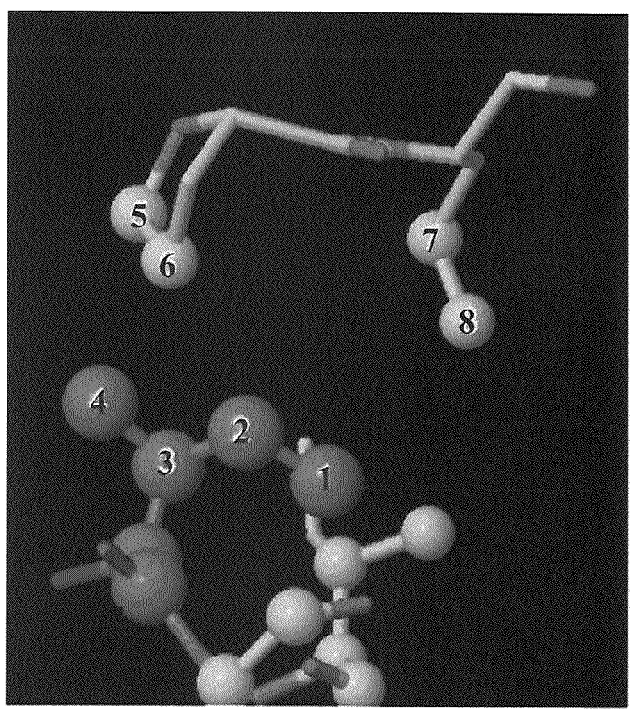

The crystal structure of maize endosperm AGPase has not been resolved. The only relevant structure is a potato tuber small subunit homotetramer (Jin et al., 2005). The potato tuber small subunit shows 88% identity and 96% similarity to BT2. BT2 monomer structure was modeled after the resolved structure of the potato tuber small subunit (FIG. 7A). The residue mutated in TI is part of a β-helix and it makes hydrophobic contact with two residues (Pro, Leu) of the N-terminus of the small subunit (FIG. 7B). The amino acid change from Thr to Ile in TI shortens the distance from the Pro and Leu mentioned above (FIG. 7C). It is tempting to speculate that the TI mutation strengthens the hydrophobic interaction between the C- and the N-terminus of the small subunit and results in greater stability. Unlike MP, whose heat stability is attributed to residues at/near the subunit-subunit interfaces, TI may not directly affect subunit-subunit interactions since it is far from the subunit-subunit interfaces (FIG. 7A).

Figure 8:
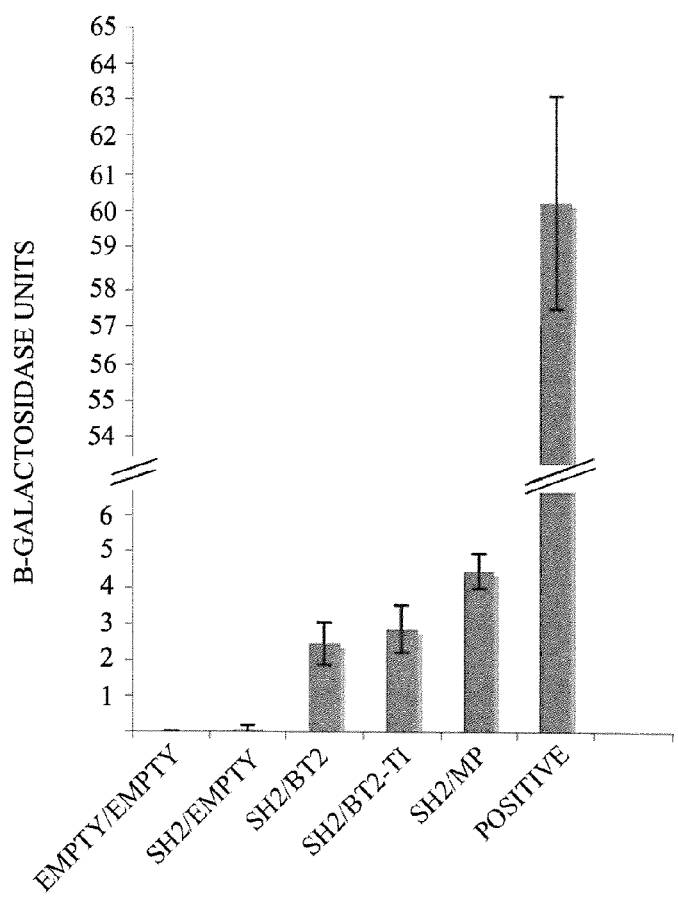
FIG. 8 show strength of AGPase subunit-subunit interactions. SH2 was used as a bait and BT2, TI, and MP as a prey in a yeast two hybrid system. A quantitative β-galactosidase assay was used to quantify the interactions between the bait and the prey. The error bars indicate 2× standard error (N=4).

To determine whether TI affects the strength of subunit-subunit interactions SH2 was used as a bait and BT2, TI, and MP were used as a prey in a yeast two-hybrid system (Y2H). A quantitative β-galactosidase assay indicated that, in contrast to MP, TI did not increase the strength of subunit-subunit interactions (FIG. 8).

Finally, replacements of the original threonine by amino acids with shorter side chains such as serine, alanine and glycine did not affect the heat stability of AGPase even though they did result in 10-fold or more reduction in $k_{cat}$ (data not shown). This indicates that the original threonine in position 462 is important for AGPase activity but not for heat stability.

EXAMPLE 2

The subject invention provides for agronomically important plant AGPase variants by using random mutagenesis and a heterologous bacterial expression system. BT2-TI was isolated as a small subunit variant that increased the amount of glycogen produced by E. coli cells when expressed along with SH2. Cells expressing BT2-TI/SH2 had 20-fold higher AGPase activity than cells expressing BT2/SH2. A dot-blot indicated that the crude protein extract from cells expressing BT2-TI/SH2 had more detectable BT2 protein compared to cells expressing BT2/SH2. This result could be attributed to more efficient transcription/translation or to greater AGPase stability and/or solubility. As mentioned previously, a more efficient transcription/translation is unlikely based on codon usage. On the other hand, it was showed that the purified form of BT2-TI/SH2 was significantly more heat-stable than the purified form of BT2/SH2. This may render the BT2-TI/SH2 complex less prone to proteolysis and/or aggregation compared to BT2/SH2 in E. coli.

The kinetic and allosteric properties of BT2-TI/SH2 were indistinguishable from BT2/SH2 except for a 30% lower $k_{cat}$. The 20-fold increase in AGPase activity of BT2-TI/SH2 expressing cells is interpreted as a higher number of active AGPase molecules compared to BT2/SH2 expressing cells. This also means that less than 5% of the potential AGPase molecules actually function in BT2/SH2.

It has been reported that the potato tuber small subunit can form a homotetramer that has significant activity when given extremely high amounts of the activator 3-PGA (Ballicora et al., 1995). As shown herein, E. coli cells expressing BT2 and BT2-TI as homotetramers do not produce detectable amounts of glycogen. Hence, the increased amounts of glycogen observed in cells expressing BT2-TI/SH2 compared to cells expressing BT2/SH2 is due to the complex of BT2-TI with SH2 rather than the BT2-TI homotetramer.

Another small subunit variant that results in increased heat stability in a complex with SH2 is MP. The heat stability conferred by MP has been mapped to residues near or at the subunit-subunit interaction interfaces (Boehlein, Shaw, Stewart, and Hannah, unpublished data). In contrast, the amino acid change of BT2-TI is far from these interfaces. Structure modeling suggests that the TI change strengthens the intrasubunit hydrophobic interactions between the C- and the N-terminus. The results from Y2H support the idea that, in contrast to MP, TI does not strengthen the subunit-subunit interactions. However, the possibility that TI indirectly affects subunit-subunit interactions through a conformational change cannot be dismissed. It is possible that Y2H may not be sensitive enough to reveal a difference in subunit-subunit interactions between TI/SH2 and BT2/SH2 at the yeast growth temperature of 30° C.

A comparison of the heat stability of pure BT2-TI/SH2 and MP/SH2 indicated that BT2-TI/SH2 was not as heat-stable as MP/SH2. Additionally, MP/SH2 has several advantages not shared by BT2-TI/SH2, such as activity in the absence of the activator 3-PGA, a higher affinity for 3-PGA, a lower affinity for the inhibitor Pi and a higher $k_{cat}$ compared to BT2/SH2. It was investigated whether the heat stability of MP/SH2 could be further improved by introducing the TI change into MP. The resulting variant, MP-TI, when expressed with SH2 in E. coli, yielded an equal amount of glycogen as MP/SH2. This could mean that either MP-TI/SH2 was not more heat-stable than MP/SH2 or that the production of ADP-glucose catalyzed by AGPase was not limiting in E. coli anymore. The latter interpretation may be favored since AGPase activity in crude and partially purified extracts of cells expressing MP-TI/SH2 was 2-3 fold higher than cells expressing MP/SH2. MP-TI/SH2 maintained all the kinetic and allosteric properties of MP/SH2 with the exception a 30% lower $k_{cat}$. Most importantly, MP-TI/SH2 was more heat-stable than MP/SH2. Two phases of heat stability in both MP-TI/SH2 and MP/SH2 were observed. These phases were probably a result of different states of AGPase. This biphasic mode of heat stability has been observed before and it is not specific to MP/SH2 or MP-TI (Boehlein et al. 2008). The first phase shows lower heat stability than does the second one. MP-TI/SH2 is more heat-stable in both phases compared to MP/SH2. However, what exactly the state of AGPase is in each phase remains enigmatic. The biphasic mode of heat stability was not observed in BT2/SH2 and BT2-TI/SH2 because the samples were not heated for long enough time to reach the second phase and they were heated at lower temperature than MP/SH2 and MP-TI/SH2 (42° C. instead of 53° C.).

Table 3 shows the kinetic properties of purified recombinant AGPase variants. The kinetic and allosteric properties of AGPase variants were determined in the forward direction. $k_{cat}$ $(s^{-1})$(G-1-P) was estimated by varying the amount of G-1-P and keeping ATP at saturating amounts (1 mM). $k_{cat}$ $(s^{-1})$ (ATP) was estimated by varying the amount of ATP and keeping G-1-P at saturating amounts (2 mM). $K_i$'s are expressed as mean (95% confidence interval). All other values are expressed as mean±standard deviation. The specific activity of AGPase in the absence of 3-PGA is expressed as a percentage of the specific activity in the presence of 10 mM of 3-PGA (mean±standard error).

TABLE 3

|  | BT2/SH2 | BT2-TI/SH2 | MP/SH2 | MP-TI/SH2 |
|---|---|---|---|---|
| $K_m$ G-1-P (mM) | 0.050 (±0.008) | 0.040 (±0.006) | 0.079 (±0.007) | 0.059 (±0.005) |
| $k_{cat}(s^{-1})$ (G-1-P) | 38.170 (±1.323) | 26.200 (±1.401) | 62.655 (±2.569) | 42.880 (±1.880) |
| $K_m$ ATP (mM) | 0.102 (±0.020) | 0.146 (±0.050) | 0.133 (±0.021) | 0.112 (±0.013) |
| $k_{cat}(s^{-1})$ (ATP) | 43.321 (±1.554) | 29.112 (±1.030) | 69.337 (±3.276) | 49.031 (±1.903) |
| $K_a$ 3-PGA (mM) | 0.480 (±0.137) | 0.330 (±0.060) | 0.100 (±0.010) | 0.068 (±0.010) |
| $K_i$ Pi (mM) | 2.320 (0.530, 4.100) | 4.070 (2.120, 6.020) | 6.610 (4.530, 8.690) | 5.870 (4.410, 7.330) |

| $V_{max}$ − 3-PGA/$V_{max}$ + 3-PGA (nmol/min/mg) | | | |
|---|---|---|---|
| BT2/SH2 | BT2-TI/SH2 | MP/SH2 | MP-TI/SH2 |
| 280/4000 (7.2 ± 3.2%) | 134/2737 (4.9 ± 1.5%) | 1856/6584 (28.2 ± 3.1%) | 1101/4513 (24.4 ± 5.3%) |

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

U.S. Pat. No. 5,034,322
U.S. Pat. No. 5,106,739
U.S. Pat. No. 5,589,610
U.S. Pat. No. 5,589,618
U.S. Pat. No. 5,625,136
U.S. Pat. No. 5,639,948
U.S. Pat. No. 5,650,557
U.S. Pat. No. 5,661,017
U.S. Pat. No. 5,872,216
U.S. Pat. No. 6,069,300
U.S. Pat. No. 6,184,438
U.S. Pat. No. 6,403,863
U.S. Pat. No. 6,455,760
U.S. Pat. No. 6,462,185
U.S. Pat. No. 6,696,623
U.S. Pat. No. 6,809,235
U.S. Pat. No. 6,969,783
U.S. Pat. No. 7,173,165
U.S. Pat. No. 7,312,378
U.S. Published Application No. 20030084486
U.S. Published Application No. 20030177536
U.S. Published Application No. 20040019934
U.S. Published Application No. 20040067506
U.S. Published Application No. 20040078841
U.S. Published Application No. 20040123349
International Published Application WO 2005/019425
International Published Application WO 99/58698
International Published Application WO 2003/0070901
International Published Application WO 98/22601
International Published Application WO 02/072784
EPO Patent Published Application No. EP 1528104
Altschul, S. F. et al. (1990) "Basic Local Alignment Search Tool" *J. Mol. Biol.* 215:402-410.
Altschul, S. F. et al. (1997) "Gapped BLAST and PSI-BLAST: A New Generation of Protein Database Search Programs" *Nucl. Acids Res.* 25:3389-3402.
Arnold, K., Bordoli, L., Kopp, J., and Schwede, T. (2006) "The SWISS-MODEL Workspace: A web-based environment for protein structure homology modeling" *Bioinformatics* 22: 195-201.
Ballicora, M. A., Laughlin, M. J., Fu, Y., Okita, T. W., Barry, G. F. and Preiss, J. (1995) "Adenosine 5'-diphosphate-glucose pyrophosphorylase from potato tuber. Significance of the N-terminus of the small subunit for catalytic properties and heat stability" *Plant Physiol.* 109: 245-251.
Beltz, G. A., Jacobs, K. A., Eickbush, T. H., Cherbas, P. T., Kafatos, F. C. (1983) "Isolation of multigene families and determination of homologies by filter hybridization methods" *Methods of Enzymology*, R. Wu, L. Grossman and K. Moldave [eds.] Academic Press, New York 100:266-285.
Bhullar, S. S., and Jenner, C. F. (1985) "Differential responses to high temperatures of starch and nitrogen accumulation in the grain of four cultivars of wheat" *Aust. J. Plant Physiol.* 12: 363-375.
Boehlein, S. K., Sewell, A. K., Cross, J., Stewart, J. D., and Hannah, L. C. (2005) "Purification and characterization of adenosine diphosphate glucose pyrophosphorylase from maize/potato mosaics" *Plant Physiol.* 138: 1552-1562.
Boehlein, S. K., Shaw, J. R., Stewart, J. D., and Hannah, L. C. (2008) "Heat Stability and Allosteric Properties of the Maize Endosperm ADP-Glucose Pyrophosphorylase Are Intimately Intertwined" *Plant Physiol.* 146: 289-299.
Chang, J. (1981) "Corn yield in relation to photoperiod, night temperature, and solar radiation" *Agricul. Metero.* 24: 253-262.
Cheikn, N., and Jones, R. (1995) "Heat stress effects on sink activity of developing maize kernels grown in vitro" *Physiol. Plant.* 95: 59-66.
Christy, A. L., and Williamson, D. R. (1985) "Characteristics of CO2 fixation and productivity of corn and soybeans" Pages 379-387 in P. W. Luden and J. E. Burris eds. Nitrogen Fixation and CO2 Metabolism. Elsevier Science Publishing Co., New York.
Christy, A. L., Williamson, D. R., and Wideman, A. S. (1985) "Maize source development and activity. In 'Regulation of Carbon and Nitrogen Reduction and Utilization in Maize'" (Eds J. C. Shannon and C. D. Boyer.) pp 11-20. (American Society of Plant Physiologists: Rockville).
Clancy, M. and Hannah, L. C. (2002) "Splicing of the maize Sh1 first intron is essential for enhancement of gene expression, and a T-rich motif increases expression without affecting splicing" *Plant Physiol.* 130(2):918-29.

Cross, J. M., Clancy, M., Shaw, J., Greene, T. W., Schmidt, R. R. Okita, T. W. and Hannah, L. C. (2004) "Both subunits of ADP-glucose pyrophosphorylase are regulatory" *Plant Physiol.* 135: 137-140.

Deng, Z., Roberts, D., Wang, X., and Kemp R. G. (1999) "Expression, characterization, and crystallization of the pyrophosphate-dependent phosphofructo-1-kinase of *Borrelia burgdorferi*" *Arch. Biochem. Biophys.* 371: 326-331.

Duke, E., and Doehlert, D. (1996) "Effects of heat stress on enzyme activities and transcript levels in developing maize kernels grown in culture" *Environ. Exp. Botany* 36: 199-208.

Duncan, W. G., and Hesketh, J. D. (1968) "Net photosynthetic rates, relative leaf growth rates, and leaf numbers of 22 races of maize grown at eight temperatures" *Crop Science* 8: 670-674.

Furtado, A. et al. (2002) "Tools for Use in the Genetic Engineering of Barley" *Proceedings of the 10$^{th}$ Australian Barley technical Symposium,* Canberra, ACT, Australia.

Georgelis, N., Braun, E. L., Shaw, J. R., and Hannah, L. C. (2007) "The two AGPase subunits evolve at different rates in angiosperm, yet they are equally sensitive to activity altering amino acid changes when expressed in bacteria" *Plant Cell* 19: 1458-1472.

Giroux, M. J., Shaw, J., Barry, G., Cobb, B. G., Greene, T. W., Okita, T. W., and Hannah, L. C. (1996) "A single mutation that increases maize seed weight" *Proc. Natl. Acad. Sci. USA* 93: 5824-5829.

Good, X. et al. (1994) "Reduced ethylene synthesis by transgenic tomatoes expressing S-adenosylmethionine hydrolase" *Plant Molec. Biol.* 26:781-790.

Govons, S., Vinopal, R., Ingraham, J., and Preiss J. (1969) "Isolation of mutants of *Escherichia coli* B altered in their ability to synthesize glycogen" *J. Bacteriol.* 97: 970-972.

Greene, T. W., and Hannah, L. C. (1998a) "Enhanced stability of maize endosperm ADP-glucose pyrophosphorylase is gained through mutants that alter subunit interactions" *Proc. Natl. Acad. Sci. USA* 95: 13342-13347.

Greene, T. W., and Hannah, L. C. (1998b) "Assembly of maize endosperm ADP-glucose pyrophosphorylase requires motifs located throughout the large and small subunit units" *Plant Cell* 10: 1295-1306.

Greene, T. W., Kavaldi, I. H., Kahn, M., and Okita, T. W. (1998) "Generation of up-regulated allosteric variants of potato ADP-glucose pyrophosphorylase by reversion genetics" *Proc. Natl. Acad. Sci. USA* 95: 10322-10327.

Guex, N., and Peitsch, M. C. (1997) "SWISS-MODEL and the Swiss-PdbViewer: An environment for comparative protein modeling" *Electrophoresis* 18: 2714-2723.

Hall, T. A. (1999) "BioEdit, a user-friendly biological sequence alignment editor and analysis program for Windows 95/98/NT" *Nucl. Acids Symp. Ser.* 41: 95-98.

Hannah L. C., Shaw, J. R., Giroux, M., Reyss, A., Prioul, J.-L., Bae, J.-M. and Lee, J.-Y. (2001) "Maize Genes Encoding the Small Subunit of ADP-Glucose Pyrophosphorylase" *Plant Physiol.* 127:173-183.

Hannah, L. C., Tuschall, D., and Mans, R. (1980) "Multiple forms of maize endosperm ADP-glucose pyrophosphorylase and their control by Shrunken-2 and Brittle-2" *Genetics* 95: 961-970.

Hannah, L. C., and Nelson, O. E., Jr. (1976) "Characterization of ADP-glucose pyrophosphorylase from shrunken-2 and brittle-2 mutants of maize" *Biochem. Genet.* 14: 547-560.

Hanson, R. S., and Phillips, J. A. (1981) "Chemical composition", p. 328-364. In P. Gerhandt, et al. (ed.), Manual of methods for general bacteriology. American Society for Microbiology, Washington, D.C.

Hofstra, G., and Hesketh, J. D. (1969) "Effects of temperature on the gas exchange of leaves in the light and dark" *Planta* 85: 228-237.

Hunter, R., Tollenaar, M., and Breuer, C. (1977) "Effects of photoperiod and temperature on vegetative and reproductive growth of maize (*Zea mays*) hybrid" *Can. J. Plant Sci.* 57: 1127-1133.

Hwang, Y-S. et al. (2002) "Analysis of the Rice Endosperm-Specific Globulin Promoter in Transformed Rice Cells" *Plant Cell Rep.* 20:842-847.

Iglesias, A., Barry, G. F., Meyer, C., Bloksberg, L., Nakata, P., Greene, T., Laughlin M. J., Okita T. W., Kishore G. M., and Preiss, J. (1993) "Expression of the potato tuber ADP-glucose pyrophosphorylase in *Escherichia coli*" *J. Biol. Chem.* 268: 1081-1086.

Jin, X., Ballicora, M. A., Preiss, J., and Geiger, J. H. (2005) "Crystal structure of potato tuber ADP-glucose pyrophosphorylase" *EMBO J.* 24: 694-704.

Jones, R., Ouattar, S., and Crookston, R. (1984) "Thermal environment during endosperm cell division and grain filling in maize: effects on kernel growth and development in vitro" *Crop Science* 24: 133-137.

Karlin S. and Altschul, S. F. (1990) "Methods for Assessing the Statistical Significance of Molecular Sequence Features by Using General Scoring Schemes" *Proc. Natl. Acad. Sci. USA* 87:2264-2268.

Karlin S. and Altschul, S. F. (1993) "Applications and Statistics for Multiple High-Scoring Segments in Molecular Sequences" *Proc. Natl. Acad. Sci. USA* 90:5873-5877.

Kopp, J., and Schwede, T. (2004) "The SWISS-MODEL Repository of annotated three-dimensional protein structure homology models" *Nucleic Acids Research* 32: D230-D234.

Laemmli, U. K. (1970) "Cleavage of structural proteins during the assembly of the head of bacteriophage T4" *Nature* 227: 680-685.

Lewin, B. (1985) *Genes II*, John Wiley & Sons, Inc., p. 96.

Maniatis, T., E. F. Fritsch, J. Sambrook (1982) "Nuclease Bal31" *Molecular Cloning: A Laboratory Manual*, Cold Spring Harbor Laboratory, Cold Spring Harbor, N.Y.

Nakamura, Y., Gojobori, T., and Ikemura, T. (2000) "Codon usage tabulated from international DNA sequence databases: status for the year 2000" *Nucleic Acids Res.* 28: 292.

Obana, Y., Omoto, D., Kato, C., Matsumoto, K., Nagai, Y., Kavakli, I. H., Hamada, S., Edwards, G. E., Okita, T. W., Matsui, H., and Ito, H. (2006) "Enhanced turnover of transitory starch by expression of up-regulated ADP-glucose pyrophosphorylase in *Arabidopsis thaliana*" *Plant Sci.* 170: 1-11.

Peitsch, M. C. (1995) Protein modeling by E-mail Bio/Technology 13: 658-660.

Peters, D. B., Pendleton, J. W., Hageman, R. H., and Brown, C. M. (1971) "Effect of night air temperature on grain yield of corn, wheat and soybeans" *Agron. J.* 63: 809.

Sakulsingharoja, C., Choi, S. B., Hwang, S. K., Edwards, G. E., Bork, J., Meyer, C. R., Preiss, J., and Okita, T. W. (2004) "Engineering starch biosynthesis for increasing rice seed weight: the role of the cytoplasmic ADP-glucose pyrophosphorylase" *Plant Sci.* 167: 1323-1333.

Schwede, T., Kopp, J., Guex, N., and Peitsch, M. C. (2003) "SWISS-MODEL: an automated protein homology-modeling server" *Nucleic Acids Res.* 31: 3381-3385.

Singletary, G., Banisadr, R., and Keeling, P. (1993) "Decreased starch synthesis in heat stressed maize kernels results from reduced ADPG-pyrophosphorylase and starch synthase activities" *Plant Physiol. Suppl.* 102: 6.

Singletary, G., Banisadr, R., and Keeling, P. (1994) "Heat stress during grain filling in maize: effects of carbohydrate storage and metabolism" *Aust. J. Plant Physiol.* 21: 829-841.

Smidansky, E. D., Clancy, M., Meyer, F. D., Laming, S. P., Blake, N. K., Talbert, L. E., and Giroux, M. J. (2002) "Enhanced ADP-glucose pyrophosphorylase activity in wheat endosperm increases seed yield" *Proc. Natl. Acad. Sci.* 99: 1724-1729.

Smidansky, E. D., Martin, J. M., Hannah, L. C., Fischer, A. M., and Giroux, M. J. (2003) "Seed yield and plant biomass increases in rice are conferred by deregulation of endosperm ADP-glucose pyrophosphorylase" *Planta* 216: 656-664.

Stark, D. M., Timmerman, K. P., Barry, G., Preiss, J., and Kishore, G. M. (1992) "Regulation of the amount of starch in plant tissues by ADP-glucose pyrophosphorylase" *Science* 258: 287-292.

Thompson, L. (1975) "Weather variability, climatic change and grain production" *Science* 188: 535-541.

Tollenaar, M., and Bruulsema, T. (1988) "Effects of temperature on rate and duration of kernel dry matter accumulation of maize" *Can. J. Plant Sci.* 68: 935-940.

Tsai, C. Y., and Nelson, O. E. (1966) "Starch deficient maize mutants lacking adenosine diphosphate glucose pyrophosphorylase activity" *Science* 151: 341-343.

Wallwork, M. A. B., Logue, S. J., MacLeod, L. C., and Jenner, C. F. (1998) "Effect of high temperature during grain filling on starch synthesis in the developing barley grain" *Aust. J. Plant Physiol.* 25: 173-181.

Wang, Z., Chen, X., Wang, J., Liu, T., Liu, Y., Zhao, L., and Wang, G. (2007) "Increasing maize seed weight by enhancing the cytoplasmic ADP-glucose pyrophosphorylase activity in transgenic plants" *Plant Cell Tiss. Organ Cult.* 88: 83-92.

Wilhelm, E., Mullen, R., Keeling, P., and Singletary, G. (1999) "Heat stress during grain filling in maize: Effects on kernel growth and metabolism" *Crop Science* 39: 1733-1741.

Wu, C-L. et al. (1998) "Promoters of Rice Seed Storage Protein Genes Direct Endosperm-Specific Gene Expression in Transgenic Rice" *Plant and Cell Physiology,* 39(8): 885-889.

Xu, D., McElroy, D., Thornburg, R. W., Wu, R. et al. (1993) "Systemic induction of a potato pin2 promoter by wounding, methyl jasmonate, and abscisic acid in transgenic rice plants" *Plant Molecular Biology* 22:573-588.

---

We claim:

1. A polynucleotide encoding a mutant plant AGPase small subunit protein, or a functional fragment of said protein, said protein comprising an amino acid mutation wherein the amino acid corresponding to the threonine amino acid at position 462 of wild type maize endosperm AGPase small subunit protein is replaced by an amino acid that confers increased heat stability when said mutant AGPase small subunit is expressed to form an AGPase enzyme, wherein said fragment comprises said amino acid mutation at position 462 and wherein said fragment provides for said increased heat stability when said fragment is expressed to form an AGPase enzyme, wherein said replacement amino acid that confers increased heat stability is an isoleucine.

2. The polynucleotide according to claim 1, wherein said mutant AGPase small subunit is a maize endosperm AGPase small subunit.

3. The polynucleotide according to claim 1, wherein said mutant plant AGPase small subunit protein encoded by said polynucleotide comprises the amino acid sequence shown in any one of SEQ ID NO: 2, SEQ ID NO: 5, SEQ ID NO: 6, SEQ ID NO: 7, SEQ ID NO: 21, SEQ ID NO: 22, SEQ ID NO: 23, SEQ ID NO: 24, or SEQ ID NO: 25, or a functional fragment thereof, wherein said fragment comprises said replacement amino acid at position 462 and wherein said fragment provides for said increased heat stability when said fragment is expressed to form an AGPase enzyme.

4. The polynucleotide according to claim 1, wherein said polynucleotide comprises the nucleotide sequence shown in any one of SEQ ID NO: 1, SEQ ID NO: 11, SEQ ID NO: 12, or SEQ ID NO: 13, or a functional fragment thereof, wherein said fragment encodes an amino acid sequence comprising said amino acid mutation at position 462 and wherein said fragment provides for said increased heat stability when said fragment is expressed to form an AGPase enzyme.

5. A polynucleotide encoding a chimeric plant AGPase small subunit protein, or a functional fragment of said protein, wherein said chimeric AGPase protein comprises an N-terminus sequence from an N-terminus region of a plant AGPase small subunit from a first plant and a C-terminus sequence from a C-terminus region of a plant AGPase small subunit from a second plant, and said chimeric plant AGPase small subunit protein comprises an amino acid mutation wherein the amino acid corresponding to the threonine amino acid at position 462 of wild type maize endosperm AGPase small subunit protein is replaced by an amino acid that confers increased heat stability when said mutant AGPase small subunit is expressed to form an AGPase enzyme, wherein said fragment encodes an amino acid sequence comprising said amino acid mutation at position 462 and wherein said fragment provides for said increased heat stability when said fragment is expressed to form an AGPase enzyme, wherein said replacement amino acid that confers increased heat stability is an isoleucine.

6. The polynucleotide according to claim 5, wherein said N-terminus sequence comprises the first 150 to 250 amino acids of the N-terminus region of said subunit of AGPase of said first plant and said C-terminus sequence comprises the terminal 300 residues or less of the C-terminus region of said subunit of AGPase of said second plant, wherein said C-terminus comprises at least the replacement amino acid relative to position 462 of a wild type maize endosperm AGPase small subunit protein.

7. The polynucleotide according to claim 5, wherein said N-terminus region is from maize endosperm small subunit of AGPase and/or said C-terminus region is from potato tuber small subunit of AGPase.

8. The polynucleotide according to claim 5, wherein said plant AGPase small subunit protein encoded by said polynucleotide comprises the amino acid sequence shown in any of SEQ ID NO: 4, SEQ ID NO: 8, SEQ ID NO: 9, or SEQ ID NO: 10, or a functional fragment thereof, wherein said fragment comprises said replacement amino acid at position 462 and wherein said fragment provides for said increased heat stability when said fragment is expressed to form an AGPase enzyme.

9. The polynucleotide according to claim 5, wherein said polynucleotide comprises the nucleotide sequence shown in any of SEQ ID NO: 3, SEQ ID NO: 14, SEQ ID NO: 15, or SEQ ID NO: 16, or a functional fragment thereof, wherein said fragment encodes an amino acid sequence comprising said amino acid mutation at position 462 and wherein said fragment provides for said increased heat stability when said fragment is expressed to form an AGPase enzyme.

10. A protein comprising:
a) a polypeptide encoded by a polynucleotide encoding a mutant plant AGPase small subunit protein, or a functional fragment of said protein, said protein comprising an amino acid mutation wherein the amino acid corresponding to the threonine amino acid at position 462 of wild type maize endosperm AGPase small subunit protein is replaced by an amino acid that confers increased heat stability when said mutant AGPase small subunit is expressed to form an AGPase enzyme, wherein said fragment comprises said amino acid mutation at position 462 and wherein said fragment provides for said increased heat stability when said fragment is expressed to form an AGPase enzyme, wherein said replacement amino acid is isoleucine; or
b) a polypeptide encoded by a polynucleotide encoding a chimeric plant AGPase small subunit protein, or a functional fragment of said protein, wherein said chimeric AGPase protein comprises an N-terminus sequence from an N-terminus region of a plant AGPase small subunit from a first plant and a C-terminus sequence from a C-terminus region of a plant AGPase small subunit from a second plant, and said chimeric plant AGPase small subunit protein comprises an amino acid mutation wherein the amino acid corresponding to the threonine amino acid at position 462 of wild type maize endosperm AGPase small subunit protein is replaced by an amino acid that confers increased heat stability when said mutant AGPase small subunit is expressed to form an AGPase enzyme, wherein said fragment comprises said amino acid mutation at position 462 and wherein said fragment provides for said increased heat stability when said fragment is expressed to form an AGPase enzyme, wherein said replacement amino acid is isoleucine; or
c) the polypeptide of a) and the polypeptide of b), wherein the polypeptide of a) and polypeptide of b) form a multimeric protein complex.

11. A transformed or transgenic plant or plant tissue or cell comprising:
a) a polypeptide encoded by a polynucleotide encoding a mutant plant AGPase small subunit protein, or a functional fragment of said protein, said protein comprising an amino acid mutation wherein the amino acid corresponding to the threonine amino acid at position 462 of wild type maize endosperm AGPase small subunit protein is replaced by an amino acid that confers increased heat stability when said mutant AGPase small subunit is expressed to form an AGPase enzyme, wherein said fragment comprises said amino acid mutation at position 462 and wherein said fragment provides for said increased heat stability when said fragment is expressed to form an AGPase enzyme, wherein said replacement amino acid is isoleucine; or
b) a polypeptide encoded by a polynucleotide encoding a chimeric plant AGPase small subunit protein, or a functional fragment of said protein, wherein said chimeric AGPase protein comprises an N-terminus sequence from an N-terminus region of a plant AGPase small subunit from a first plant and a C-terminus sequence from a C-terminus region of a plant AGPase small subunit from a second plant, and said chimeric plant AGPase small subunit protein comprises an amino acid mutation wherein the amino acid corresponding to the threonine amino acid at position 462 of wild type maize endosperm AGPase small subunit protein is replaced by an amino acid that confers increased heat stability when said mutant AGPase small subunit is expressed to form an AGPase enzyme, wherein said fragment comprises said amino acid mutation at position 462 and wherein said fragment provides for said increased heat stability when said fragment is expressed to form an AGPase enzyme, wherein said replacement amino acid is isoleucine; or
c) the polypeptide of a) and the polypeptide of b), wherein the polypeptide of a) and polypeptide of b) form a multimeric protein complex.

12. The plant or plant tissue or cell according to claim 11, wherein said plant or plant tissue or cell is monocotyledonous.

13. The plant or plant tissue or cell according to claim 12, wherein said monocotyledonous plant or plant tissue or cell is selected from the group consisting of rice, wheat, barley, oats, rye, sorghum, maize, sugarcane, pineapple, onion, bananas, coconut, lilies, turfgrasses, and millet.

14. A method of increasing resistance of a plant to heat stress conditions and/or increasing starch biosynthesis of a plant, said method comprising incorporating one or more polynucleotide into the genome of a plant and expressing the protein encoded by said polynucleotide, wherein said polynucleotide is or comprises:
a) any polynucleotide encoding a mutant plant AGPase small subunit protein, or a functional fragment of said protein, said protein comprising an amino acid mutation wherein the amino acid corresponding to the threonine amino acid at position 462 of wild type maize endosperm AGPase small subunit protein is replaced by an amino acid that confers increased heat stability when said mutant AGPase small subunit is expressed to form an AGPase enzyme, wherein said fragment comprises said amino acid mutation at position 462 and wherein said fragment provides for said increased heat stability when said fragment is expressed to form an AGPase enzyme, wherein said replacement amino acid is isoleucine; and/or b) any polynucleotide encoding a chimeric plant AGPase small subunit protein, or a functional fragment of said protein, wherein said chimeric AGPase protein comprises an N-terminus sequence from an N-terminus region of a plant AGPase small subunit from a first plant and a C-terminus sequence from a C-terminus region of a plant AGPase small subunit from a second plant, and said chimeric plant AGPase small subunit protein comprises an amino acid mutation wherein the amino acid corresponding to the threonine amino acid at position 462 of wild type maize endosperm AGPase small subunit protein is replaced by an amino acid that confers increased heat stability when said mutant AGPase small subunit is expressed to form an AGPase enzyme, wherein said fragment comprises said amino acid mutation at position 462 and wherein said fragment provides for said increased heat stability when said fragment is expressed to form an AGPase enzyme, wherein said replacement amino acid is isoleucine.

15. The method according to claim 14, wherein said plant is monocotyledonous.

16. The method according to claim 15, wherein said monocotyledonous plant is selected from the group consisting of rice, wheat, barley, oats, rye, sorghum, maize, sugarcane, pineapple, onion, bananas, coconut, lilies, turfgrasses, and millet.

17. A method for preparing a plant having a mutant AGPase enzyme that provides for increased heat stability and/or increased starch biosynthesis in the plant relative to a plant expressing a wild type AGPase enzyme, said method comprising introducing one or more polynucleotide into a plant cell and growing a plant from said plant cell, wherein said plant expresses said mutant AGPase enzyme, wherein said polynucleotide is or comprises:

a) any polynucleotide encoding a mutant plant AGPase small subunit protein, or a functional fragment of said protein, said protein comprising an amino acid mutation wherein the amino acid corresponding to the threonine amino acid at position 462 of wild type maize endosperm AGPase small subunit protein is replaced by an amino acid that confers increased heat stability when said mutant AGPase small subunit is expressed to form an AGPase enzyme, wherein said fragment comprises said amino acid mutation at position 462 and wherein said fragment provides for said increased heat stability when said fragment is expressed to form an AGPase enzyme, wherein said replacement amino acid is isoleucine; and/or b) any polynucleotide encoding a chimeric plant AGPase small subunit protein, or a functional fragment of said protein, wherein said chimeric AGPase protein comprises an N-terminus sequence from an N-terminus region of a plant AGPase small subunit from a first plant and a C-terminus sequence from a C-terminus region of a plant AGPase small subunit from a second plant, and said chimeric plant AGPase small subunit protein comprises an amino acid mutation wherein the amino acid corresponding to the threonine amino acid at position 462 of wild type maize endosperm AGPase small subunit protein is replaced by an amino acid that confers increased heat stability when said mutant AGPase small subunit is expressed to form an AGPase enzyme, wherein said fragment comprises said amino acid mutation at position 462 and wherein said fragment provides for said increased heat stability when said fragment is expressed to form an AGPase enzyme, wherein said replacement amino acid is isoleucine.

18. The method according to claim 17, wherein said plant is monocotyledonous.

19. The method according to claim 18, wherein said monocotyledonous plant is selected from the group consisting of rice, wheat, barley, oats, rye, sorghum, maize, sugarcane, pineapple, onion, bananas, coconut, lilies, turfgrasses, and millet.

* * * * *

UNITED STATES PATENT AND TRADEMARK OFFICE
CERTIFICATE OF CORRECTION

| | | |
|---|---|---|
| PATENT NO. | : 8,536,407 B2 | Page 1 of 2 |
| APPLICATION NO. | : 12/922094 | |
| DATED | : September 17, 2013 | |
| INVENTOR(S) | : L. Curtis Hannah and Nikolaos Georgelis | |

It is certified that error appears in the above-identified patent and that said Letters Patent is hereby corrected as shown below:

In the Specification:

Column 29,
Line 43, "Kavaldi" should read --Kavakli--

Column 31,
Line 5, "Laming" should read --Lanning--

In the Claims:

Column 82,
Lines 61-63,
    "wherein said fragment encodes an amino acid sequence comprising said amino acid mutation at position 462"
  should read
    --and wherein said fragment comprises said amino acid mutation at position 462--

Column 83,
Lines 17-18, "in any of" should read --in any one of--
Lines 25-26, "in any of" should read --in any one of--
Lines 42-43, "enzyme, wherein said fragment" should read --enzyme, and wherein said fragment--
Line 62, "enzyme, wherein said fragment" should read --enzyme, and wherein said fragment--

Column 84,
Lines 6-7,
    "a polypeptide encoded by a polynucleotide encoding a mutant"
  should read
    --a polynucleotide encoding a mutant--

Signed and Sealed this
Twenty-ninth Day of July, 2014

Michelle K. Lee
*Deputy Director of the United States Patent and Trademark Office*

Column 84,
Lines 14-15, "enzyme, wherein said fragment" should read --enzyme, and wherein said fragment--
Lines 20-21,
    "a polypeptide encoded by a polynucleotide encoding a chimeric"
  should read
    --a polynucleotide encoding a chimeric--
Line 34, "enzyme, wherein said fragment" should read --enzyme, and wherein said fragment--
Lines 40-42,
    "the polypeptide of a) and the polypeptide of b), wherein the polypeptide of a) and polypeptide of b) form a multimeric protein complex."
  should read
    --the polynucleotides of both a) and b).--
Line 65, "enzyme, wherein said fragment" should read --enzyme, and wherein said fragment--

Column 85,
Lines 17-18, "enzyme, wherein said fragment" should read --enzyme, and wherein said fragment--

Column 86,
Line 7, "enzyme, wherein said fragment" should read --enzyme, and wherein said fragment--
Lines 26-27, "enzyme, wherein said" should read --enzyme, and wherein said--

UNITED STATES PATENT AND TRADEMARK OFFICE
CERTIFICATE OF CORRECTION

PATENT NO. : 8,536,407 B2
APPLICATION NO. : 12/922094
DATED : September 17, 2013
INVENTOR(S) : L. Curtis Hannah and Nikolaos Georgelis It is certified that error appears in the above-identified patent and that said Letters Patent is hereby corrected as shown below:

In the Specification

Column 1
Line 22, "Accordingly, the" should read --The--

Signed and Sealed this
Thirty-first Day of March, 2015

Michelle K. Lee
*Director of the United States Patent and Trademark Office*

UNITED STATES PATENT AND TRADEMARK OFFICE
CERTIFICATE OF CORRECTION

PATENT NO. : 8,536,407 B2  Page 1 of 1
APPLICATION NO. : 12/922094
DATED : September 17, 2013
INVENTOR(S) : Hannah et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 392 days.

Signed and Sealed this

Fifteenth Day of September, 2015

Michelle K. Lee
*Director of the United States Patent and Trademark Office*

SEQUENCE LISTING

```
<160> NUMBER OF SEQ ID NOS: 26

<210> SEQ ID NO 1
<211> LENGTH: 1425
<212> TYPE: DNA
<213> ORGANISM: Artificial Sequence
<220> FEATURE:
<223> OTHER INFORMATION: zea mays Bt2 gene
<220> FEATURE:
<221> NAME/KEY: misc_feature
<222> LOCATION: (1386)..(1386)
<223> OTHER INFORMATION: h = a or c or t

<400> SEQUENCE: 1
atggacatgg ctttggcgtc taaagcctcc cctccgccat ggaatgccac cgccgccgag      60
cagccaattc caaagcgtga caaagccgct gcaaatgatt caacatacct caatcctcaa     120
gctcatgata gtgttcttgg aatcattctg ggaggtggtg ctgggactag attgtacccc     180
ttgacaaaga agcgtgccaa gcctgcagtg ccattgggtg ccaactatag actgattgat     240
attcctgtca gcaattgtct caacagcaac atatccaaga tctatgtgct aacgcaattt     300
aactctgctt ccctcaaccg tcacctctca agagcctacg ggagcaacat tggagggtac     360
aagaatgaag ggtttgttga agtcttagct gcacagcaga gcccagataa tccaaactgg     420
tttcagggta ctgcagatgc tgtaaggcag tacttgtggt tgtttgagga gcataatgtg     480
atggaatttc taattcttgc tggcgatcac ctgtaccgga tggactatga aaagttcatt     540
caggcacaca gagaaacaaa tgctgatatt accgttgctg ccctaccgat ggatgagaaa     600
cgtgcaactg catttggcct catgaaaatt gatgaagaag ggaggatcat tgagtttgct     660
gagaaaccga aggagagca gttgaaagca atgatggttg acaccaccat acttggcctt     720
gatgacgtga gggcaaagga aatgccttat attgctagca tgggtatcta tgttttcagc     780
aaagatgtaa tgcttcagct cctccgtgaa caatttcctg aagccaatga ctttggaagt     840
gaggttattc aggtgcaac cagcattgga aagagggttc aggcttatct gtatgatggt     900
tactgggaag atatcggtac cattgcggca ttttataatg caaacttggg aataaccaag     960
```

-continued

```
aagccaatac cagatttcag cttctatgac cgttttgctc caatttatac acaacctcga    1020
cacctgccac cttcaaaggt tcttgatgct gatgtgacag acagtgttat tggtgaagga    1080
tgtgttatta aaaactgcaa gataaaccat tctgtagttg gactccgatc ttgcatatct    1140
gaaggtgcta tcatagagga cagtttacta atgggtgcgg actactatga dacagaagct    1200
```
(corrected)
```
gaaggtgcta tcatagagga cagtttacta atgggtgcgg actactatga gacagaagct    1200
gataaaaaac tccttgccga aaaggtggc attcctattg gtattgggaa aaattcatgc     1260
atcaggagag caatcattga caagaatgct cgaattggag acaatgttaa gatactcaat    1320
gctgacaatg ttcaagaagc tgcaatggag acagacgggt acttcatcaa aggtggaatt    1380
gtcathgtga tcaaggatgc tttactccct agtggaacag ttata                    1425
```

<210> SEQ ID NO 2
<211> LENGTH: 475
<212> TYPE: PRT
<213> ORGANISM: Artificial Sequence
<220> FEATURE:
<223> OTHER INFORMATION: zea mays BT2 protein

<400> SEQUENCE: 2

```
Met Asp Met Ala Leu Ala Ser Lys Ala Ser Pro Pro Trp Asn Ala
1               5                   10                  15

Thr Ala Glu Gln Pro Ile Pro Lys Arg Asp Lys Ala Ala Asn
            20                  25                  30

Asp Ser Thr Tyr Leu Asn Pro Gln Ala His Asp Ser Val Leu Gly Ile
        35                  40                  45

Ile Leu Gly Gly Gly Ala Gly Thr Arg Leu Tyr Pro Leu Thr Lys Lys
    50                  55                  60

Arg Ala Lys Pro Ala Val Pro Leu Gly Ala Asn Tyr Arg Leu Ile Asp
65                  70                  75                  80

Ile Pro Val Ser Asn Cys Leu Asn Ser Asn Ile Ser Lys Ile Tyr Val
                85                  90                  95

Leu Thr Gln Phe Asn Ser Ala Ser Leu Asn Arg His Leu Ser Arg Ala
            100                 105                 110

Tyr Gly Ser Asn Ile Gly Gly Tyr Lys Asn Glu Gly Phe Val Glu Val
        115                 120                 125

Leu Ala Ala Gln Gln Ser Pro Asp Asn Pro Asn Trp Phe Gln Gly Thr
    130                 135                 140

Ala Asp Ala Val Arg Gln Tyr Leu Trp Leu Phe Glu Glu His Asn Val
145                 150                 155                 160

Met Glu Phe Leu Ile Leu Ala Gly Asp His Leu Tyr Arg Met Asp Tyr
                165                 170                 175

Glu Lys Phe Ile Gln Ala His Arg Glu Thr Asn Ala Asp Ile Thr Val
            180                 185                 190

Ala Ala Leu Pro Met Asp Glu Lys Arg Ala Thr Ala Phe Gly Leu Met
        195                 200                 205

Lys Ile Asp Glu Glu Gly Arg Ile Ile Glu Phe Ala Glu Lys Pro Lys
    210                 215                 220

Gly Glu Gln Leu Lys Ala Met Met Val Asp Thr Thr Ile Leu Gly Leu
225                 230                 235                 240

Asp Asp Val Arg Ala Lys Glu Met Pro Tyr Ile Ala Ser Met Gly Ile
                245                 250                 255

Tyr Val Phe Ser Lys Asp Val Met Leu Gln Leu Leu Arg Glu Gln Phe
            260                 265                 270

Pro Glu Ala Asn Asp Phe Gly Ser Glu Val Ile Pro Gly Ala Thr Ser
        275                 280                 285
```

```
Ile Gly Lys Arg Val Gln Ala Tyr Leu Tyr Asp Gly Tyr Trp Glu Asp
            290                 295                 300
Ile Gly Thr Ile Ala Ala Phe Tyr Asn Ala Asn Leu Gly Ile Thr Lys
305                 310                 315                 320
Lys Pro Ile Pro Asp Phe Ser Phe Tyr Asp Arg Phe Ala Pro Ile Tyr
                325                 330                 335
Thr Gln Pro Arg His Leu Pro Pro Ser Lys Val Leu Asp Ala Asp Val
            340                 345                 350
Thr Asp Ser Val Ile Gly Glu Gly Cys Val Ile Lys Asn Cys Lys Ile
        355                 360                 365
Asn His Ser Val Val Gly Leu Arg Ser Cys Ile Ser Glu Gly Ala Ile
    370                 375                 380
Ile Glu Asp Ser Leu Leu Met Gly Ala Asp Tyr Tyr Glu Thr Glu Ala
385                 390                 395                 400
Asp Lys Lys Leu Leu Ala Glu Lys Gly Gly Ile Pro Ile Gly Ile Gly
                405                 410                 415
Lys Asn Ser Cys Ile Arg Arg Ala Ile Ile Asp Lys Asn Ala Arg Ile
            420                 425                 430
Gly Asp Asn Val Lys Ile Leu Asn Ala Asp Asn Val Gln Glu Ala Ala
        435                 440                 445
Met Glu Thr Asp Gly Tyr Phe Ile Lys Gly Ile Val Ile Val Ile
    450                 455                 460
Lys Asp Ala Leu Leu Pro Ser Gly Thr Val Ile
465                 470                 475

<210> SEQ ID NO 3
<211> LENGTH: 1425
<212> TYPE: DNA
<213> ORGANISM: Artificial Sequence
<220> FEATURE:
<223> OTHER INFORMATION: zea mays MP-TI nucleotide

<400> SEQUENCE: 3
atggacatgg ctttggcgtc taaagcctcc cctccgccat ggaatgccac cgccgccgag     60
cagccaattc caaagcgtga caaagccgct gcaaatgatt caacatacct caatcctcaa    120
gctcatgata gtgttcttgg aatcattctg ggaggtggtg ctgggactag attgtaccc     180
ttgacaaaga agcgtgccaa gcctgcagtg ccattgggtg ccaactatag actgattgat    240
attcctgtca gcaattgtct caacagcaac atatccaaga tctatgtgct aacgcaattt    300
aactctgctt ccctcaaccg tcacctctca agagcctacg ggagcaacat ggagggtac    360
aagaatgaag ggtttgttga agtcttagct gcacagcaga gcccagataa tccaaactgg    420
tttcagggta ctgcagatgc tgtaaggcag tacttgtggt tgtttgagga gcataatgtg    480
atggaatttc taattcttgc tggcgatcac ctgtaccgga tggactatga aaagttcatt    540
caggcacaca gagaaacaaa tgctgatatt accgttgctg ccctaccgat ggatgagaag    600
cgtgccactg catttggtct catgaagatt gacgaagaag gacgcattat tgaatttgca    660
gagaaaccgc aaggagagca attgcaagca atgaaagtgg atactaccat tttaggtctt    720
gatgacaaga gagctaaaga aatgcctttc attgccagta tgggtatata tgtcattagc    780
aaagacgtga tgttaaacct acttcgtgac aagttccctg ggccaatga ttttggtagt    840
gaagttattc ctggtgcaac ttcacttggg atgagagtgc aagcttattt atatgatggg    900
tactgggaag atattggtac cattgaagct ttctacaatg ccaatttggg cattacaaaa    960
aagccggtgc cagattttag cttttacgac cgatcagccc caatctacac ccaacctcga   1020
```

```
tatctaccac catcaaaaat gcttgatgct gatgtcacag atagtgtcat tggtgaaggt    1080
tgtgtgatca agaactgtaa gattcatcat tccgtggttg gactcagatc atgcatatca    1140 gaggagcaa ttatagaaga ctcactttg atggggcag attactatga gactgatgct      1200
gacaggaagt tgttggctgc aaagggcagt gtcccaattg gcatcggcaa gaattgtcac    1260
attaaaagag ccattatcga caagaatgcc cgtatagggg acaatgtgaa gatcattaac    1320
aaagacaacg ttcaagaagc ggctagggaa acagatggat acttcatcaa gagtgggatt    1380
gtcatcgtca tcaaggatgc tttgattcca agtggaatca tcatc                   1425
```

<210> SEQ ID NO 4
<211> LENGTH: 475
<212> TYPE: PRT
<213> ORGANISM: Artificial Sequence
<220> FEATURE:
<223> OTHER INFORMATION: zea mays MP-TI protein

<400> SEQUENCE: 4

```
Met Asp Met Ala Leu Ala Ser Lys Ala Ser Pro Pro Trp Asn Ala
1               5                   10                  15

Thr Ala Ala Glu Gln Pro Ile Pro Lys Arg Asp Lys Ala Ala Asn
                20                  25                  30

Asp Ser Thr Tyr Leu Asn Pro Gln Ala His Asp Ser Val Leu Gly Ile
                35                  40                  45

Ile Leu Gly Gly Gly Ala Gly Thr Arg Leu Tyr Pro Leu Thr Lys Lys
        50                  55                  60

Arg Ala Lys Pro Ala Val Pro Leu Gly Ala Asn Tyr Arg Leu Ile Asp
65                  70                  75                  80

Ile Pro Val Ser Asn Cys Leu Asn Ser Asn Ile Ser Lys Ile Tyr Val
                85                  90                  95

Leu Thr Gln Phe Asn Ser Ala Ser Leu Asn Arg His Leu Ser Arg Ala
                100                 105                 110

Tyr Gly Ser Asn Ile Gly Gly Tyr Lys Asn Glu Gly Phe Val Glu Val
        115                 120                 125

Leu Ala Ala Gln Gln Ser Pro Asp Asn Pro Asn Trp Phe Gln Gly Thr
    130                 135                 140

Ala Asp Ala Val Arg Gln Tyr Leu Trp Leu Phe Glu Glu His Asn Val
145                 150                 155                 160

Met Glu Phe Leu Ile Leu Ala Gly Asp His Leu Tyr Arg Met Asp Tyr
                165                 170                 175

Glu Lys Phe Ile Gln Ala His Arg Glu Thr Asn Ala Asp Ile Thr Val
        180                 185                 190

Ala Ala Leu Pro Met Asp Glu Lys Arg Ala Thr Ala Phe Gly Leu Met
            195                 200                 205

Lys Ile Asp Glu Glu Gly Arg Ile Ile Glu Phe Ala Glu Lys Pro Gln
    210                 215                 220

Gly Glu Gln Leu Gln Ala Met Lys Val Asp Thr Thr Ile Leu Gly Leu
225                 230                 235                 240

Asp Asp Lys Arg Ala Lys Glu Met Pro Phe Ile Ala Ser Met Gly Ile
                245                 250                 255

Tyr Val Ile Ser Lys Asp Val Met Leu Asn Leu Leu Arg Asp Lys Phe
            260                 265                 270

Pro Gly Ala Asn Asp Phe Gly Ser Glu Val Ile Pro Gly Ala Thr Ser
        275                 280                 285

Leu Gly Met Arg Val Gln Ala Tyr Leu Tyr Asp Gly Tyr Trp Glu Asp
```

```
                    290                 295                 300
Ile Gly Thr Ile Glu Ala Phe Tyr Asn Ala Asn Leu Gly Ile Thr Lys
305                 310                 315                 320

Lys Pro Val Pro Asp Phe Ser Phe Tyr Asp Arg Ser Ala Pro Ile Tyr
                325                 330                 335

Thr Gln Pro Arg Tyr Leu Pro Pro Ser Lys Met Leu Asp Ala Asp Val
                340                 345                 350

Thr Asp Ser Val Ile Gly Glu Gly Cys Val Ile Lys Asn Cys Lys Ile
                355                 360                 365

His His Ser Val Val Gly Leu Arg Ser Cys Ile Ser Glu Gly Ala Ile
                370                 375                 380

Ile Glu Asp Ser Leu Leu Met Gly Ala Asp Tyr Tyr Glu Thr Asp Ala
385                 390                 395                 400

Asp Arg Lys Leu Leu Ala Ala Lys Gly Ser Val Pro Ile Gly Ile Gly
                405                 410                 415

Lys Asn Cys His Ile Lys Arg Ala Ile Ile Asp Lys Asn Ala Arg Ile
                420                 425                 430

Gly Asp Asn Val Lys Ile Ile Asn Lys Asp Asn Val Gln Glu Ala Ala
                435                 440                 445

Arg Glu Thr Asp Gly Tyr Phe Ile Lys Ser Gly Ile Val Ile Val Ile
                450                 455                 460

Lys Asp Ala Leu Ile Pro Ser Gly Ile Ile Ile
465                 470                 475

<210> SEQ ID NO 5
<211> LENGTH: 475
<212> TYPE: PRT
<213> ORGANISM: Artificial Sequence
<220> FEATURE:
<223> OTHER INFORMATION: zea mays BT2 protein

<400> SEQUENCE: 5

Met Asp Met Ala Leu Ala Ser Lys Ala Ser Pro Pro Trp Asn Ala
1               5                   10                  15

Thr Ala Glu Gln Pro Ile Pro Lys Arg Asp Lys Ala Ala Asn
                20                  25                  30

Asp Ser Thr Cys Leu Asn Pro Gln Ala His Asp Ser Val Leu Gly Ile
                35                  40                  45

Ile Leu Gly Gly Gly Ala Gly Thr Arg Leu Tyr Pro Leu Thr Lys Lys
                50                  55                  60

Arg Ala Lys Pro Ala Val Pro Leu Gly Ala Asn Tyr Arg Leu Ile Asp
65                  70                  75                  80

Ile Pro Val Ser Asn Cys Leu Asn Ser Asn Ile Ser Lys Ile Tyr Val
                85                  90                  95

Leu Thr Gln Phe Asn Ser Ala Ser Leu Asn Arg His Leu Ser Arg Ala
                100                 105                 110

Tyr Gly Ser Asn Ile Gly Gly Tyr Lys Asn Glu Gly Phe Val Glu Val
                115                 120                 125

Leu Ala Ala Gln Gln Ser Pro Asp Asn Pro Asn Trp Phe Gln Gly Thr
                130                 135                 140

Ala Asp Ala Val Arg Gln Tyr Leu Trp Leu Phe Glu Glu His Asn Val
145                 150                 155                 160

Met Glu Phe Leu Ile Leu Ala Gly Asp His Leu Tyr Arg Met Asp Tyr
                165                 170                 175

Glu Lys Phe Ile Gln Ala His Arg Glu Thr Asn Ala Asp Ile Thr Val
                180                 185                 190
```

```
Ala Ala Leu Pro Met Asp Glu Lys Arg Ala Thr Ala Phe Gly Leu Met
        195                 200                 205

Lys Ile Asp Glu Glu Gly Arg Ile Ile Glu Phe Ala Glu Lys Pro Lys
    210                 215                 220

Gly Glu Gln Leu Lys Ala Met Met Val Asp Thr Thr Ile Leu Gly Leu
225                 230                 235                 240

Asp Asp Val Arg Ala Lys Glu Met Pro Tyr Ile Ala Ser Met Gly Ile
                245                 250                 255

Tyr Val Phe Ser Lys Asp Val Met Leu Gln Leu Leu Arg Glu Gln Phe
                260                 265                 270

Pro Glu Ala Asn Asp Phe Gly Ser Glu Val Ile Pro Gly Ala Thr Ser
            275                 280                 285

Ile Gly Lys Arg Val Gln Ala Tyr Leu Tyr Asp Gly Tyr Trp Glu Asp
        290                 295                 300

Ile Gly Thr Ile Ala Ala Phe Tyr Asn Ala Asn Leu Gly Ile Thr Lys
305                 310                 315                 320

Lys Pro Ile Pro Asp Phe Ser Phe Tyr Asp Arg Phe Ala Pro Ile Tyr
                325                 330                 335

Thr Gln Pro Arg His Leu Pro Pro Ser Lys Val Leu Asp Ala Asp Val
                340                 345                 350

Thr Asp Ser Val Ile Gly Glu Gly Cys Val Ile Lys Asn Cys Lys Ile
            355                 360                 365

Asn His Ser Val Val Gly Leu Arg Ser Cys Ile Ser Glu Gly Ala Ile
        370                 375                 380

Ile Glu Asp Ser Leu Leu Met Gly Ala Asp Tyr Tyr Glu Thr Glu Ala
385                 390                 395                 400

Asp Lys Lys Leu Leu Ala Glu Lys Gly Ile Pro Ile Gly Ile Gly Gly
                405                 410                 415

Lys Asn Ser Cys Ile Arg Arg Ala Ile Ile Asp Lys Asn Ala Arg Ile
            420                 425                 430

Gly Asp Asn Val Lys Ile Leu Asn Ala Asp Asn Val Gln Glu Ala Ala
        435                 440                 445

Met Glu Thr Asp Gly Tyr Phe Ile Lys Gly Gly Ile Val Ile Val Ile
    450                 455                 460

Lys Asp Ala Leu Leu Pro Ser Gly Thr Val Ile
465                 470                 475

<210> SEQ ID NO 6
<211> LENGTH: 476
<212> TYPE: PRT
<213> ORGANISM: Artificial Sequence
<220> FEATURE:
<223> OTHER INFORMATION: zea mays BT2 protein

<400> SEQUENCE: 6

Met Asp Met Ala Leu Ala Ser Lys Ala Ser Pro Pro Trp Asn Ala
1               5                   10                  15

Thr Ala Glu Gln Pro Ile Pro Lys Arg Asp Lys Ala Ala Ala Asn
                20                  25                  30

Asp Ser Gln Thr Cys Leu Asn Pro Gln Ala His Asp Ser Val Leu Gly
            35                  40                  45

Ile Ile Leu Gly Gly Gly Ala Gly Thr Arg Leu Tyr Pro Leu Thr Lys
        50                  55                  60

Lys Arg Ala Lys Pro Ala Val Pro Leu Gly Ala Asn Tyr Arg Leu Ile
65                  70                  75                  80
```

-continued

```
Asp Ile Pro Val Ser Asn Cys Leu Asn Ser Asn Ile Ser Lys Ile Tyr
                85                  90                  95
Val Leu Thr Gln Phe Asn Ser Ala Ser Leu Asn Arg His Leu Ser Arg
            100                 105                 110
Ala Tyr Gly Ser Asn Ile Gly Gly Tyr Lys Asn Glu Gly Phe Val Glu
        115                 120                 125
Val Leu Ala Ala Gln Gln Ser Pro Asp Asn Pro Asn Trp Phe Gln Gly
    130                 135                 140
Thr Ala Asp Ala Val Arg Gln Tyr Leu Trp Leu Phe Glu Glu His Asn
145                 150                 155                 160
Val Met Glu Phe Leu Ile Leu Ala Gly Asp His Leu Tyr Arg Met Asp
                165                 170                 175
Tyr Glu Lys Phe Ile Gln Ala His Arg Glu Thr Asn Ala Asp Ile Thr
            180                 185                 190
Val Ala Ala Leu Pro Met Asp Glu Lys Arg Ala Thr Ala Phe Gly Leu
        195                 200                 205
Met Lys Ile Asp Glu Glu Gly Arg Ile Ile Glu Phe Ala Glu Lys Pro
    210                 215                 220
Lys Gly Glu Gln Leu Lys Ala Met Met Val Asp Thr Thr Ile Leu Gly
225                 230                 235                 240
Leu Asp Asp Val Arg Ala Lys Glu Met Pro Tyr Ile Ala Ser Met Gly
                245                 250                 255
Ile Tyr Val Phe Ser Lys Asp Val Met Leu Gln Leu Leu Arg Glu Gln
            260                 265                 270
Phe Pro Glu Ala Asn Asp Phe Gly Ser Glu Val Ile Pro Gly Ala Thr
        275                 280                 285
Ser Ile Gly Lys Arg Val Gln Ala Tyr Leu Tyr Asp Gly Tyr Trp Glu
    290                 295                 300
Asp Ile Gly Thr Ile Ala Ala Phe Tyr Asn Ala Asn Leu Gly Ile Thr
305                 310                 315                 320
Lys Lys Pro Ile Pro Asp Phe Ser Phe Tyr Asp Arg Phe Ala Pro Ile
                325                 330                 335
Tyr Thr Gln Pro Arg His Leu Pro Pro Ser Lys Val Leu Asp Ala Asp
            340                 345                 350
Val Thr Asp Ser Val Ile Gly Glu Gly Cys Val Ile Lys Asn Cys Lys
        355                 360                 365
Ile Asn His Ser Val Val Gly Leu Arg Ser Cys Ile Ser Glu Gly Ala
    370                 375                 380
Ile Ile Glu Asp Ser Leu Leu Met Gly Ala Asp Tyr Tyr Glu Thr Glu
385                 390                 395                 400
Ala Asp Lys Lys Leu Leu Ala Glu Lys Gly Gly Ile Pro Ile Gly Ile
                405                 410                 415
Gly Lys Asn Ser Cys Ile Arg Arg Ala Ile Ile Asp Lys Asn Ala Arg
            420                 425                 430
Ile Gly Asp Asn Val Lys Ile Leu Asn Ala Asp Asn Val Gln Glu Ala
        435                 440                 445
Ala Met Glu Thr Asp Gly Tyr Phe Ile Lys Gly Ile Val Ile Val
    450                 455                 460
Ile Lys Asp Ala Leu Leu Pro Ser Gly Thr Val Ile
465                 470                 475

<210> SEQ ID NO 7
<211> LENGTH: 476
<212> TYPE: PRT
<213> ORGANISM: Artificial Sequence
```

```
<220> FEATURE:
<223> OTHER INFORMATION: zea mays BT2 protein

<400> SEQUENCE: 7

Met Asp Met Ala Leu Ala Ser Lys Ala Ser Pro Pro Trp Asn Ala
1               5                   10                  15

Thr Ala Ala Glu Gln Pro Ile Pro Lys Arg Asp Lys Ala Ala Asn
                20                  25                  30

Asp Ser Glu Thr Cys Leu Asn Pro Gln Ala His Asp Ser Val Leu Gly
            35                  40                  45

Ile Ile Leu Gly Gly Gly Ala Gly Thr Arg Leu Tyr Pro Leu Thr Lys
50                  55                      60

Lys Arg Ala Lys Pro Ala Val Pro Leu Gly Ala Asn Tyr Arg Leu Ile
65              70                  75                  80

Asp Ile Pro Val Ser Asn Cys Leu Asn Ser Asn Ile Ser Lys Ile Tyr
                85                  90                  95

Val Leu Thr Gln Phe Asn Ser Ala Ser Leu Asn Arg His Leu Ser Arg
                100                 105                 110

Ala Tyr Gly Ser Asn Ile Gly Gly Tyr Lys Asn Glu Gly Phe Val Glu
            115                 120                 125

Val Leu Ala Ala Gln Gln Ser Pro Asp Asn Pro Asn Trp Phe Gln Gly
130                 135                 140

Thr Ala Asp Ala Val Arg Gln Tyr Leu Trp Leu Phe Glu Glu His Asn
145                 150                 155                 160

Val Met Glu Phe Leu Ile Leu Ala Gly Asp His Leu Tyr Arg Met Asp
                165                 170                 175

Tyr Glu Lys Phe Ile Gln Ala His Arg Glu Thr Asn Ala Asp Ile Thr
            180                 185                 190

Val Ala Ala Leu Pro Met Asp Glu Lys Arg Ala Thr Ala Phe Gly Leu
            195                 200                 205

Met Lys Ile Asp Glu Glu Gly Arg Ile Ile Glu Phe Ala Glu Lys Pro
210                 215                 220

Lys Gly Glu Gln Leu Lys Ala Met Met Val Asp Thr Thr Ile Leu Gly
225                 230                 235                 240

Leu Asp Asp Val Arg Ala Lys Glu Met Pro Tyr Ile Ala Ser Met Gly
                245                 250                 255

Ile Tyr Val Phe Ser Lys Asp Val Met Leu Gln Leu Leu Arg Glu Gln
                260                 265                 270

Phe Pro Glu Ala Asn Asp Phe Gly Ser Glu Val Ile Pro Gly Ala Thr
            275                 280                 285

Ser Ile Gly Lys Arg Val Gln Ala Tyr Leu Tyr Asp Gly Tyr Trp Glu
290                 295                 300

Asp Ile Gly Thr Ile Ala Ala Phe Tyr Asn Ala Asn Leu Gly Ile Thr
305                 310                 315                 320

Lys Lys Pro Ile Pro Asp Phe Ser Phe Tyr Asp Arg Phe Ala Pro Ile
                325                 330                 335

Tyr Thr Gln Pro Arg His Leu Pro Pro Ser Lys Val Leu Asp Ala Asp
                340                 345                 350

Val Thr Asp Ser Val Ile Gly Glu Gly Cys Val Ile Lys Asn Cys Lys
            355                 360                 365

Ile Asn His Ser Val Val Gly Leu Arg Ser Cys Ile Ser Glu Gly Ala
            370                 375                 380

Ile Ile Glu Asp Ser Leu Leu Met Gly Ala Asp Tyr Tyr Glu Thr Glu
385                 390                 395                 400
```

-continued

Ala Asp Lys Lys Leu Leu Ala Glu Lys Gly Gly Ile Pro Ile Gly Ile
            405                 410                 415

Gly Lys Asn Ser Cys Ile Arg Arg Ala Ile Ile Asp Lys Asn Ala Arg
                420                 425                 430

Ile Gly Asp Asn Val Lys Ile Leu Asn Ala Asp Asn Val Gln Glu Ala
            435                 440                 445

Ala Met Glu Thr Asp Gly Tyr Phe Ile Lys Gly Ile Val Ile Val
    450                 455                 460

Ile Lys Asp Ala Leu Leu Pro Ser Gly Thr Val Ile
465                 470                 475

<210> SEQ ID NO 8
<211> LENGTH: 475
<212> TYPE: PRT
<213> ORGANISM: Artificial Sequence
<220> FEATURE:
<223> OTHER INFORMATION: zea mays MP-TI protein

<400> SEQUENCE: 8

Met Asp Met Ala Leu Ala Ser Lys Ala Ser Pro Pro Trp Asn Ala
1               5                   10                  15

Thr Ala Ala Glu Gln Pro Ile Pro Lys Arg Asp Lys Ala Ala Asn
                20                  25                  30

Asp Ser Thr Cys Leu Asn Pro Gln Ala His Asp Ser Val Leu Gly Ile
            35                  40                  45

Ile Leu Gly Gly Gly Ala Gly Thr Arg Leu Tyr Pro Leu Thr Lys Lys
    50                  55                  60

Arg Ala Lys Pro Ala Val Pro Leu Gly Ala Asn Tyr Arg Leu Ile Asp
65              70                  75                  80

Ile Pro Val Ser Asn Cys Leu Asn Ser Asn Ile Ser Lys Ile Tyr Val
                85                  90                  95

Leu Thr Gln Phe Asn Ser Ala Ser Leu Asn Arg His Leu Ser Arg Ala
            100                 105                 110

Tyr Gly Ser Asn Ile Gly Gly Tyr Lys Asn Glu Gly Phe Val Glu Val
        115                 120                 125

Leu Ala Ala Gln Gln Ser Pro Asp Asn Pro Asn Trp Phe Gln Gly Thr
    130                 135                 140

Ala Asp Ala Val Arg Gln Tyr Leu Trp Leu Phe Glu Glu His Asn Val
145                 150                 155                 160

Met Glu Phe Leu Ile Leu Ala Gly Asp His Leu Tyr Arg Met Asp Tyr
                165                 170                 175

Glu Lys Phe Ile Gln Ala His Arg Glu Thr Asn Ala Asp Ile Thr Val
            180                 185                 190

Ala Ala Leu Pro Met Asp Glu Lys Arg Ala Thr Ala Phe Gly Leu Met
        195                 200                 205

Lys Ile Asp Glu Glu Gly Arg Ile Ile Glu Phe Ala Glu Lys Pro Gln
    210                 215                 220

Gly Glu Gln Leu Gln Ala Met Lys Val Asp Thr Thr Ile Leu Gly Leu
225                 230                 235                 240

Asp Asp Lys Arg Ala Lys Glu Met Pro Phe Ile Ala Ser Met Gly Ile
                245                 250                 255

Tyr Val Ile Ser Lys Asp Val Met Leu Asn Leu Leu Arg Asp Lys Phe
            260                 265                 270

Pro Gly Ala Asn Asp Phe Gly Ser Glu Val Ile Pro Gly Ala Thr Ser
        275                 280                 285

Leu Gly Met Arg Val Gln Ala Tyr Leu Tyr Asp Gly Tyr Trp Glu Asp

```
                 290                 295                 300
Ile Gly Thr Ile Glu Ala Phe Tyr Asn Ala Asn Leu Gly Ile Thr Lys
305                 310                 315                 320

Lys Pro Val Pro Asp Phe Ser Phe Tyr Asp Arg Ser Ala Pro Ile Tyr
                325                 330                 335

Thr Gln Pro Arg Tyr Leu Pro Pro Ser Lys Met Leu Asp Ala Asp Val
                340                 345                 350

Thr Asp Ser Val Ile Gly Glu Gly Cys Val Ile Lys Asn Cys Lys Ile
                355                 360                 365

His His Ser Val Val Gly Leu Arg Ser Cys Ile Ser Glu Gly Ala Ile
                370                 375                 380

Ile Glu Asp Ser Leu Leu Met Gly Ala Asp Tyr Tyr Glu Thr Asp Ala
385                 390                 395                 400

Asp Arg Lys Leu Leu Ala Ala Lys Gly Ser Val Pro Ile Gly Ile Gly
                405                 410                 415

Lys Asn Cys His Ile Lys Arg Ala Ile Ile Asp Lys Asn Ala Arg Ile
                420                 425                 430

Gly Asp Asn Val Lys Ile Ile Asn Lys Asp Asn Val Gln Glu Ala Ala
                435                 440                 445

Arg Glu Thr Asp Gly Tyr Phe Ile Lys Ser Gly Ile Val Ile Val Ile
                450                 455                 460

Lys Asp Ala Leu Ile Pro Ser Gly Ile Ile Ile
465                 470                 475

<210> SEQ ID NO 9
<211> LENGTH: 476
<212> TYPE: PRT
<213> ORGANISM: Artificial Sequence
<220> FEATURE:
<223> OTHER INFORMATION: zea mays MP-TI protein

<400> SEQUENCE: 9

Met Asp Met Ala Leu Ala Ser Lys Ala Ser Pro Pro Trp Asn Ala
1               5                   10                  15

Thr Ala Ala Glu Gln Pro Ile Pro Lys Arg Asp Lys Ala Ala Asn
                20                  25                  30

Asp Ser Gln Thr Cys Leu Asn Pro Gln Ala His Asp Ser Val Leu Gly
                35                  40                  45

Ile Ile Leu Gly Gly Gly Ala Gly Thr Arg Leu Tyr Pro Leu Thr Lys
50                  55                  60

Lys Arg Ala Lys Pro Ala Val Pro Leu Gly Ala Asn Tyr Arg Leu Ile
65                  70                  75                  80

Asp Ile Pro Val Ser Asn Cys Leu Asn Ser Asn Ile Ser Lys Ile Tyr
                85                  90                  95

Val Leu Thr Gln Phe Asn Ser Ala Ser Leu Asn Arg His Leu Ser Arg
                100                 105                 110

Ala Tyr Gly Ser Asn Ile Gly Gly Tyr Lys Asn Glu Gly Phe Val Glu
                115                 120                 125

Val Leu Ala Ala Gln Gln Ser Pro Asp Asn Pro Asn Trp Phe Gln Gly
                130                 135                 140

Thr Ala Asp Ala Val Arg Gln Tyr Leu Trp Leu Phe Glu Glu His Asn
145                 150                 155                 160

Val Met Glu Phe Leu Ile Leu Ala Gly Asp His Leu Tyr Arg Met Asp
                165                 170                 175

Tyr Glu Lys Phe Ile Gln Ala His Arg Glu Thr Asn Ala Asp Ile Thr
                180                 185                 190
```

```
Val Ala Ala Leu Pro Met Asp Glu Lys Arg Ala Thr Ala Phe Gly Leu
            195                 200                 205

Met Lys Ile Asp Glu Glu Gly Arg Ile Ile Glu Phe Ala Glu Lys Pro
            210                 215                 220

Gln Gly Glu Gln Leu Gln Ala Met Lys Val Asp Thr Thr Ile Leu Gly
225                 230                 235                 240

Leu Asp Asp Lys Arg Ala Lys Glu Met Pro Phe Ile Ala Ser Met Gly
                    245                 250                 255

Ile Tyr Val Ile Ser Lys Asp Val Met Leu Asn Leu Leu Arg Asp Lys
            260                 265                 270

Phe Pro Gly Ala Asn Asp Phe Gly Ser Glu Val Ile Pro Gly Ala Thr
            275                 280                 285

Ser Leu Gly Met Arg Val Gln Ala Tyr Leu Tyr Asp Gly Tyr Trp Glu
            290                 295                 300

Asp Ile Gly Thr Ile Glu Ala Phe Tyr Asn Ala Asn Leu Gly Ile Thr
305                 310                 315                 320

Lys Lys Pro Val Pro Asp Phe Ser Phe Tyr Asp Arg Ser Ala Pro Ile
                    325                 330                 335

Tyr Thr Gln Pro Arg Tyr Leu Pro Pro Ser Lys Met Leu Asp Ala Asp
            340                 345                 350

Val Thr Asp Ser Val Ile Gly Glu Gly Cys Val Ile Lys Asn Cys Lys
            355                 360                 365

Ile His His Ser Val Val Gly Leu Arg Ser Cys Ile Ser Glu Gly Ala
            370                 375                 380

Ile Ile Glu Asp Ser Leu Leu Met Gly Ala Asp Tyr Tyr Glu Thr Asp
385                 390                 395                 400

Ala Asp Arg Lys Leu Leu Ala Ala Lys Gly Ser Val Pro Ile Gly Ile
                    405                 410                 415

Gly Lys Asn Cys His Ile Lys Arg Ala Ile Ile Asp Lys Asn Ala Arg
            420                 425                 430

Ile Gly Asp Asn Val Lys Ile Ile Asn Lys Asp Asn Val Gln Glu Ala
            435                 440                 445

Ala Arg Glu Thr Asp Gly Tyr Phe Ile Lys Ser Gly Ile Val Ile Val
            450                 455                 460

Ile Lys Asp Ala Leu Ile Pro Ser Gly Ile Ile Ile
465                 470                 475

<210> SEQ ID NO 10
<211> LENGTH: 476
<212> TYPE: PRT
<213> ORGANISM: Artificial Sequence
<220> FEATURE:
<223> OTHER INFORMATION: zea mays MP-TI protein

<400> SEQUENCE: 10

Met Asp Met Ala Leu Ala Ser Lys Ala Ser Pro Pro Trp Asn Ala
1               5                   10                  15

Thr Ala Ala Glu Gln Pro Ile Pro Lys Arg Asp Lys Ala Ala Ala Asn
            20                  25                  30

Asp Ser Glu Thr Cys Leu Asn Pro Gln Ala His Asp Ser Val Leu Gly
            35                  40                  45

Ile Ile Leu Gly Gly Gly Ala Gly Thr Arg Leu Tyr Pro Leu Thr Lys
            50                  55                  60

Lys Arg Ala Lys Pro Ala Val Pro Leu Gly Ala Asn Tyr Arg Leu Ile
65                  70                  75                  80
```

Asp Ile Pro Val Ser Asn Cys Leu Asn Ser Asn Ile Ser Lys Ile Tyr
                85                  90                  95

Val Leu Thr Gln Phe Asn Ser Ala Ser Leu Asn Arg His Leu Ser Arg
            100                 105                 110

Ala Tyr Gly Ser Asn Ile Gly Gly Tyr Lys Asn Glu Gly Phe Val Glu
            115                 120                 125

Val Leu Ala Ala Gln Gln Ser Pro Asp Asn Pro Asn Trp Phe Gln Gly
            130                 135                 140

Thr Ala Asp Ala Val Arg Gln Tyr Leu Trp Leu Phe Glu Glu His Asn
145                 150                 155                 160

Val Met Glu Phe Leu Ile Leu Ala Gly Asp His Leu Tyr Arg Met Asp
                165                 170                 175

Tyr Glu Lys Phe Ile Gln Ala His Arg Glu Thr Asn Ala Asp Ile Thr
                180                 185                 190

Val Ala Ala Leu Pro Met Asp Glu Lys Arg Ala Thr Ala Phe Gly Leu
                195                 200                 205

Met Lys Ile Asp Glu Glu Gly Arg Ile Ile Glu Phe Ala Glu Lys Pro
210                 215                 220

Gln Gly Glu Gln Leu Gln Ala Met Lys Val Asp Thr Thr Ile Leu Gly
225                 230                 235                 240

Leu Asp Asp Lys Arg Ala Lys Glu Met Pro Phe Ile Ala Ser Met Gly
                245                 250                 255

Ile Tyr Val Ile Ser Lys Asp Val Met Leu Asn Leu Leu Arg Asp Lys
                260                 265                 270

Phe Pro Gly Ala Asn Asp Phe Gly Ser Glu Val Ile Pro Gly Ala Thr
                275                 280                 285

Ser Leu Gly Met Arg Val Gln Ala Tyr Leu Tyr Asp Gly Tyr Trp Glu
            290                 295                 300

Asp Ile Gly Thr Ile Glu Ala Phe Tyr Asn Ala Asn Leu Gly Ile Thr
305                 310                 315                 320

Lys Lys Pro Val Pro Asp Phe Ser Phe Tyr Asp Arg Ser Ala Pro Ile
                325                 330                 335

Tyr Thr Gln Pro Arg Tyr Leu Pro Pro Ser Lys Met Leu Asp Ala Asp
            340                 345                 350

Val Thr Asp Ser Val Ile Gly Glu Gly Cys Val Ile Lys Asn Cys Lys
            355                 360                 365

Ile His His Ser Val Val Gly Leu Arg Ser Cys Ile Ser Glu Gly Ala
            370                 375                 380

Ile Ile Glu Asp Ser Leu Leu Met Gly Ala Asp Tyr Tyr Glu Thr Asp
385                 390                 395                 400

Ala Asp Arg Lys Leu Leu Ala Ala Lys Gly Ser Val Pro Ile Gly Ile
                405                 410                 415

Gly Lys Asn Cys His Ile Lys Arg Ala Ile Ile Asp Lys Asn Ala Arg
            420                 425                 430

Ile Gly Asp Asn Val Lys Ile Ile Asn Lys Asp Asn Val Gln Glu Ala
            435                 440                 445

Ala Arg Glu Thr Asp Gly Tyr Phe Ile Lys Ser Gly Ile Val Ile Val
            450                 455                 460

Ile Lys Asp Ala Leu Ile Pro Ser Gly Ile Ile Ile
465                 470                 475

<210> SEQ ID NO 11
<211> LENGTH: 1425
<212> TYPE: DNA
<213> ORGANISM: Artificial Sequence

```
<220> FEATURE:
<223> OTHER INFORMATION: zea mays Bt2 gene
<220> FEATURE:
<221> NAME/KEY: misc_feature
<222> LOCATION: (108)..(108)
<223> OTHER INFORMATION: y = t or c
<220> FEATURE:
<221> NAME/KEY: misc_feature
<222> LOCATION: (1386)..(1386)
<223> OTHER INFORMATION: h = a or c or t

<400> SEQUENCE: 11
atggacatgg ctttggcgtc taaagcctcc cctccgccat ggaatgccac cgccgccgag      60
cagccaattc caaagcgtga caaagccgct gcaaatgatt caacatgyct caatcctcaa     120
gctcatgata gtgttcttgg aatcattctg ggaggtggtg ctgggactag attgtacccc     180
ttgacaaaga agcgtgccaa gcctgcagtg ccattgggtg ccaactatag actgattgat     240
attcctgtca gcaattgtct caacagcaac atatccaaga tctatgtgct aacgcaattt     300
aactctgctt ccctcaaccg tcacctctca agagcctacg ggagcaacat tggagggtac     360
aagaatgaag ggtttgttga agtcttagct gcacagcaga gcccagataa tccaaactgg     420
tttcagggta ctgcagatgc tgtaaggcag tacttgtggt tgtttgagga gcataatgtg     480
atggaatttc taattcttgc tggcgatcac ctgtaccgga tggactatga aaagttcatt     540
caggcacaca gagaaacaaa tgctgatatt accgttgctg ccctaccgat ggatgagaaa     600
cgtgcaactg catttggcct catgaaaatt gatgaagaag ggaggatcat tgagtttgct     660
gagaaaccga aggagagca gttgaaagca atgatggttg acaccaccat acttggcctt     720
gatgacgtga gggcaaagga aatgccttat attgctagca tgggtatcta tgttttcagc     780
aaagatgtaa tgcttcagct cctccgtgaa caatttcctg aagccaatga ctttggaagt     840
gaggttattc caggtgcaac cagcattgga aagagggttc aggcttatct gtatgatggt     900
tactgggaag atatcggtac cattgcggca ttttataatg caaacttggg aataaccaag     960
aagccaatac cagatttcag cttctatgac cgttttgctc caatttatac acaacctcga    1020
cacctgccac cttcaaaggt tcttgatgct gatgtgacag acagtgttat tggtgaagga    1080
tgtgttatta aaactgcaa gataaaccat tctgtagttg gactccgatc ttgcatatct    1140
gaaggtgcta tcatagagga cagtttacta atgggtgcgg actactatga gacagaagct    1200
gataaaaaac tccttgccga aaaggtggc attcctattg gtattgggaa aaattcatgc    1260
atcaggagag caatcattga caagaatgct cgaattggag acaatgttaa gatactcaat    1320
gctgacaatg ttcaagaagc tgcaatggag acagacgggt acttcatcaa aggtggaatt    1380
gtcathgtga tcaaggatgc tttactccct agtggaacag ttata                    1425

<210> SEQ ID NO 12
<211> LENGTH: 1428
<212> TYPE: DNA
<213> ORGANISM: Artificial Sequence
<220> FEATURE:
<223> OTHER INFORMATION: zea mays Bt2 gene
<220> FEATURE:
<221> NAME/KEY: misc_feature
<222> LOCATION: (105)..(105)
<223> OTHER INFORMATION: r = g or a
<220> FEATURE:
<221> NAME/KEY: misc_feature
<222> LOCATION: (111)..(111)
<223> OTHER INFORMATION: y = t or c
<220> FEATURE:
<221> NAME/KEY: misc_feature
<222> LOCATION: (1389)..(1389)
<223> OTHER INFORMATION: h = a or c or t
```

```
<400> SEQUENCE: 12
atggacatgg ctttggcgtc taaagcctcc cctccgccat ggaatgccac cgccgccgag      60
cagccaattc caaagcgtga caaagccgct gcaaatgatt cacaracatg yctcaatcct     120
caagctcatg atagtgttct tggaatcatt ctgggaggtg gtgctgggac tagattgtac     180
cccttgacaa agaagcgtgc caagcctgca gtgccattgg gtgccaacta tagactgatt     240
gatattcctg tcagcaattg tctcaacagc aacatatcca agatctatgt gctaacgcaa     300
tttaactctg cttccctcaa ccgtcacctc tcaagagcct acgggagcaa cattggaggg     360
tacaagaatg aagggtttgt tgaagtctta gctgcacagc agagcccaga taatccaaac     420
tggtttcagg gtactgcaga tgctgtaagg cagtacttgt ggttgtttga ggagcataat     480
gtgatggaat ttctaattct tgctggcgat cacctgtacc ggatggacta tgaaaagttc     540
attcaggcac acagagaaac aaatgctgat attaccgttg ctgccctacc gatggatgag     600
aaacgtgcaa ctgcatttgg cctcatgaaa attgatgaag aagggaggat cattgagttt     660
gctgagaaac cgaaaggaga gcagttgaaa gcaatgatgg ttgacaccac catacttggc     720
cttgatgacg tgagggcaaa ggaaatgcct tatattgcta gcatgggtat ctatgttttc     780
agcaaagatg taatgcttca gctcctccgt gaacaatttc ctgaagccaa tgactttgga     840
agtgaggtta ttccaggtgc aaccagcatt ggaaagaggg ttcaggctta tctgtatgat     900
ggttactggg aagatatcgg taccattgcg gcattttata atgcaaactt gggaataacc     960
aagaagccaa taccagattt cagcttctat gaccgttttg ctccaattta tacacaacct    1020
cgacacctgc caccttcaaa ggttcttgat gctgatgtga cagacagtgt tattggtgaa    1080
ggatgtgtta ttaaaaactg caagataaac cattctgtag ttggactccg atcttgcata    1140
tctgaaggtg ctatcataga ggacagttta ctaatgggtg cggactacta tgagacagaa    1200
gctgataaaa aactccttgc cgaaaaaggt ggcattccta ttggtattgg gaaaaattca    1260
tgcatcagga gagcaatcat tgacaagaat gctcgaattg agacaatgt taagatactc    1320 aatgctgaca atgttcaaga agctgcaatg gagacagacg ggtacttcat caaaggtgga    1380
attgtcathg tgatcaagga tgctttactc cctagtggaa cagttata              1428

<210> SEQ ID NO 13
<211> LENGTH: 1428
<212> TYPE: DNA
<213> ORGANISM: Artificial Sequence
<220> FEATURE:
<223> OTHER INFORMATION: zea mays Bt2 gene
<220> FEATURE:
<221> NAME/KEY: misc_feature
<222> LOCATION: (105)..(105)
<223> OTHER INFORMATION: r = g or a
<220> FEATURE:
<221> NAME/KEY: misc_feature
<222> LOCATION: (111)..(111)
<223> OTHER INFORMATION: y = t or c
<220> FEATURE:
<221> NAME/KEY: misc_feature
<222> LOCATION: (1389)..(1389)
<223> OTHER INFORMATION: h = a or c or t

<400> SEQUENCE: 13
atggacatgg ctttggcgtc taaagcctcc cctccgccat ggaatgccac cgccgccgag      60
cagccaattc caaagcgtga caaagccgct gcaaatgatt cagaracatg yctcaatcct     120
caagctcatg atagtgttct tggaatcatt ctgggaggtg gtgctgggac tagattgtac     180
cccttgacaa agaagcgtgc caagcctgca gtgccattgg gtgccaacta tagactgatt     240
```

```
gatattcctg tcagcaattg tctcaacagc aacatatcca agatctatgt gctaacgcaa    300
tttaactctg cttccctcaa ccgtcacctc tcaagagcct acgggagcaa cattggaggg    360
tacaagaatg aagggtttgt tgaagtctta gctgcacagc agagcccaga taatccaaac    420
tggtttcagg gtactgcaga tgctgtaagg cagtacttgt ggttgtttga ggagcataat    480
gtgatggaat ttctaattct tgctggcgat cacctgtacc ggatggacta tgaaaagttc    540
attcaggcac acagagaaac aaatgctgat attaccgttg ctgccctacc gatggatgag    600
aaacgtgcaa ctgcatttgg cctcatgaaa attgatgaag aagggaggat cattgagttt    660
gctgagaaac cgaaaggaga gcagttgaaa gcaatgatgg ttgacaccac catacttggc    720
cttgatgacg tgagggcaaa ggaaatgcct tatattgcta gcatgggtat ctatgttttc    780
agcaaagatg taatgcttca gctcctccgt gaacaatttc ctgaagccaa tgactttgga    840
agtgaggtta ttccaggtgc aaccagcatt ggaaagaggg ttcaggctta tctgtatgat    900
ggttactggg aagatatcgg taccattgcg gcatttttata atgcaaactt gggaataacc    960
aagaagccaa taccagattt cagcttctat gaccgttttg ctccaattta tacacaacct   1020
cgacacctgc caccttcaaa ggttcttgat gctgatgtga cagacagtgt tattggtgaa   1080
ggatgtgtta ttaaaaactg caagataaac cattctgtag ttggactccg atcttgcata   1140
tctgaaggtg ctatcataga ggacagttta ctaatgggtg cggactacta tgagacagaa   1200
gctgataaaa aactccttgc cgaaaaaggt ggcattccta ttggtattgg gaaaaattca   1260
tgcatcagga gagcaatcat tgacaagaat gctcgaattg gagacaatgt taagatactc   1320
aatgctgaca atgttcaaga agctgcaatg gagacagacg ggtacttcat caaaggtgga   1380
attgtcathg tgatcaagga tgctttactc cctagtggaa cagttata              1428

<210> SEQ ID NO 14
<211> LENGTH: 1425
<212> TYPE: DNA
<213> ORGANISM: Artificial Sequence
<220> FEATURE:
<223> OTHER INFORMATION: zea mays MP-TI nucleotide
<220> FEATURE:
<221> NAME/KEY: misc_feature
<222> LOCATION: (108)..(108)
<223> OTHER INFORMATION: y = t or c
<220> FEATURE:
<221> NAME/KEY: misc_feature
<222> LOCATION: (1386)..(1386)
<223> OTHER INFORMATION: h = a or c or t

<400> SEQUENCE: 14
atggacatgg ctttggcgtc taaagcctcc cctccgccat ggaatgccac cgccgccgag     60
cagccaattc caaagcgtga caaagccgct gcaaatgatt caacatgyct caatcctcaa    120
gctcatgata tgttcttgg aatcattctg ggaggtggtg ctgggactag attgtacccc    180
ttgacaaaga agcgtgccaa gcctgcagtg ccattgggtg ccaactatag actgattgat    240
attcctgtca gcaattgtct caacagcaac atatccaaga tctatgtgct aacgcaattt    300
aactctgctt ccctcaaccg tcacctctca agagcctacg ggagcaacat ggagggtac    360 aagaatgaag ggtttgttga agtcttagct gcacagcaga gcccagataa tccaaactgg    420
tttcagggta ctgcagatgc tgtaaggcag tacttgtggt tgtttgagga gcataatgtg    480
atggaatttc taattcttgc tggcgatcac ctgtaccgga tggactatga aaagttcatt    540
caggcacaca gagaaacaaa tgctgatatt accgttgctg ccctaccgat ggatgagaag    600
cgtgccactg catttggtct catgaagatt gacgaagaag gacgcattat tgaatttgca    660
```

```
gagaaaccgc aaggagagca attgcaagca atgaaagtgg atactaccat tttaggtctt    720
gatgacaaga gagctaaaga aatgcctttc attgccagta tgggtatata tgtcattagc    780
aaagacgtga tgttaaacct acttcgtgac aagttccctg gggccaatga ttttggtagt    840
gaagttattc ctggtgcaac ttcacttggg atgagagtgc aagcttattt atatgatggg    900
tactgggaag atattggtac cattgaagct ttctacaatg ccaatttggg cattacaaaa    960
aagccggtgc cagattttag cttttacgac cgatcagccc caatctacac ccaacctcga   1020
tatctaccac catcaaaaat gcttgatgct gatgtcacag atagtgtcat tggtgaaggt   1080
tgtgtgatca agaactgtaa gattcatcat tccgtggttg gactcagatc atgcatatca   1140
gagggagcaa ttatagaaga ctcactttttg atggggcag attactatga gactgatgct   1200
gacaggaagt tgttggctgc aaagggcagt gtcccaattg gcatcggcaa gaattgtcac   1260
attaaaagag ccattatcga caagaatgcc cgtataggg acaatgtgaa gatcattaac   1320
aaagacaacg ttcaagaagc ggctagggaa acagatggaa acttcatcaa gagtgggatt   1380
gtcathgtca tcaaggatgc tttgattcca agtggaatca tcatc                   1425
```

<210> SEQ ID NO 15
<211> LENGTH: 1428
<212> TYPE: DNA
<213> ORGANISM: Artificial Sequence
<220> FEATURE:
<223> OTHER INFORMATION: zea mays MP-TI nucleotide
<220> FEATURE:
<221> NAME/KEY: misc_feature
<222> LOCATION: (105)..(105)
<223> OTHER INFORMATION: r = g or a
<220> FEATURE:
<221> NAME/KEY: misc_feature
<222> LOCATION: (111)..(111)
<223> OTHER INFORMATION: y = t or c
<220> FEATURE:
<221> NAME/KEY: misc_feature
<222> LOCATION: (1389)..(1389)
<223> OTHER INFORMATION: h = a or c or t

<400> SEQUENCE: 15

```
atggacatgg ctttggcgtc taaagcctcc cctccgccat ggaatgccac cgccgccgag    60
cagccaattc caaagcgtga caaagccgct gcaaatgatt cacaracatg yctcaatcct   120
caagctcatg atagtgttct tggaatcatt ctgggaggtg gtgctgggac tagattgtac   180
cccttgacaa agaagcgtgc caagcctgca gtgccattgg gtgccaacta tagactgatt   240
gatattcctg tcagcaattg tctcaacagc aacatatcca agatctatgt gctaacgcaa   300
tttaactctg cttccctcaa ccgtcacctc tcaagagcct acgggagcaa cattggaggg   360
tacaagaatg aagggtttgt tgaagtctta gctgcacagc agagcccaga taatccaaac   420
tggtttcagg gtactgcaga tgctgtaagg cagtacttgt ggttgtttga ggagcataat   480
gtgatggaat ttctaattct tgctggcgat cacctgtacc ggatggacta tgaaaagttc   540
attcaggcac acagagaaac aaatgctgat attaccgttg ctgccctacc gatggatgag   600
aagcgtgcca ctgcatttgg tctcatgaag attgacgaag aaggacgcat tattgaattt   660
gcagagaaac cgcaaggaga gcaattgcaa gcaatgaaag tggatactac cattttaggt   720
cttgatgaca agagagctaa agaaatgcct tcattgcca gtatgggtat atatgtcatt   780
agcaaagacg tgatgttaaa cctacttcgt gacaagttcc ctggggccaa tgattttggt   840
agtgaagtta ttcctggtgc aacttcactt gggatgagag tgcaagctta tttatatgat   900
gggtactggg aagatattgg taccattgaa gctttctaca atgccaattt gggcattaca   960
```

```
aaaaagccgg tgccagattt tagcttttac gaccgatcag ccccaatcta cacccaacct    1020
cgatatctac caccatcaaa aatgcttgat gctgatgtca cagatagtgt cattggtgaa    1080
ggttgtgtga tcaagaactg taagattcat cattccgtgg ttggactcag atcatgcata    1140
tcagagggag caattataga agactcactt ttgatggggg cagattacta tgagactgat    1200
gctgacagga agttgttggc tgcaaagggc agtgtcccaa ttggcatcgg caagaattgt    1260
cacattaaaa gagccattat cgacaagaat gcccgtatag gggacaatgt gaagatcatt    1320
aacaaagaca acgttcaaga agcggctagg gaaacagatg gatacttcat caagagtggg    1380
attgtcathg tcatcaagga tgctttgatt ccaagtggaa tcatcatc                 1428
```

<210> SEQ ID NO 16
<211> LENGTH: 1428
<212> TYPE: DNA
<213> ORGANISM: Artificial Sequence
<220> FEATURE:
<223> OTHER INFORMATION: zea mays MP-TI nucleotide
<220> FEATURE:
<221> NAME/KEY: misc_feature
<222> LOCATION: (105)..(105)
<223> OTHER INFORMATION: r = g or a
<220> FEATURE:
<221> NAME/KEY: misc_feature
<222> LOCATION: (111)..(111)
<223> OTHER INFORMATION: y = t or c
<220> FEATURE:
<221> NAME/KEY: misc_feature
<222> LOCATION: (1389)..(1389)
<223> OTHER INFORMATION: h = a or c or t

<400> SEQUENCE: 16

```
atggacatgg ctttggcgtc taaagcctcc cctccgccat ggaatgccac cgccgccgag      60
cagccaattc caaagcgtga caaagccgct gcaaatgatt cagaracatg yctcaatcct    120
caagctcatg atagtgttct tggaatcatt ctgggaggtg gtgctgggac tagattgtac    180
cccttgacaa agaagcgtgc caagcctgca gtgccattgg gtgccaacta tagactgatt    240
gatattcctg tcagcaattg tctcaacagc aacatatcca agatctatgt gctaacgcaa    300
tttaactctg cttccctcaa ccgtcacctc tcaagagcct acgggagcaa cattggaggg    360
tacaagaatg aagggtttgt tgaagtctta gctgcacagc agagcccaga taatccaaac    420
tggtttcagg gtactgcaga tgctgtaagg cagtacttgt ggttgtttga ggagcataat    480
gtgatggaat ttctaattct tgctggcgat cacctgtacc ggatggacta tgaaaagttc    540
attcaggcac acagagaaac aaatgctgat attaccgttg ctgccctacc gatggatgag    600
aagcgtgcca ctgcatttgg tctcatgaag attgacgaag aaggacgcat tattgaattt    660
gcagagaaac cgcaaggaga gcaattgcaa gcaatgaaag tggatactac cattttaggt    720
cttgatgaca agagagctaa agaaatgcct tcattgccca gtatgggtat atatgtcatt    780
agcaaagacg tgatgttaaa cctacttcgt gacaagttcc ctggggccaa tgattttggt    840
agtgaagtta ttcctggtgc aacttcactt gggatgagag tgcaagctta tttatatgat    900
gggtactggg aagatattgg taccattgaa gctttctaca atgccaattt gggcattaca    960
aaaaagccgg tgccagattt tagcttttac gaccgatcag ccccaatcta cacccaacct   1020
cgatatctac caccatcaaa aatgcttgat gctgatgtca cagatagtgt cattggtgaa   1080
ggttgtgtga tcaagaactg taagattcat cattccgtgg ttggactcag atcatgcata   1140
tcagagggag caattataga agactcactt ttgatggggg cagattacta tgagactgat   1200
gctgacagga agttgttggc tgcaaagggc agtgtcccaa ttggcatcgg caagaattgt   1260
```

-continued

```
cacattaaaa gagccattat cgacaagaat gcccgtatag gggacaatgt gaagatcatt    1320
aacaaagaca acgttcaaga agcggctagg gaaacagatg gatacttcat caagagtggg    1380
attgtcathg tcatcaagga tgctttgatt ccaagtggaa tcatcatc                 1428
```

```
<210> SEQ ID NO 17
<211> LENGTH: 19
<212> TYPE: DNA
<213> ORGANISM: Artificial Sequence
<220> FEATURE:
<223> OTHER INFORMATION: zea mays oligonucleotide primer

<400> SEQUENCE: 17
gaaggagata tatccatgg                                                 19

<210> SEQ ID NO 18
<211> LENGTH: 21
<212> TYPE: DNA
<213> ORGANISM: Artificial Sequence
<220> FEATURE:
<223> OTHER INFORMATION: zea mays oligonucleotide primer

<400> SEQUENCE: 18
ggatccccgg gtaccgagct c                                              21

<210> SEQ ID NO 19
<211> LENGTH: 19
<212> TYPE: DNA
<213> ORGANISM: Artificial Sequence
<220> FEATURE:
<223> OTHER INFORMATION: zea mays oligonucleotide primer

<400> SEQUENCE: 19
gaaggagata tatccatgg                                                 19

<210> SEQ ID NO 20
<211> LENGTH: 22
<212> TYPE: DNA
<213> ORGANISM: Artificial Sequence
<220> FEATURE:
<223> OTHER INFORMATION: zea mays oligonucleotide primer

<400> SEQUENCE: 20
gttgatatct gaattcgagc tc                                             22

<210> SEQ ID NO 21
<211> LENGTH: 501
<212> TYPE: PRT
<213> ORGANISM: Hordeum vulgare subsp. vulgare

<400> SEQUENCE: 21
```

```
Met Met Ala Met Ala Thr Ala Met Ala Ala Thr Tyr Gly Ala Pro Ile
 1               5                  10                  15

Pro Ala Pro Ala Pro Ser Ala Ser Ser Pro Arg Arg Ala Ala Pro Asp
                20                  25                  30

Gly Gly Arg Arg Leu Arg Ala Val Ala Gly Arg Pro Pro Leu Phe
            35                  40                  45

Ser Pro Arg Ala Val Ser Asp Ser Arg Asn Ser Gln Thr Cys Leu Asp
        50                  55                  60

Pro Asp Ala Ser Thr Ser Val Leu Gly Ile Ile Leu Gly Gly Gly Ala
65                  70                  75                  80

Gly Thr Arg Leu Tyr Pro Leu Thr Lys Lys Arg Ala Lys Pro Ala Val
                85                  90                  95
```

```
Pro Leu Gly Ala Asn Tyr Arg Leu Ile Asp Ile Pro Val Ser Asn Cys
            100                 105                 110

Leu Asn Ser Asn Val Ser Lys Ile Tyr Val Leu Thr Gln Phe Asn Ser
        115                 120                 125

Ala Ser Leu Asn Arg His Leu Ser Arg Ala Tyr Gly Asn Asn Ile Gly
    130                 135                 140

Gly Tyr Lys Asn Asp Gly Phe Val Glu Val Leu Ala Ala Gln Gln Ser
145                 150                 155                 160

Pro Glu Asn Pro Asn Trp Phe Gln Gly Thr Ala Asp Ala Val Arg Gln
                165                 170                 175

Tyr Leu Trp Leu Phe Glu His Asn Val Met Glu Phe Leu Ile Leu
            180                 185                 190

Ala Gly Asp His Leu Tyr Arg Met Asp Tyr Gln Lys Phe Ile Gln Ala
        195                 200                 205

His Arg Glu Thr Asp Ala Asp Ile Thr Val Ala Ala Leu Pro Met Asp
    210                 215                 220

Glu Glu Arg Ala Thr Ala Phe Gly Leu Met Lys Ile Asp Asp Glu Gly
225                 230                 235                 240

Arg Ile Val Glu Phe Ser Glu Lys Pro Lys Gly Glu Lys Leu Lys Ala
                245                 250                 255

Met Met Val Val Thr Thr Ile Leu Gly Leu Asp Ser Glu Arg Ala Lys
            260                 265                 270

Glu Leu Pro Tyr Ile Ala Ser Met Gly Ile Tyr Val Phe Ser Lys Asp
        275                 280                 285

Ala Met Leu Arg Leu Leu Arg Asp Asn Phe Pro Ser Ala Asn Asp Phe
    290                 295                 300

Gly Ser Glu Val Ile Pro Gly Ala Thr Glu Ile Gly Met Arg Val Gln
305                 310                 315                 320

Ala Tyr Leu Tyr Asp Gly Tyr Trp Glu Asp Ile Gly Thr Ile Glu Ala
                325                 330                 335

Phe Tyr Asn Ala Asn Leu Gly Ile Thr Lys Lys Pro Val Pro Asp Phe
            340                 345                 350

Ser Phe Tyr Asp Arg Ser Ala Pro Ile Tyr Thr Gln Ser Arg Tyr Leu
        355                 360                 365

Pro Pro Ser Arg Val Leu Asp Ala Asp Val Thr Asp Ser Val Ile Gly
    370                 375                 380

Glu Gly Cys Val Ile Asn His Cys Lys Ile Asn His Ser Val Val Gly
385                 390                 395                 400

Leu Arg Ser Cys Ile Ser Glu Gly Ala Val Ile Glu Asp Ser Leu Leu
                405                 410                 415

Met Gly Ala Asp Tyr Tyr Glu Thr Glu Asn Asp Lys Lys Val Leu Ser
            420                 425                 430

Glu Thr Gly Gly Ile Pro Ile Gly Ile Gly Lys Asn Thr His Ile Lys
        435                 440                 445

Lys Ala Ile Ile Asp Lys Asn Ala Arg Ile Gly Glu Asn Val Lys Ile
    450                 455                 460

Ile Asn Val Asp Asp Ile Gln Glu Ala Ser Arg Glu Ser Asp Gly Tyr
465                 470                 475                 480

Phe Ile Lys Ser Gly Ile Val Ile Val Ile Lys Asp Ala Leu Ile Pro
                485                 490                 495

Ser Gly Thr Val Ile
            500
```

<210> SEQ ID NO 22
<211> LENGTH: 473
<212> TYPE: PRT
<213> ORGANISM: Triticum aestivum

<400> SEQUENCE: 22

```
Met Asp Val Pro Leu Ala Ser Lys Thr Phe Pro Ser Pro Ser Pro Ser
1               5                   10                  15

Lys Arg Glu Gln Cys Asn Val Asp Gly His Lys Ser Ser Ser Lys His
            20                  25                  30

Ala Asp Leu Asn Pro His Ala Asn Asp Ser Val Leu Gly Ile Ile Leu
        35                  40                  45

Gly Gly Gly Ala Gly Thr Arg Leu Tyr Pro Leu Thr Lys Lys Arg Ala
50                  55                  60

Lys Pro Ala Val Pro Leu Gly Ala Asn Tyr Arg Leu Ile Asp Ile Pro
65                  70                  75                  80

Val Ser Asn Cys Leu Asn Ser Asn Ile Ser Lys Ile Tyr Val Leu Thr
                85                  90                  95

Gln Phe Asn Ser Ala Ser Leu Asn Arg His Leu Ser Arg Ala Tyr Gly
            100                 105                 110

Ser Asn Ile Gly Gly Tyr Lys Asn Glu Gly Phe Val Glu Val Leu Ala
        115                 120                 125

Ala Gln Gln Ser Pro Asp Asn Pro Asp Trp Phe Gln Gly Thr Ala Asp
130                 135                 140

Ala Val Arg Gln Tyr Leu Trp Leu Phe Glu Glu His Asn Val Met Glu
145                 150                 155                 160

Tyr Leu Ile Leu Ala Gly Asp His Leu Tyr Arg Met Asp Tyr Glu Lys
                165                 170                 175

Phe Ile Gln Ala His Arg Glu Thr Asp Ala Asp Ile Thr Val Ala Ala
            180                 185                 190

Leu Pro Met Asp Glu Glu Arg Ala Thr Ala Phe Gly Leu Met Lys Ile
        195                 200                 205

Asp Glu Glu Gly Arg Ile Ile Glu Phe Ala Glu Lys Pro Lys Gly Glu
210                 215                 220

Gln Leu Lys Ala Met Met Val Asp Thr Thr Ile Leu Gly Leu Asp Asp
225                 230                 235                 240

Ala Arg Ala Lys Glu Met Pro Tyr Ile Ala Ser Met Gly Ile Tyr Val
                245                 250                 255

Ile Ser Lys His Val Met Leu Gln Leu Leu Arg Glu Gln Phe Pro Gly
            260                 265                 270

Ala Asn Asp Phe Gly Ser Glu Val Ile Pro Gly Ala Thr Ser Thr Gly
        275                 280                 285

Met Arg Val Gln Ala Tyr Leu Tyr Asp Gly Tyr Trp Glu Asp Ile Gly
290                 295                 300

Thr Ile Glu Ala Phe Tyr Asn Ala Asn Leu Gly Ile Thr Lys Lys Pro
305                 310                 315                 320

Ile Pro Asp Phe Ser Phe Tyr Asp Arg Ser Ala Pro Ile Tyr Thr Gln
                325                 330                 335

Pro Arg His Leu Pro Pro Ser Lys Val Leu Asp Ala Asp Val Thr Asp
            340                 345                 350

Ser Val Ile Gly Glu Gly Cys Val Ile Lys Asn Cys Lys Ile His His
        355                 360                 365

Ser Val Val Gly Leu Arg Ser Cys Ile Ser Glu Gly Ala Ile Ile Glu
370                 375                 380

Asp Thr Leu Leu Met Gly Ala Asp Tyr Tyr Glu Thr Glu Ala Asp Lys
```

```
                385                 390                 395                 400
Lys Leu Leu Ala Glu Lys Gly Gly Ile Pro Ile Gly Ile Gly Lys Asn
                    405                 410                 415

Ser His Ile Lys Arg Ala Ile Ile Asp Lys Asn Ala Arg Ile Gly Asp
                420                 425                 430

Asn Val Met Ile Ile Asn Val Asp Asn Val Gln Glu Ala Ala Arg Glu
            435                 440                 445

Thr Asp Gly Tyr Phe Ile Lys Ser Gly Ile Val Ile Val Ile Lys Asp
        450                 455                 460

Ala Leu Leu Pro Ser Gly Thr Val Ile
465                 470

<210> SEQ ID NO 23
<211> LENGTH: 517
<212> TYPE: PRT
<213> ORGANISM: Sorghum bicolor
<220> FEATURE:
<221> NAME/KEY: misc_feature
<222> LOCATION: (383)..(389)
<223> OTHER INFORMATION: Xaa can be any naturally occurring amino acid

<400> SEQUENCE: 23

Met Ala Met Thr Ala Ile Ala Ser Pro Ser Ser Arg Thr Leu Ile Pro
1               5                   10                  15

Pro Arg His His Gly Ala Ala Pro Ser Pro Ser Thr Ser Gly Asp Ser
                20                  25                  30

Ser Leu Arg Leu Leu Arg Ala His Pro Arg His Gly Arg Arg Ser Arg
            35                  40                  45

Gly Val Ser Val Ser Thr Pro Ala Ala Arg Ser Arg Pro Phe Val Phe
        50                  55                  60

Ser Ser Arg Ala Val Ser Asp Ser Lys Ser Ser Gln Thr Cys Leu Asp
65                  70                  75                  80

Pro Asp Ala Ser Thr Ser Val Leu Gly Ile Ile Leu Gly Gly Gly Ala
                85                  90                  95

Gly Thr Arg Leu Tyr Pro Leu Thr Lys Lys Arg Ala Lys Pro Ala Val
                100                 105                 110

Pro Leu Gly Ala Asn Tyr Arg Leu Ile Asp Ile Pro Val Ser Asn Cys
            115                 120                 125

Leu Asn Ser Asn Ile Ser Lys Ile Tyr Val Leu Thr Gln Phe Asn Ser
        130                 135                 140

Ala Ser Leu Asn Arg His Leu Ser Arg Ala Tyr Gly Ser Asn Ile Gly
145                 150                 155                 160

Gly Tyr Lys Asn Glu Gly Phe Val Glu Val Leu Ala Ala Gln Gln Ser
                165                 170                 175

Pro Asp Asn Pro Asn Trp Phe Gln Gly Thr Ala Asp Ala Val Arg Gln
            180                 185                 190

Tyr Leu Trp Leu Phe Glu Glu His Asn Val Met Glu Phe Leu Ile Leu
        195                 200                 205

Ala Gly Asp His Leu Tyr Arg Met Asp Tyr Glu Lys Phe Ile Gln Ala
210                 215                 220

His Arg Glu Thr Asp Ala Asp Ile Thr Val Ala Ala Leu Pro Met Asp
225                 230                 235                 240

Glu Ala Arg Ala Thr Ala Phe Gly Leu Met Lys Ile Asp Glu Glu Gly
                245                 250                 255

Arg Ile Ile Glu Phe Ala Glu Lys Pro Lys Gly Glu Gln Leu Lys Ala
            260                 265                 270
```

```
Met Met Val Asp Thr Thr Ile Leu Gly Leu Asp Asp Val Arg Ala Lys
            275                 280                 285

Glu Met Pro Tyr Ile Ala Ser Met Gly Ile Tyr Val Phe Ser Lys Asp
        290                 295                 300

Val Met Leu Gln Leu Leu Arg Glu Gln Phe Pro Gly Ala Asn Asp Phe
305                 310                 315                 320

Gly Ser Glu Val Ile Pro Gly Ala Thr Thr Ile Gly Lys Arg Val Gln
            325                 330                 335

Ala Tyr Leu Tyr Asp Gly Tyr Trp Glu Asp Ile Gly Thr Ile Thr Ala
            340                 345                 350

Phe Tyr Asn Ala Asn Leu Gly Ile Thr Lys Pro Val Pro Asp Phe
            355                 360                 365

Ser Phe Tyr Asp Arg Ser Ala Pro Ile Tyr Thr Gln Pro Arg Xaa Xaa
        370                 375                 380

Xaa Xaa Xaa Xaa Xaa Leu Asp Ala Asp Val Thr Asp Ser Val Ile Gly
385                 390                 395                 400

Glu Gly Cys Val Ile Lys Asn Cys Lys Ile His His Ser Val Val Gly
                405                 410                 415

Leu Arg Ser Cys Ile Ser Glu Gly Ala Ile Ile Glu Asp Thr Leu Leu
            420                 425                 430

Met Gly Ala Asp Tyr Tyr Glu Thr Glu Ala Asp Lys Lys Leu Leu Ala
        435                 440                 445

Glu Asn Gly Gly Ile Pro Ile Gly Ile Gly Lys Asn Ser His Ile Arg
450                 455                 460

Arg Ala Ile Ile Asp Lys Asn Ala Arg Ile Gly Asp Asn Val Lys Ile
465                 470                 475                 480

Leu Asn Ala Asp Asn Val Gln Glu Ala Ala Arg Glu Thr Asp Gly Tyr
            485                 490                 495

Phe Ile Lys Gly Gly Ile Val Ile Val Ile Leu Asp Ala Leu Leu Pro
                500                 505                 510

Ser Gly Thr Val Ile
            515

<210> SEQ ID NO 24
<211> LENGTH: 521
<212> TYPE: PRT
<213> ORGANISM: Solanum tuberosum

<400> SEQUENCE: 24

Met Ala Ala Ser Ile Gly Ala Leu Lys Ser Ser Pro Ser Ser Asn Asn
1               5                   10                  15

Cys Ile Asn Glu Arg Arg Asn Asp Ser Thr Arg Ala Val Ser Ser Arg
            20                  25                  30

Asn Leu Ser Phe Ser Ser Ser His Leu Ala Gly Asp Lys Leu Met Pro
        35                  40                  45

Val Ser Ser Leu Arg Ser Gln Gly Val Arg Phe Asn Val Arg Arg Ser
    50                  55                  60

Pro Met Ile Val Ser Pro Lys Ala Val Ser Asp Ser Gln Asn Ser Gln
65                  70                  75                  80

Thr Cys Leu Asp Pro Asp Ala Ser Arg Ser Val Leu Gly Ile Ile Leu
            85                  90                  95

Gly Gly Gly Ala Gly Thr Arg Leu Tyr Pro Leu Thr Lys Lys Arg Ala
            100                 105                 110

Lys Pro Ala Val Pro Leu Gly Ala Asn Tyr Arg Leu Ile Asp Ile Pro
        115                 120                 125
```

Val Ser Asn Cys Leu Asn Ser Asn Ile Ser Lys Ile Tyr Val Leu Thr
130                 135                 140

Gln Phe Asn Ser Ala Ser Leu Asn Arg His Leu Ser Arg Ala Tyr Ala
145                 150                 155                 160

Ser Asn Met Gly Gly Tyr Lys Asn Glu Gly Phe Val Glu Val Leu Ala
            165                 170                 175

Ala Gln Gln Ser Pro Glu Asn Pro Asp Trp Phe Gln Gly Thr Ala Asp
        180                 185                 190

Ala Val Arg Gln Tyr Leu Trp Leu Phe Glu Glu His Thr Val Leu Glu
    195                 200                 205

Tyr Leu Ile Leu Ala Gly Asp His Leu Tyr Arg Met Asp Tyr Glu Lys
210                 215                 220

Phe Ile Gln Ala His Arg Glu Thr Asp Ala Asp Ile Thr Val Ala Ala
225                 230                 235                 240

Leu Pro Met Asp Glu Lys Arg Ala Thr Ala Phe Gly Leu Met Lys Ile
                245                 250                 255

Asp Glu Glu Gly Arg Ile Ile Glu Phe Ala Glu Lys Pro Gln Gly Glu
            260                 265                 270

Gln Leu Gln Ala Met Lys Val Asp Thr Thr Ile Leu Gly Leu Asp Asp
        275                 280                 285

Lys Arg Ala Lys Glu Met Pro Phe Ile Ala Ser Met Gly Ile Tyr Val
    290                 295                 300

Ile Ser Lys Asp Val Met Leu Asn Leu Leu Arg Asp Lys Phe Pro Gly
305                 310                 315                 320

Ala Asn Asp Phe Gly Ser Glu Val Ile Pro Gly Ala Thr Ser Leu Gly
                325                 330                 335

Met Arg Val Gln Ala Tyr Leu Tyr Asp Gly Tyr Trp Glu Asp Ile Gly
            340                 345                 350

Thr Ile Glu Ala Phe Tyr Asn Ala Asn Leu Gly Ile Thr Lys Lys Pro
        355                 360                 365

Val Pro Asp Phe Ser Phe Tyr Asp Arg Ser Ala Pro Ile Tyr Thr Gln
    370                 375                 380

Pro Arg Tyr Leu Pro Pro Ser Lys Met Leu Asp Ala Asp Val Thr Asp
385                 390                 395                 400

Ser Val Ile Gly Glu Gly Cys Val Ile Lys Asn Cys Lys Ile His His
                405                 410                 415

Ser Val Val Gly Leu Arg Ser Cys Ile Ser Glu Gly Ala Ile Ile Glu
            420                 425                 430

Asp Ser Leu Leu Met Gly Ala Asp Tyr Tyr Glu Thr Asp Ala Asp Arg
        435                 440                 445

Lys Leu Leu Ala Ala Lys Gly Ser Val Pro Ile Gly Ile Gly Lys Asn
    450                 455                 460

Cys His Ile Lys Arg Ala Ile Ile Asp Lys Asn Ala Arg Ile Gly Asp
465                 470                 475                 480

Asn Val Lys Ile Ile Asn Lys Asp Asn Val Gln Glu Ala Ala Arg Glu
                485                 490                 495

Thr Asp Gly Tyr Phe Ile Lys Ser Gly Ile Val Ile Val Ile Lys Asp
            500                 505                 510

Ala Leu Ile Pro Ser Gly Ile Ile Ile
        515                 520

<210> SEQ ID NO 25
<211> LENGTH: 500
<212> TYPE: PRT
<213> ORGANISM: Oryza sativa Japonica Group

<400> SEQUENCE: 25

```
Met Ala Met Met Ala Met Gly Ala Ala Ser Trp Ala Pro Ile Pro Ala
1               5                   10                  15
Pro Ala Arg Ala Ala Ala Phe Tyr Pro Gly Arg Asp Leu Ala Ala
            20                  25                  30
Ala Arg Arg Arg Gly Ala Ala Arg Arg Pro Phe Val Phe Thr
        35                  40                  45
Pro Arg Ala Val Ser Asp Ser Arg Ser Gln Thr Cys Leu Asp Pro
    50                  55                  60
Asp Ala Ser Thr Ser Val Leu Gly Ile Ile Leu Gly Gly Gly Ala Gly
65                  70                  75                  80
Thr Arg Leu Tyr Pro Leu Thr Lys Lys Arg Ala Lys Pro Ala Val Pro
                85                  90                  95
Leu Gly Ala Asn Tyr Arg Leu Ile Asp Ile Pro Val Ser Asn Cys Leu
            100                 105                 110
Asn Ser Asn Val Ser Lys Ile Tyr Val Leu Thr Gln Phe Asn Ser Ala
        115                 120                 125
Ser Leu Asn Gly His Leu Ser Arg Ala Tyr Gly Asn Asn Ile Gly Gly
    130                 135                 140
Tyr Lys Asn Glu Gly Phe Val Glu Val Leu Ala Ala Gln Gln Ser Pro
145                 150                 155                 160
Glu Asn Pro Asn Trp Phe Gln Gly Thr Ala Asp Ala Val Arg Gln Tyr
                165                 170                 175
Leu Trp Leu Phe Glu Glu His Asn Val Met Glu Phe Leu Ile Leu Ala
            180                 185                 190
Gly Asp His Leu Tyr Arg Met Asp Tyr Gln Lys Phe Ile Gln Ala His
        195                 200                 205
Arg Glu Thr Asn Ala Asp Ile Thr Val Ala Ala Leu Pro Met Asp Glu
    210                 215                 220
Glu Arg Ala Thr Ala Phe Gly Leu Met Lys Ile Asp Asp Glu Gly Arg
225                 230                 235                 240
Ile Ile Glu Phe Ala Glu Lys Pro Lys Gly Glu Lys Leu Lys Ser Met
                245                 250                 255
Met Val Asp Thr Thr Ile Leu Gly Leu Asp Thr Glu Arg Ala Lys Glu
            260                 265                 270
Leu Pro Tyr Ile Ala Ser Met Gly Ile Tyr Val Phe Ser Lys Asp Val
        275                 280                 285
Met Leu Lys Leu Leu Arg Gln Asn Phe Pro Ala Ala Asn Asp Phe Gly
    290                 295                 300
Ser Glu Val Ile Pro Gly Ala Thr Glu Ile Gly Met Arg Val Gln Ala
305                 310                 315                 320
Tyr Leu Tyr Asp Gly Tyr Trp Glu Asp Ile Gly Thr Ile Glu Ala Phe
                325                 330                 335
Tyr Asn Ala Asn Leu Gly Ile Thr Lys Lys Pro Val Pro Asp Phe Ser
            340                 345                 350
Phe Tyr Asp Arg Ser Ala Ala Ile Tyr Thr Gln Pro Arg Tyr Leu Pro
        355                 360                 365
Pro Ser Lys Val Leu Asp Ala Asp Val Thr Asp Ser Val Ile Gly Glu
    370                 375                 380
Gly Cys Val Ile Arg His Cys Thr Ile Asn His Ser Val Val Gly Leu
385                 390                 395                 400
Arg Ser Cys Ile Ser Glu Gly Ala Val Ile Glu Asp Ser Leu Leu Met
                405                 410                 415
```

```
Gly Ala Asp Tyr Tyr Glu Thr Glu Thr Asp Lys Lys Ala Leu Ser Glu
            420                 425                 430

Thr Gly Gly Ile Pro Ile Gly Ile Gly Lys Asn Ala His Ile Arg Lys
            435                 440                 445

Ala Ile Ile Asp Lys Asn Ala Arg Ile Gly Glu Asn Val Lys Ile Ile
450                 455                 460

Asn Val Asp Asn Ile Gln Glu Ala Ser Arg Glu Thr Asp Gly Tyr Phe
465                 470                 475                 480

Ile Lys Ser Gly Ile Val Ile Val Ile Lys Asp Ala Leu Ile Pro Ser
                485                 490                 495

Gly Thr Val Ile
            500

<210> SEQ ID NO 26
<211> LENGTH: 521
<212> TYPE: PRT
<213> ORGANISM: Solanum tuberosum

<400> SEQUENCE: 26

Met Ala Ala Ser Ile Gly Ala Leu Lys Ser Ser Pro Ser Ser Asn Asn
1               5                   10                  15

Cys Ile Asn Glu Arg Arg Asn Asp Ser Thr Arg Ala Val Ser Ser Arg
            20                  25                  30

Asn Leu Ser Phe Ser Ser Ser His Leu Ala Gly Asp Lys Leu Met Pro
        35                  40                  45

Val Ser Ser Leu Arg Ser Gln Gly Val Arg Phe Asn Val Arg Arg Ser
    50                  55                  60

Pro Met Ile Val Ser Pro Lys Ala Val Ser Asp Ser Gln Asn Ser Gln
65                  70                  75                  80

Thr Cys Leu Asp Pro Asp Ala Ser Arg Ser Val Leu Gly Ile Ile Leu
                85                  90                  95

Gly Gly Gly Ala Gly Thr Arg Leu Tyr Pro Leu Thr Lys Lys Arg Ala
            100                 105                 110

Lys Pro Ala Val Pro Leu Gly Ala Asn Tyr Arg Leu Ile Asp Ile Pro
        115                 120                 125

Val Ser Asn Cys Leu Asn Ser Asn Ile Ser Lys Ile Tyr Val Leu Thr
    130                 135                 140

Gln Phe Asn Ser Ala Ser Leu Asn Arg His Leu Ser Arg Ala Tyr Ala
145                 150                 155                 160

Ser Asn Met Gly Gly Tyr Lys Asn Glu Gly Phe Val Glu Val Leu Ala
                165                 170                 175

Ala Gln Gln Ser Pro Glu Asn Pro Asp Trp Phe Gln Gly Thr Ala Asp
            180                 185                 190

Ala Val Arg Gln Tyr Leu Trp Leu Phe Glu Glu His Thr Val Leu Glu
        195                 200                 205

Tyr Leu Ile Leu Ala Gly Asp His Leu Tyr Arg Met Asp Tyr Glu Lys
    210                 215                 220

Phe Ile Gln Ala His Arg Glu Thr Asp Ala Asp Ile Thr Val Ala Ala
225                 230                 235                 240

Leu Pro Met Asp Glu Lys Arg Ala Thr Ala Phe Gly Leu Met Lys Ile
                245                 250                 255

Asp Glu Glu Gly Arg Ile Ile Glu Phe Ala Glu Lys Pro Gln Gly Glu
            260                 265                 270

Gln Leu Gln Ala Met Lys Val Asp Thr Thr Ile Leu Gly Leu Asp Asp
        275                 280                 285
```

| | | | | | | | | | | | | |
|---|---|---|---|---|---|---|---|---|---|---|---|---|
|Lys|Arg|Ala|Lys|Glu|Met|Pro|Phe|Ile|Ala|Ser|Met|Gly|Ile|Tyr|Val|
| |290| | | |  |295| | | | |300| | | | |

Lys Arg Ala Lys Glu Met Pro Phe Ile Ala Ser Met Gly Ile Tyr Val
    290             295             300

Ile Ser Lys Asp Val Met Leu Asn Leu Leu Arg Asp Lys Phe Pro Gly
305             310             315             320

Ala Asn Asp Phe Gly Ser Glu Val Ile Pro Gly Ala Thr Ser Leu Gly
            325             330             335

Met Arg Val Gln Ala Tyr Leu Tyr Asp Gly Tyr Trp Glu Asp Ile Gly
            340             345             350

Thr Ile Glu Ala Phe Tyr Asn Ala Asn Leu Gly Ile Thr Lys Lys Pro
        355             360             365

Val Pro Asp Phe Ser Phe Tyr Asp Arg Ser Ala Pro Ile Tyr Thr Gln
    370             375             380

Pro Arg Tyr Leu Pro Pro Ser Lys Met Leu Asp Ala Asp Val Thr Asp
385             390             395             400

Ser Val Ile Gly Glu Gly Cys Val Ile Lys Asn Cys Lys Ile His His
            405             410             415

Ser Val Val Gly Leu Arg Ser Cys Ile Ser Glu Gly Ala Ile Ile Glu
            420             425             430

Asp Ser Leu Leu Met Gly Ala Asp Tyr Tyr Glu Thr Asp Ala Asp Arg
        435             440             445

Lys Leu Leu Ala Ala Lys Gly Ser Val Pro Ile Gly Ile Gly Lys Asn
    450             455             460

Cys His Ile Lys Arg Ala Ile Ile Asp Lys Asn Ala Arg Ile Gly Asp
465             470             475             480

Asn Val Lys Ile Ile Asn Lys Asp Asn Val Gln Glu Ala Ala Arg Glu
            485             490             495

Thr Asp Gly Tyr Phe Ile Lys Ser Gly Ile Val Thr Val Ile Lys Asp
            500             505             510

Ala Leu Ile Pro Ser Gly Ile Ile Ile
        515             520